(12) United States Patent
Gysling et al.

(10) Patent No.: US 7,328,624 B2
(45) Date of Patent: Feb. 12, 2008

(54) PROBE FOR MEASURING PARAMETERS OF A FLOWING FLUID AND/OR MULTIPHASE MIXTURE

(75) Inventors: Daniel L. Gysling, Glastonbury, CT (US); Douglas H. Loose, Southington, CT (US); Thomas W. Engel, East Hampton, CT (US); Paul F. Croteau, Columbia, CT (US)

(73) Assignee: CIDRA Corporation, Wallingford, CT (US)

( * ) Notice: Subject to any disclaimer, the term of this patent is extended or adjusted under 35 U.S.C. 154(b) by 0 days.

(21) Appl. No.: 10/412,839

(22) Filed: Apr. 10, 2003

(65) Prior Publication Data

US 2004/0069069 A1 Apr. 15, 2004

Related U.S. Application Data

(63) Continuation-in-part of application No. 10/376,427, filed on Feb. 26, 2003, now Pat. No. 7,032,432, and a continuation-in-part of application No. 10/349,716, filed on Jan. 23, 2003.
(60) Provisional application No. 60/371,606, filed on Apr. 10, 2002, provisional application No. 60/427,964, filed on Nov. 20, 2002, provisional application No. 60/451,375, filed on Feb. 28, 2003, provisional application No. 60/359,785, filed on Feb. 26, 2002, provisional application No. 60/351,232, filed on Jan. 23, 2002, provisional application No. 60/375,847, filed on Apr. 24, 2002, provisional application No. 60/425,436, filed on Nov. 12, 2002, provisional application No. 60/426,724, filed on Nov. 15, 2002.

(51) Int. Cl.
*G01L 13/02* (2006.01)
*G01L 15/00* (2006.01)
(52) U.S. Cl. ............... 73/736; 73/861.49; 73/19.01; 73/61.41; 73/61.43; 73/61.44; 73/61.47; 73/152.18; 73/152.42; 73/152.51

(58) Field of Classification Search ............... 73/19.01, 73/24.01, 61.41, 61.43–61.45, 61.47, 152.01–152.02, 73/152.18–152.19, 152.22, 152.42, 152.51, 73/736, 861.49, 248
See application file for complete search history.

(56) References Cited

U.S. PATENT DOCUMENTS 3,715,709 A * 2/1973 Zacharias et al. ............. 367/95
(Continued)

FOREIGN PATENT DOCUMENTS

GB        1578660 A      11/1980
(Continued)

OTHER PUBLICATIONS

U.S. Appl. No. 60/371,606, filed Apr. 10, 2002.
(Continued)

*Primary Examiner*—Hezron Williams
*Assistant Examiner*—Samir M. Shah
(74) *Attorney, Agent, or Firm*—Michael Grillo

(57) ABSTRACT

A probe 10,170 is provided that measures the speed of sound and/or vortical disturbances propagating in a single phase fluid flow and/or multiphase mixture to determine parameters, such as mixture quality, particle size, vapor/mass ratio, liquid/vapor ratio, mass flow rate, enthalpy and volumetric flow rate of the flow in a pipe or unconfined space, for example, using acoustic and/or dynamic pressures. The probe includes a spatial array of unsteady pressure sensors 15-18 placed at predetermined axial locations $x_1$-$x_N$ disposed axially along a tube 14. For measuring at least one parameter of a saturated vapor/liquid mixture 12, such as steam, flowing in the tube 14. The pressure sensors 15-18 provide acoustic pressure signals $P_1(t)$-$P_N(t)$ to a signal processing unit 30 which determines the speed of sound $a_{mix}$ propagating through of the saturated vapor/liquid mixture 12 in the tube 14 using acoustic spatial array signal processing techniques. Frequency based sound speed is determined utilizing a dispersion model to determine the parameters of interest.

25 Claims, 29 Drawing Sheets

U.S. PATENT DOCUMENTS

| | | | |
|---|---|---|---|
| 4,048,853 A | 9/1977 | Smith et al. | 73/861.25 |
| 4,080,837 A | 3/1978 | Alexander et al. | 73/61.45 |
| 4,248,085 A | 2/1981 | Coulthard | 73/861.06 |
| 4,433,573 A * | 2/1984 | Hulin | 73/152.32 |
| 4,445,389 A | 5/1984 | Potzick et al. | 73/861.27 |
| 4,520,320 A * | 5/1985 | Potzick et al. | 327/7 |
| 4,677,305 A | 6/1987 | Ellinger | 73/290 V |
| 4,896,540 A * | 1/1990 | Shakkottai et al. | 73/861.02 |
| 5,040,415 A | 8/1991 | Barkhoudarian | 73/861.03 |
| 5,083,452 A | 1/1992 | Hope | 73/61 R |
| 5,146,414 A * | 9/1992 | McKown et al. | 702/49 |
| 5,218,197 A | 6/1993 | Carroll | 250/227.19 |
| 5,285,675 A | 2/1994 | Colgate et al. | 73/23.2 |
| 5,363,342 A | 11/1994 | Layton et al. | 367/149 |
| 5,367,911 A * | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,660,977 A | 8/1997 | Flores-Cotera et al. | |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A * | 12/1998 | Berthold et al. | 385/12 |
| 5,948,959 A | 9/1999 | Peloquin | 73/1.83 |
| 6,016,702 A | 1/2000 | Maron | 73/705 |
| 6,081,065 A * | 6/2000 | Nabity et al. | 310/338 |
| 6,202,494 B1 | 3/2001 | Riebel et al. | 73/861.29 |
| 6,354,147 B1 | 3/2002 | Gysling et al. | 73/61.79 |
| 6,378,357 B1 | 4/2002 | Han et al. | 73/54.41 |
| 6,435,030 B1 | 8/2002 | Gysling et al. | 73/587 |
| 6,443,226 B1 | 9/2002 | Diener et al. | 166/241.6 |
| 6,450,037 B1 | 9/2002 | McGuinn et al. | 73/705 |
| 6,463,813 B1 | 10/2002 | Gysling | 73/862.59 |
| 6,536,291 B1 | 3/2003 | Gysling et al. | 73/861.42 |
| 6,550,342 B2 | 4/2003 | Croteau et al. | 73/800 |
| 6,550,345 B1 * | 4/2003 | Letton | 73/861.27 |
| 6,558,036 B2 | 5/2003 | Gysling et al. | 374/147 |
| 6,575,043 B1 * | 6/2003 | Huang et al. | 73/861.25 |
| 6,587,798 B2 | 7/2003 | Kersey et al. | 702/50 |
| 6,601,458 B1 | 8/2003 | Gysling et al. | 73/861.04 |
| 6,609,069 B2 | 8/2003 | Gysling | 702/48 |
| 6,672,163 B2 | 1/2004 | Han et al. | |
| 6,691,584 B2 | 2/2004 | Gysling et al. | 73/861.42 |
| 6,698,297 B2 | 3/2004 | Gysling | 73/861.63 |
| 6,732,575 B2 | 5/2004 | Gysling et al. | 73/61.79 |
| 6,782,150 B2 | 8/2004 | Davis et al. | 385/12 |
| 6,813,962 B2 | 11/2004 | Gysling et al. | 73/861.26 |
| 6,837,098 B2 | 1/2005 | Gysling et al. | 73/61.79 |
| 6,862,920 B2 | 3/2005 | Gysling et al. | 73/61.79 |
| 6,868,737 B2 | 3/2005 | Croteau et al. | 73/800 |
| 6,889,562 B2 | 5/2005 | Gysling et al. | 73/861.42 |
| 6,898,541 B2 | 5/2005 | Gysling et al. | 702/100 |
| 6,988,411 B2 * | 1/2006 | Gysling et al. | 73/645 |
| 7,010,962 B2 | 3/2006 | Sinha | |
| 7,062,976 B2 | 6/2006 | Gysling et al. | |
| 7,086,278 B2 | 8/2006 | Gysling et al. | |
| 7,146,864 B2 | 12/2006 | Sullivan et al. | |
| 2002/0123852 A1 | 9/2002 | Gysling et al. | |
| 2002/0129662 A1 | 9/2002 | Gysling et al. | |
| 2003/0038231 A1 | 2/2003 | Davis et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2003/0235263 A1 * | 12/2003 | Rajendran et al. | 376/248 |
| 2004/0016284 A1 | 1/2004 | Gysling et al. | |
| 2004/0069069 A1 | 4/2004 | Croteau et al. | |
| 2004/0255695 A1 | 12/2004 | Gysling et al. | |

FOREIGN PATENT DOCUMENTS

| | | |
|---|---|---|
| JP | 07229964 A | 8/1995 |
| JP | 2003043017 A | 2/2003 |
| WO | WO 9314382 | 7/1993 |
| WO | WO 9967629 | 12/1999 |
| WO | WO 0000793 | 1/2000 |
| WO | WO 01/02811 A1 * | 1/2001 |
| WO | WO 0102810 | 1/2001 |

OTHER PUBLICATIONS

U.S. Appl. No. 60/427,964, filed Nov. 20, 2002.
U.S. Appl. No. 60/451,375, filed Feb. 28, 2003.
U.S. Appl. No. 10/376,427, filed Feb. 26, 2003.
U.S. Appl. No. 60/359,785, filed Feb. 26, 2002.
U.S. Appl. No. 10/349,716, filed Jan. 23, 2003.
U.S. Appl. No. 60/351,232, filed Jan. 23, 2002.
U.S. Appl. No. 60/359,785, filed Feb. 26, 2002.
U.S. Appl. No. 60/375,847, filed Apr. 24, 2002.
U.S. Appl. No. 60/425,436, filed Nov. 12, 2002.
U.S. Appl. No. 60/426,724, filed Nov. 15, 2002.
"Noise and Vibration Control Engineering Principles and Applications", Leo L. Beranek and Istvan L. Ver, A. Wiley Interscience Publication, pp. 537-541, Aug. 1992.
"Two Decades of Array Signal Processing Research, The Parametric Approach", H. Krim and M. Viberg, IEEE Signal Processing Magazine, Jul. 1996, pp. 67-94.
"Development of an array of pressure sensors with PVDF film, Experiments in Fluids 26", Jan. 8, 1999, Springer-Verlag.
"Viscous Attentuation of Acoustic Waves in Suspensions" by R.L. Gibson, Jr. and M.N. Toksoz.
Sonar-Based Volumetric Flow Meter for Chemical and Petrochemical Applications by: Daniel L. Gysling and Douglas H. Loose—Feb. 14, 2003.
"Sonar-Based Volumetric Flow Meter for Pulp and Paper Applications" by: Daniel L. Gysling and Douglas H. Loose—Dec. 3, 2002.
"Flow Velocity Measurement using Spatial Filter" By: Yoshio Kurita, Takaharu Matsumoto and Yukitake Shibata , Nov. 1979.
"Dynamite Modelling of Gas Hold-Up in Different Electrolyte Systems" By: H. Kellermann, K. Juttner, G. Kreysa—Journal of Applied Electrochemistry 18 (1998) pp. 311-319.

* cited by examiner

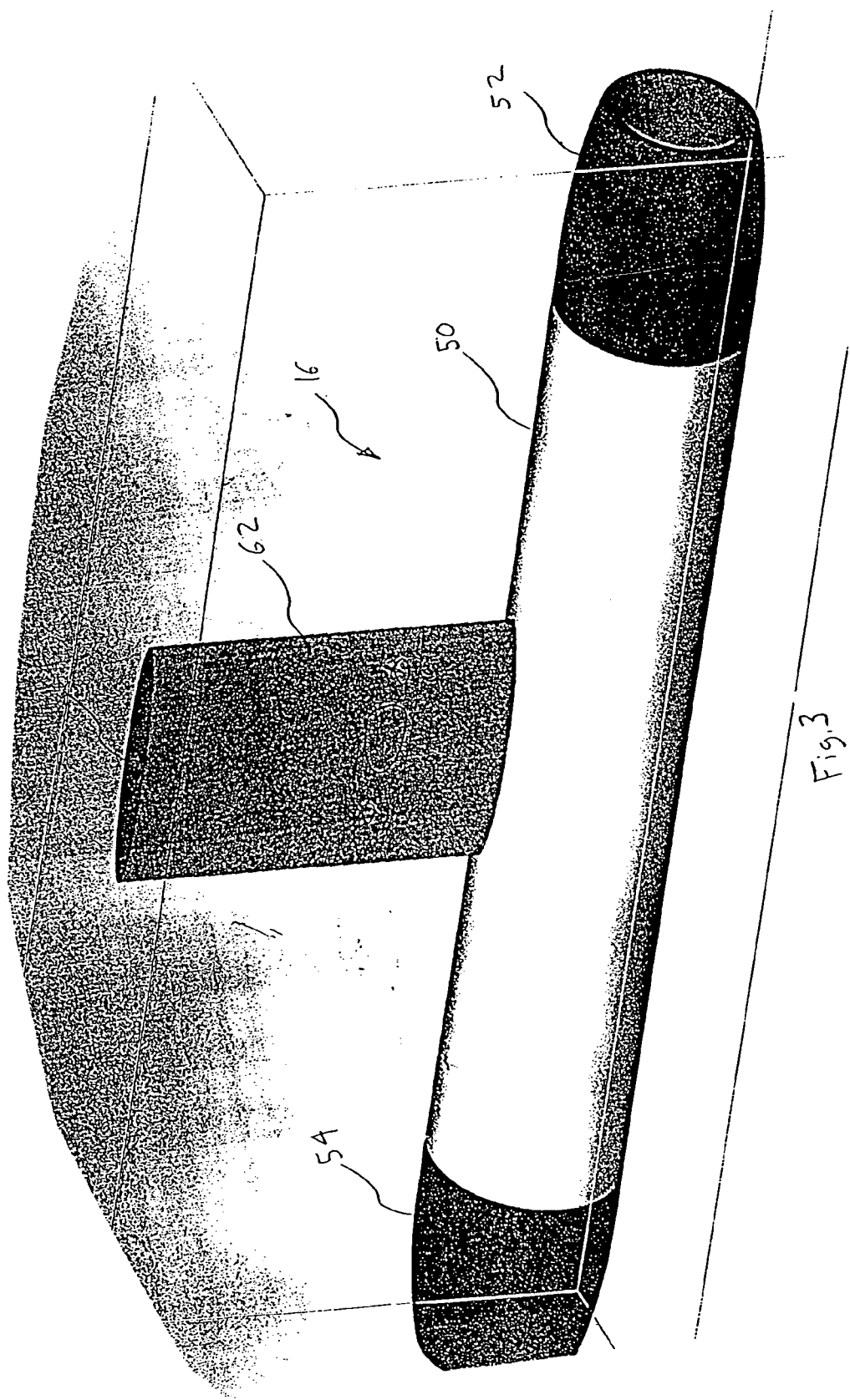

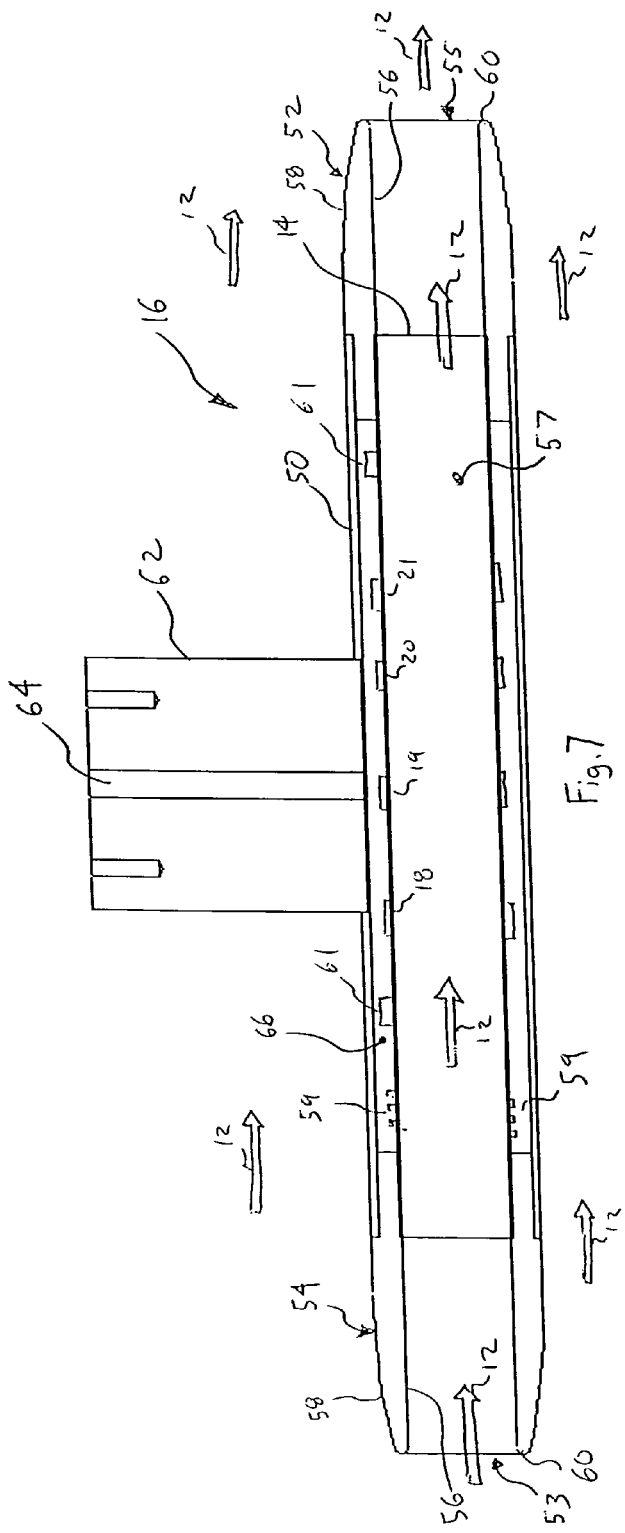
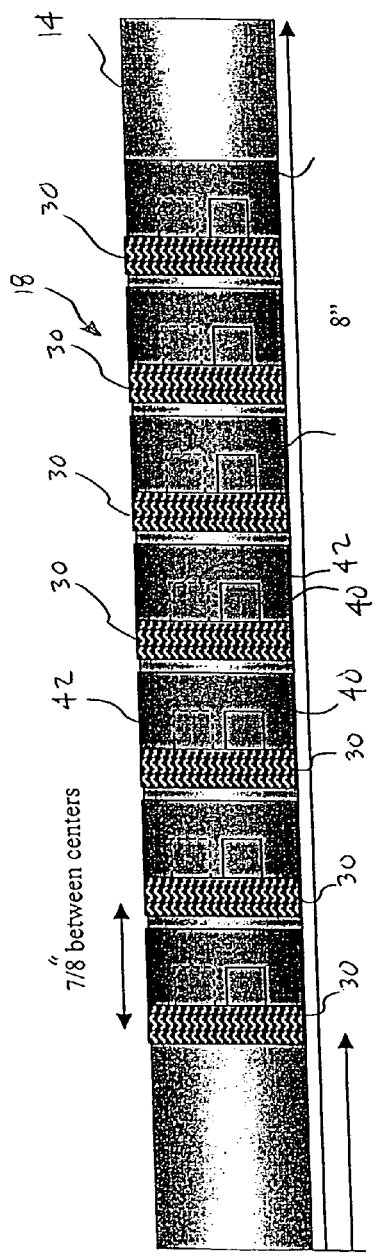
Fig. 7
Fig. 8

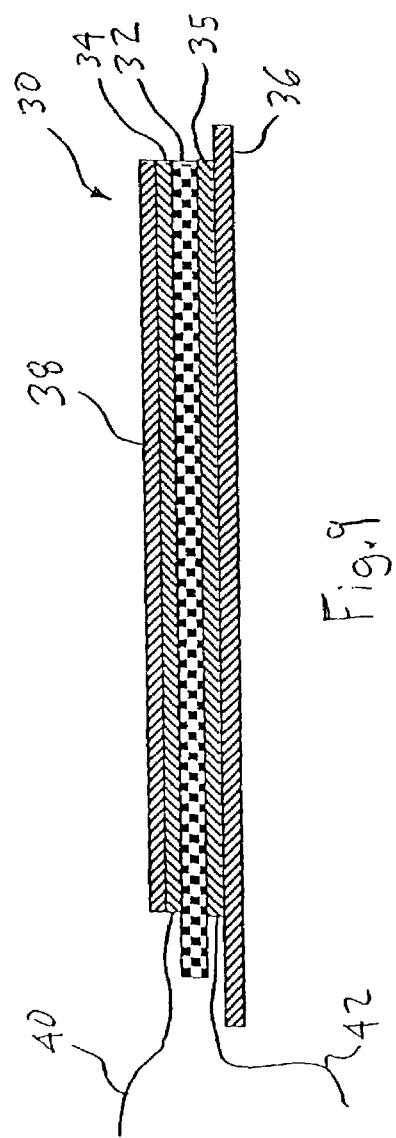
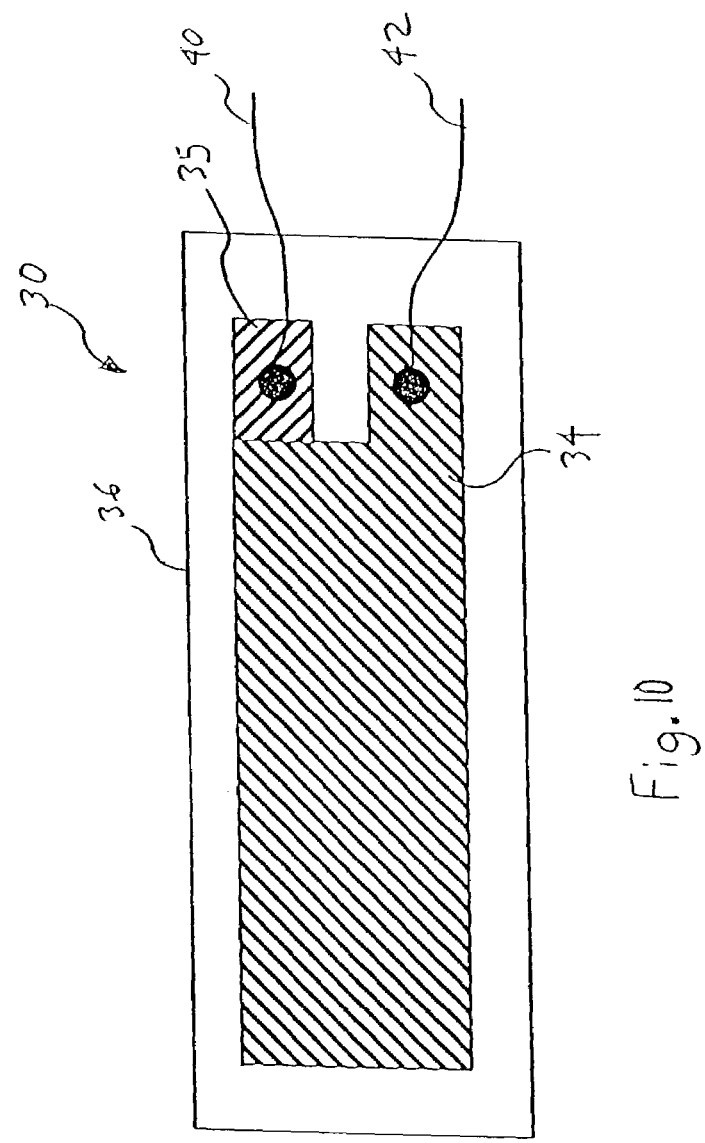
Fig. 9
Fig. 10 k-ω Plot for Run #5, Ma 0.5 Setpoint, 0° Incidence

"Acoustic Ridge" of upstream traveling wave.
2*pi*slope = sound speed − flow velocity "Acoustic Ridge" of downstream traveling wave.
2*pi*slope = sound speed + flow velocity

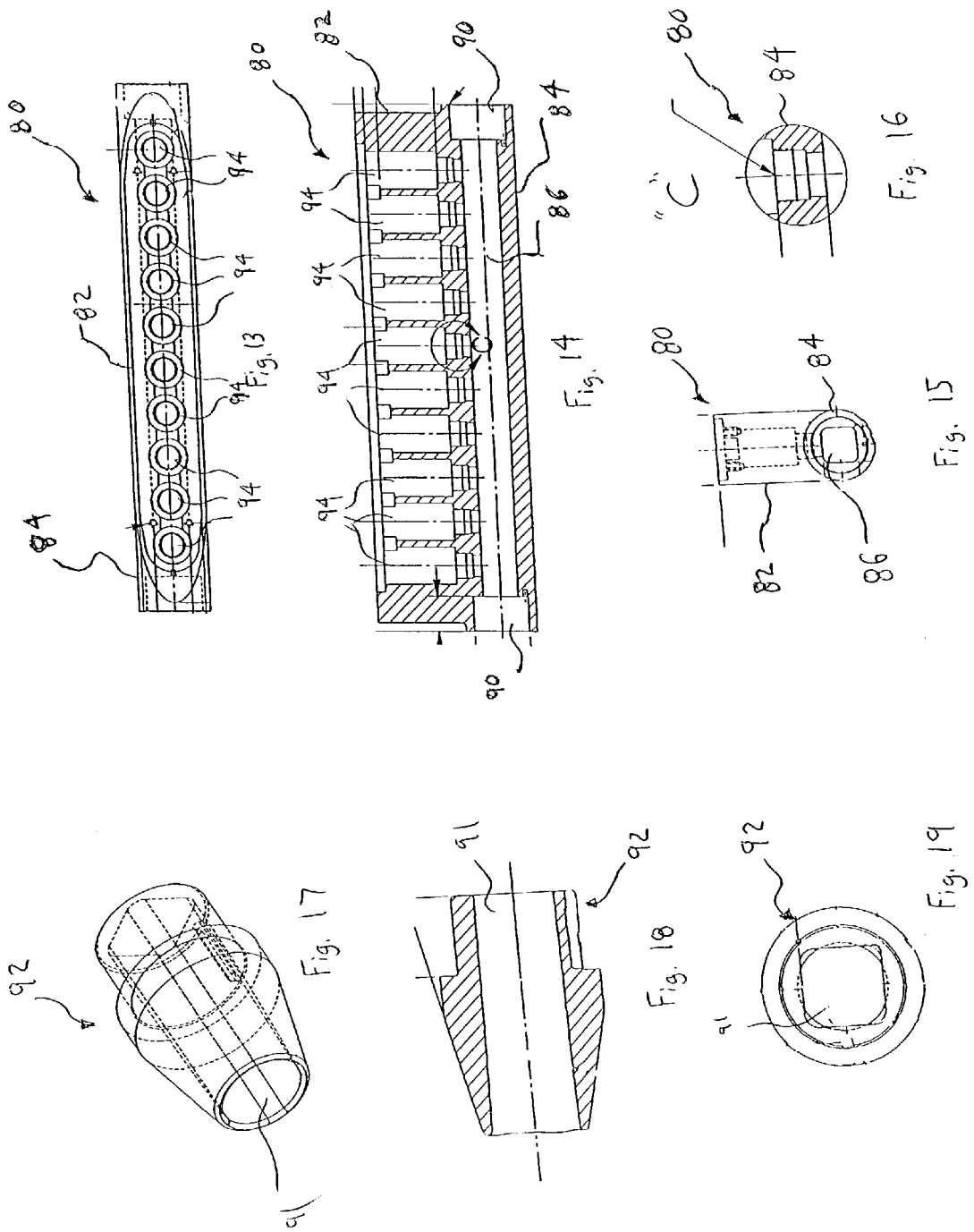

k-ω Plot for Run #4, Ma 0.6 Setpoint, 0° Incidence

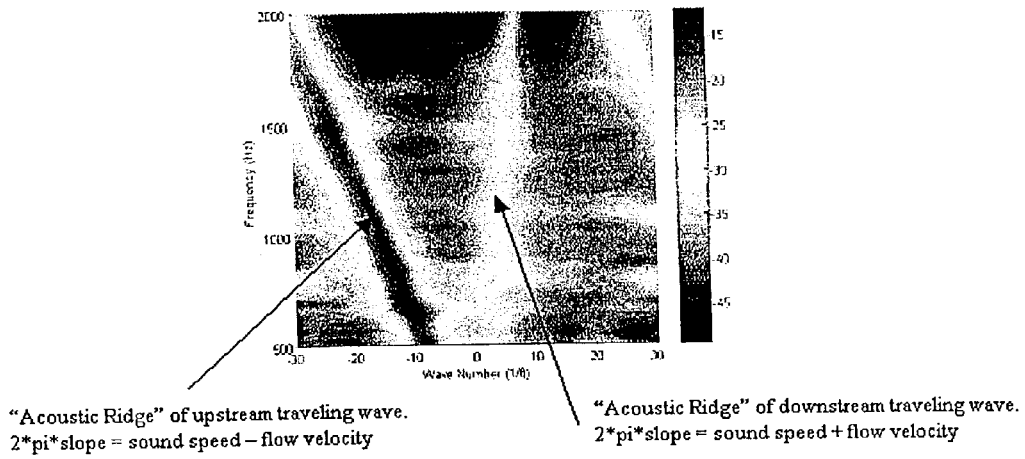

"Acoustic Ridge" of upstream traveling wave.
2*pi*slope = sound speed − flow velocity "Acoustic Ridge" of downstream traveling wave.
2*pi*slope = sound speed + flow velocity

Fig. 21 k-ω Plot for Run #8, Ma 0.5 Setpoint, 10° Incidence

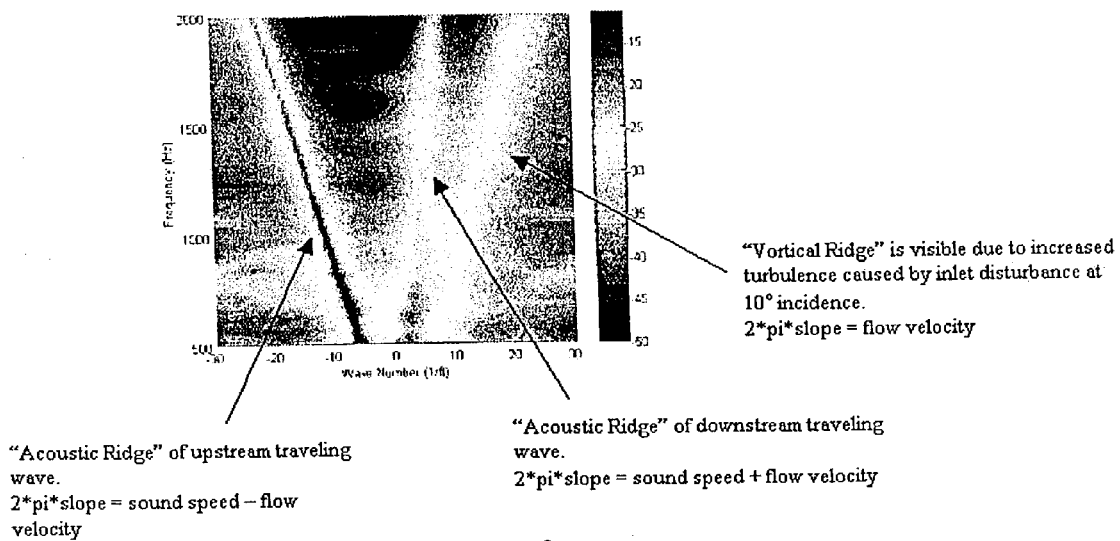

"Vortical Ridge" is visible due to increased turbulence caused by inlet disturbance at 10° incidence.
2*pi*slope = flow velocity "Acoustic Ridge" of upstream traveling wave.
2*pi*slope = sound speed − flow velocity "Acoustic Ridge" of downstream traveling wave.
2*pi*slope = sound speed + flow velocity

Fig 22

PROBE FOR MEASURING PARAMETERS OF A FLOWING FLUID AND/OR MULTIPHASE MIXTURE

CROSS-REFERENCE TO RELATED PATENT APPLICATIONS

This application claims the benefit of U.S. Provisional Application No. 60/371,606 filed Apr. 10, 2002, U.S. Provisional Application No. 60/427,964 filed Nov. 20, 2002, and U.S. Provisional Application No. 60/451,375 filed Feb. 28, 2003; and is a continuation-in-part of U.S. patent application Ser. No. 10/376,427 filed Feb. 26, 2003, now U.S. Pat. No. 7,032,432 which claimed the benefit of U.S. Provisional Application No. 60/359,785, filed Feb. 26, 2002; and is a continuation-in-part of U.S. patent application Ser. No. 10/349,716, filed Jan. 23, 2003, which claims the benefit of U.S. Provisional Application No. 60/351,232, filed Jan. 23, 2002; U.S. Provisional Application No. 60/359,785, filed Feb. 26, 2002; U.S. Provisional Application No. 60/375,847, filed Apr. 24, 2002; U.S. Provisional Application No. 60/425,436, filed Nov. 12, 2002; and U.S. Provisional Application No. 60/426,724, filed Nov. 15, 2002, all of which are incorporated herein by reference in their entirety.

TECHNICAL FIELD

This invention relates to an apparatus for measuring the parameters of a single phase and/or multiphase flow, and more particularly to a probe for measuring the speed of sound and/or vortical disturbances propagating in a single phase fluid flow and/or multiphase mixture to determine parameters, such as mixture quality, particle size, vapor/mass ratio, liquid/vapor ratio, mass flow rate, enthalpy and volumetric flow rate of the flow in a pipe or unconfined space, for example, using acoustic and/or dynamic pressures.

BACKGROUND ART

In the exhaust of a LPT turbine, the quality of the steam has a significant impact on the efficiency of the turbine. If the steam is too dry, excess energy remains in the steam before it hits the condenser. If the steam is too wet, the excess liquid particles can damage the turbine and degrade the aerodynamics. Typically, the exhaust steam from an LPT turbine is nominally approx. 90% quality, or 10% wetness. It would be advantageous to provide a probe to enable the measurement of the steam quality of LPT turbines.

This invention provides an apparatus and method to measure saturated vapor/liquid mixtures used in industrial systems having various working fluids.

Note that once the quality and pressure (or temperature) of a saturated mixture is defined, the thermodynamic properties of the mixture are defined through mixing laws provided the properties of the liquid and vapor sates are known. For example, measuring speed of sound enables one to determine quality, which in turn enables one to calculate enthalpy, density, and other properties of the mixture. In addition to measuring the specific enthalpy, a measurement of the total mass is also, in general, required to determine the flux of enthalpy.

The knowledge or determination of the different parameters of a process flow comprising a saturated vapor/liquid flow is used to provide feedback of the process to improve quality control of a process or detect problems or needed maintenance of the processing system. One such parameter of the vapor/liquid flow is vapor quality (e.g., steam quality) and "wetness" of the mixture. Vapor quality of a saturated vapor/liquid mixture is defined as the ratio of the mass of the vapor phase to the total mass of the mixture. Conversely, the "wetness" of a saturated vapor/liquid mixture is defined as the ratio of the mass of the liquid phase to the total mass of the mixture.

Saturated mixtures exist at temperatures and pressures at which liquid and vapor phases coexist. The temperatures and pressures at which the liquid and vapor phases coexist lie under the "vapor bubble" (i.e., saturation lines) on a phase diagram. A representative phase diagram for water is shown in FIG. 1. The collection of points known as the saturated liquid line and the collections of points known as the saturated vapor line define the vapor bubble. These two lines connect at, what is termed, the critical point. Saturated mixtures exist only under the vapor bubble. For pressures and temperatures outside of the vapor bubble, the fluid exists as a single phase and the properties of that fluid, such as density, enthalpy, internal energy, etc., are uniquely defined by the pressure and temperature. For common fluids, such as water, these properties are tabulated as functions of pressure and temperatures and are available through a variety of references including a website hosted by NIST (ref: http://webbook.nist.gov/chemistry/fluid/).

For fluids at pressures and temperatures that lie within the vapor bubble, the fluids represent mixtures of the liquid and vapor phase. Although the properties of both the vapor and liquid phases are well defined (and tabulated for known substances), the properties of the mixture are no longer uniquely defined as functions of pressure and temperature. In order to define the averaged properties of a saturated mixture, the ratio of the vapor and liquid components of the mixture must be defined. The quality of the mixture, in addition to the pressure and temperature, are defined and used to uniquely determine the properties of the mixture.

Measuring the average properties of a mixture is important in many industrial application since it is the mass averaged properties of the working fluid that enter directly into monitoring the thermodynamic performance of many processes. For example, it is the difference in the flux of enthalpy of the steam mixture flowing into and exiting from a turbine that determines the maximum mechanical work that can be extracted from the working fluid, and thus is important to determine component efficiency. However, if the steam entering or exiting the turbine were saturated, pressure and temperature measurement would not be sufficient to determine the specific enthalpy, but rather, a measurement of the quality of the steam would be required to uniquely define the thermodynamic properties of the saturated steam mixture. Note that once the quality and pressure (or temperature) of a saturated mixture is defined, the thermodynamic properties of the mixture are defined through mixing laws provided the properties of the liquid and vapor sates are known.

The present invention provides the means for measuring the speed of sound enables one to determine quality, which in turn enables one to calculate enthalpy, density, and other properties of the mixture. In addition to measuring the specific enthalpy, a measurement of the total mass is also, in general, needed to determine the flux of enthalpy.

There are many other situations where knowing the quality of a saturated mixture is beneficial. For example, in a steam power plant, the quality of the steam within the steam turbine affects blade life. Generally it is desired to operate so the quality is as high as possible throughout the turbine to minimize liquid water drops that will erode the metal blades. Knowing the quality at the turbine inlet and exhaust (or at the exhaust only if the inlet is super-heated) provides a means to monitor the quality throughout the turbine. Also, to monitor plant performance so that it can be operated at optimum conditions and to identify degradation effects, the steam turbine thermal performance must be known. This requires the fluid enthalpy at the inlet and exhaust of each turbine to be known. If the fluid at either or both locations is saturated, pressure and temperature measurements alone will not be enough to determine the enthalpy. However if an additional measurement of quality is made the enthalpy is then defined. In addition, there may be other applications in refrigeration cycles.

The ability to measure the flow rate and composition of the saturated vapor/liquid mixtures within the conduits is an important aspect of any system or strategy design to optimize the performance of a system based on saturated vapor/liquid mixtures. The industry recognizes this, and has been developing a wide variety of technologies to perform this measurement. These include probe based devices, sampling devices, venturis and ultrasonic devices

SUMMARY OF THE INVENTION

Objects of the present invention include providing a probe for measuring the speed of sound and/or vortical disturbances propagating in a single phase fluid flow and/or multiphase mixture to determine parameters of the flow in a confined (e.g. pipe, duct) or unconfined space, for example, using acoustic and/or dynamic pressures. According to the present invention, a probe for measuring at least one parameter of a fluid flow and/or mixture flowing through an axial bore includes a spatial array of at least two pressure sensors, disposed at different axial locations along the axial bore. Each pressure sensor measures an unsteady pressure within the bore at a corresponding axial location. Each of the sensors provides a pressure signal indicative of the unsteady pressure within the bore at said axial location of a corresponding one of said sensors. A signal processor, responsive to said pressure signals, provides a signal indicative of the at least one parameter of the fluid flow and/or mixture flowing through the axial bore.

According to the present invention, a probe for measuring the speed of sound propagating through a fluid flow and/or mixture flowing through an axial bore includes an acoustical source that generating sound and a resonant condition in the bore. A pressure sensor generates pressure signals indicative of the resonant condition in the bore. A signal processor, responsive to said pressure signals, provides a signal indicative of the speed of sound propagating through the fluid flow and/or mixture passing through the axial bore.

The foregoing and other objects, features and advantages of the present invention will become more apparent in light of the following detailed description of exemplary embodiments thereof.

BRIEF DESCRIPTION OF THE DRAWINGS

FIG. 3 is a perspective view of a probe in accordance with the present invention.

FIG. 7 is a cross-sectional view of a probe in accordance with the present invention.

FIG. 8 is a side elevational view of the pipe and pressure sensors of a steam probe in accordance with the present invention.

FIG. 9 is a cross-sectional view of a piezoelectric film sensor in accordance with the present invention.

FIG. 10 is a top plan view of a piezoelectric film sensor in accordance with the present invention.

FIGS. 13-16 are views of the body of another embodiment of the probe of FIG. 12, in accordance with the present invention.

FIGS. 17-19 are views of the end caps of probe of FIG. 12-22 in accordance with the present invention.

FIGS. 20-22 are k-ω plots of data taken during testing of the probe of FIG. 12 in a wind tunnel.

BEST MODE FOR CARRYING OUT THE INVENTION

Figure 2:
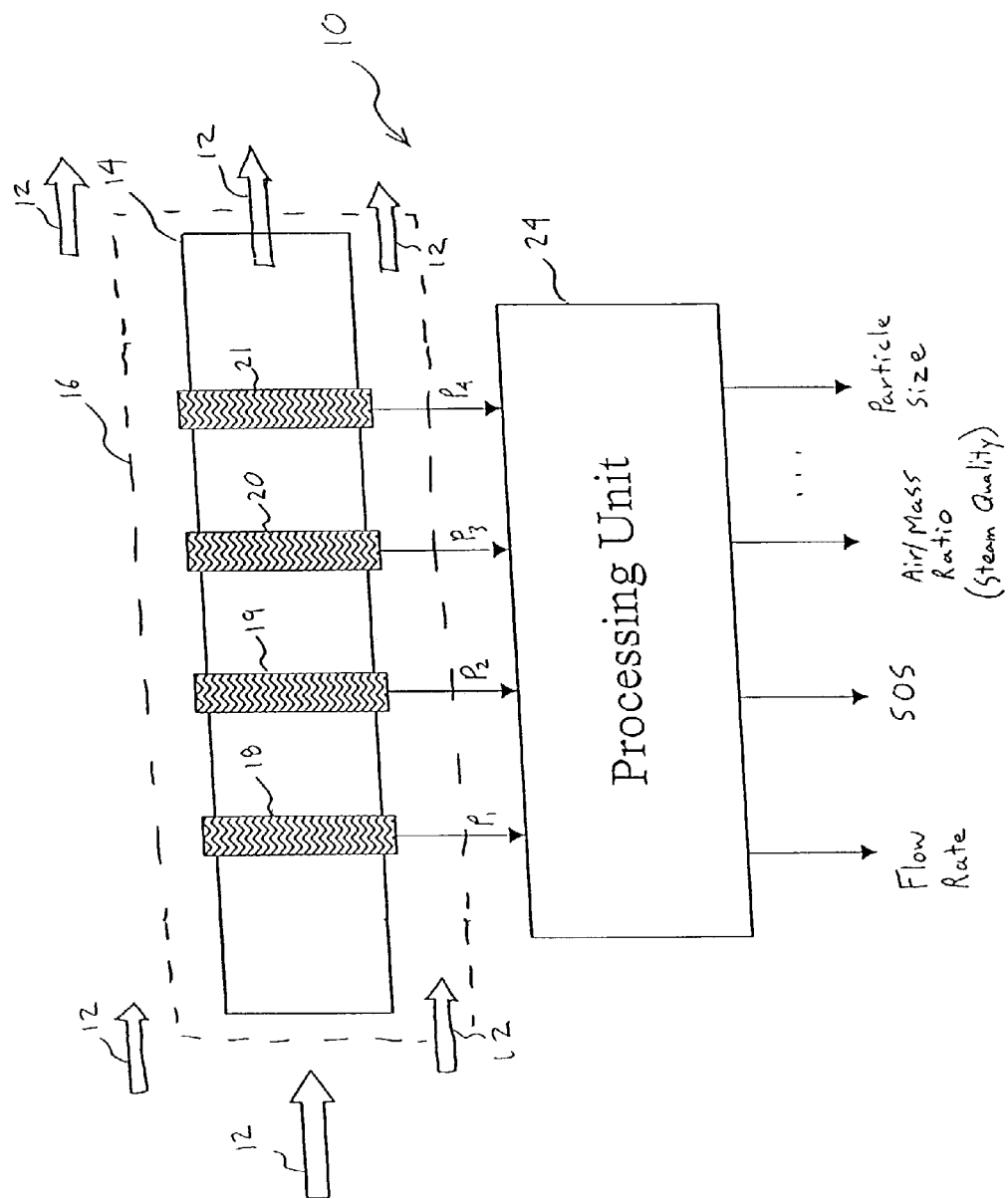
FIG. 2 is a schematic illustration of a probe in accordance with the present invention.

Referring to FIGS. 2 and 3, a probe, generally shown as 10, is provided to sense and determine specific characteristics or parameters of a single phase fluid 12 and/or a multi-phase mixture 12 flowing through a pipe (conduit) or in an unconfined space. The multi-phase mixture may be a two-phase liquid/vapor mixture, a solid/vapor mixture or a solid/liquid mixture, or even a three-phase mixture. One example of a multiphase mixture that can be measured is a saturated vapor/liquid mixture, such as steam. To simplify the description of the present invention, the probe 10 will be described as an apparatus for measuring the parameters of a steam mixture, however, one will appreciate that the probe may be used to measure specific characteristics of any single phase fluid (i.e. vapor or liquid) or any multiphase mixture. As will be described in greater detail, the probe measures the speed of sound propagating through the fluid or multiphase mixture flow to determine any one of a plurality of parameters of the flow, such as the steam quality or "wetness", vapor/mass ratio, liquid/solid ratio, the volumetric flow rate, the mass flow rate, the size of the suspended particles, and the enthalpy of the flow. Additionally, the probe '0 is capable of measuring the unsteady pressure disturbances (e.g., vortical effects, density changes) of the flow passing through the probe to determine the volumetric flow rate of the flow.

FIG. 2 illustrates a schematic drawing of the probe 10 that includes a sensing device 16 comprising an inner tube 14 and an array of pressure sensors (or transducers) 18-21 spaced axially along the outer surface 22 of the tube 14. The pressure sensors measure the unsteady pressures produced by acoustical and/or vortical disturbances within the tube, which are indicative of a parameter of the single phase fluid or multiphase mixture 12. The output signals ($P_1$-$P_4$) of the pressure sensors 18-21 are provided to a processing unit 24, which processes the pressure measurement data and determines at least one parameter of the mixture. Specifically, the characteristics and parameters determined may include the volumetric flow of the flow, the consistency or composition of the flow, the density of the mixture, the Mach number of the flow, the size of particle flowing through the mixture, the air/mass ratio of the mixture and/or the percentage of entrained air within the mixture.

In an embodiment of the present invention shown in FIG. 2, the probe 10 has four pressure sensors 18-21 disposed axially along the tube 14 for measuring the unsteady pressure $P_1$-$P_4$ of the fluid or mixture 12 flowing therethrough. The probe 10 has the ability to measure the volumetric flow rate and other flow parameters using one or both of the following techniques described herein below:

1) Determining the speed of sound of acoustical disturbances or sound waves propagating through the flow 12 using the array of pressure sensors 18-21, and/or 2) Determining the velocity of vortical disturbances or "eddies" propagating through the flow 12 using the array of pressure sensors 18-21.

Generally, the first technique measures unsteady pressures created by acoustical disturbances propagating through the flow 12 to determine the speed of sound (SOS) propagating through the flow. Knowing the pressure and/or temperature of the flow and the speed of sound of the acoustical disturbances, the processing unit 24 can determine the mass flow rate, the consistency of the mixture (i.e., the mass/air ratio, the mass/liquid ratio, the liquid/air ratio), the volumetric flow rate, the density of the mixture, the enthalpy of the mixture, the Mach number of the mixture, the size of the particles within the mixture, and other parameters, which will be described in greater detail hereinafter. For steam, the first technique of measuring the speed of sound can determine flow parameters, such as the volumetric flow rate, steam quality, steam wetness and the size of the droplets of water.

Figure 34:
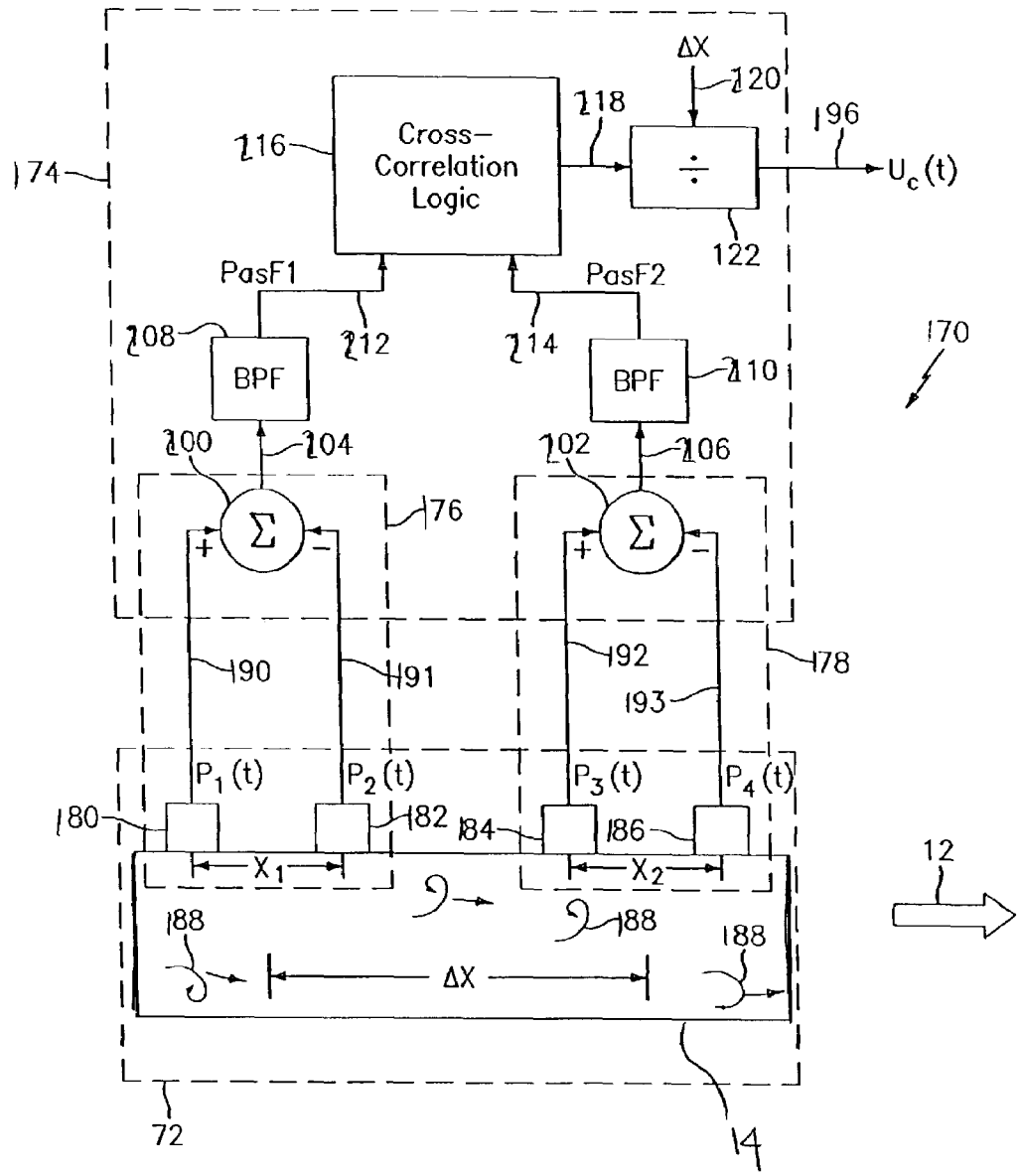
FIG. 34 is a block diagram of a probe for measuring the vortical field of a saturated vapor/liquid mixture flowing within a pipe, in accordance with the present invention.

The second technique measures the velocities associated with unsteady flow fields and/or pressure disturbances created by vortical disturbances or "eddies" to determine the velocity of the flow 12. The pressure sensors 18-21 measure the unsteady pressures $P_1$-$P_4$ created by the vortical disturbances as these disturbances convect within the flow 12 through the probe 10 in a known manner, as shown in FIG. 34. Therefore, the velocity of these vortical disturbances is related to the velocity of the mixture and hence the volumetric flow rate may be determined, as will be described in greater detail hereinafter.

Figure 4A:
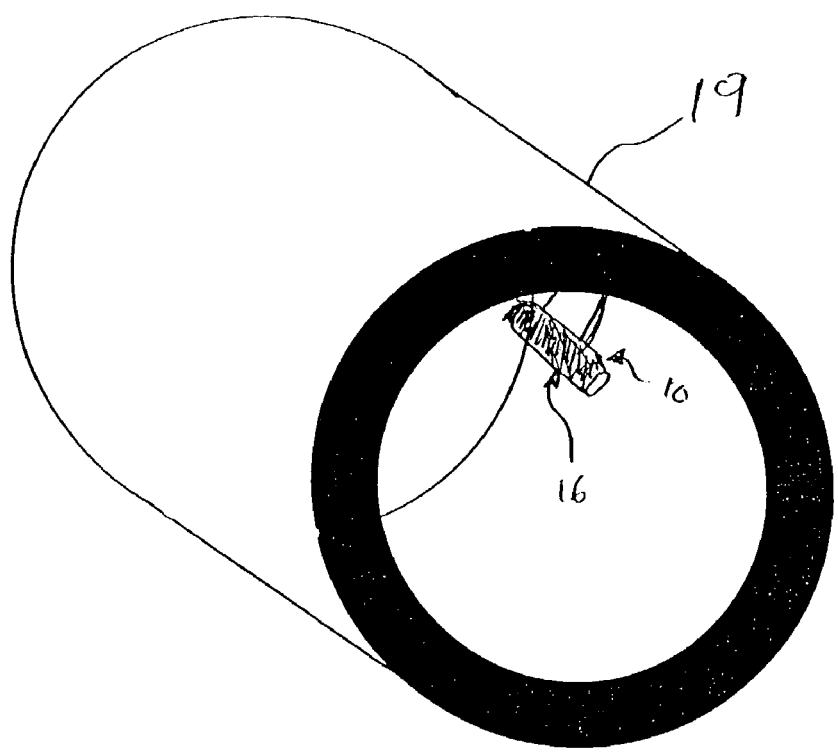
FIG. 4a is a perspective view of a probe embodying the present invention mounted within a pipe having circular cross-section in accordance with the present invention.
Figure 4B:
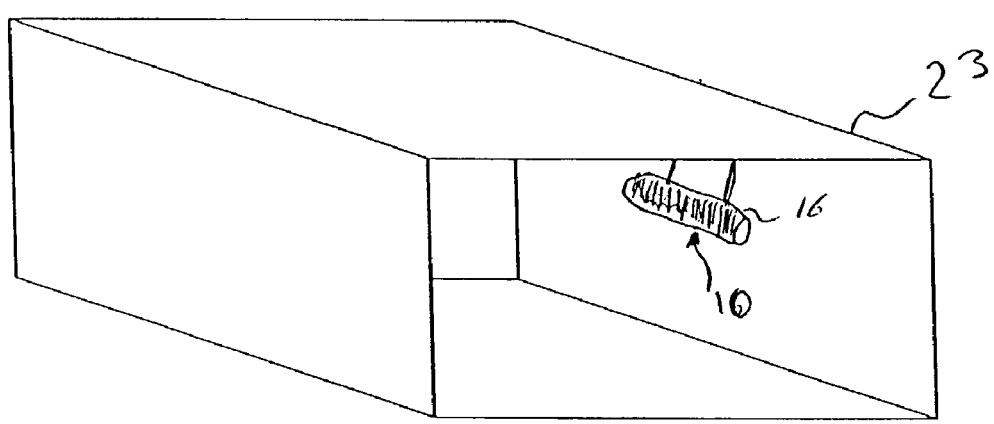
FIG. 4b is a perspective view of a probe embodying the present invention mounted within a duct having rectangular cross-section in accordance with the present invention.
Figure 5:
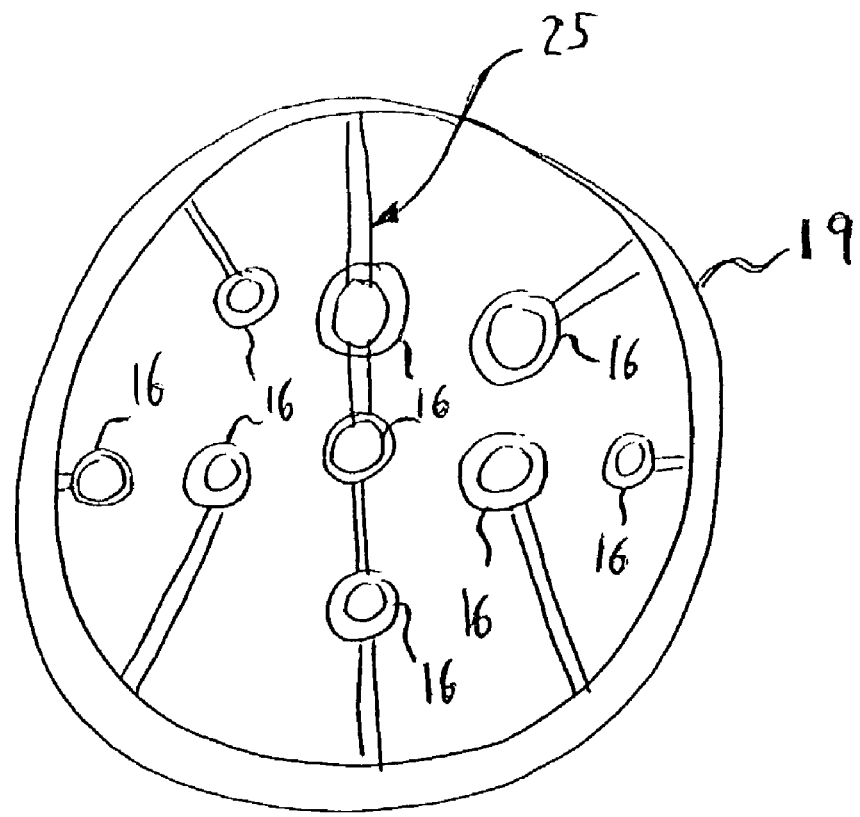
FIG. 5 is a cross-sectional view of a plurality of probes disposed within a pipe for characterizing the flow pattern of the flow passing through the pipe in accordance with the present invention.

The probe 10 may be used a number of different ways. For example as shown in FIGS. 4a and 4b, the sensing device 16 of the probe may be mounted within a pipe 19 or duct 23, respective to measure the fluid flow or mixture passing therethrough. The probe 10 is particularly useful for large diameter pipes or ducts having a large cross-sectional area, such as smokestacks, exhaust ducts or HVAC systems. The utility of the probe is especially evident for measuring the flow of a single phase fluid or multiphase mixture 12 that is not confined within piping or ducting. For example, the probe may be mounted within a gas turbine to measure the steam "wetness" or other parameters of the steam exiting the exhaust duct of the steam or LPT turbine. Other applications or uses of the sensing device 16 of the probe 10 include mounting the probe to the exterior of a vehicle such as an automobile, airplane and a train to measure parameters of the air or velocity of the vehicle. Further, the probe may be mounted to the bottom of a ship to measure the SOS propagating through the probe, or mounted to the outer hull of a submarine to measure the speed of sound at different depths in the ocean, as well as other parameters. Generally, the probe may be used in any application that one may use a pitot-static probe. The probe may also be used to measure parameters of a river flow, an open conduit or partially filled pipe.

Figure 6:
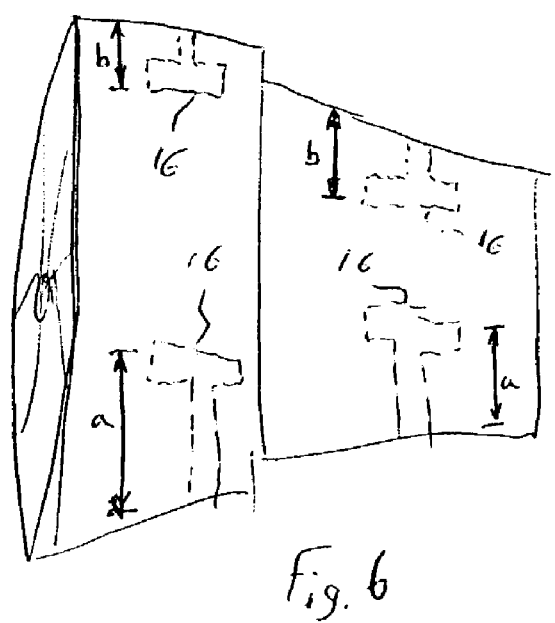
FIG. 6 is a side view of a steam turbine having a plurality of probes disposed at different stages of the turbine and a different depths within each stage in accordance with the present invention.

The probe 10 is particularly useful in characterizing the pattern of the flow 12 within a confined space (e.g., a pipe 19, duct 21) or unconfined space. For example as shown in FIG. 6, one or more sensing devices 16 of respective probes may be disposed at different locations across the area of the flow 12. The data provided by each of the probes and the known location of the probe enables one to characterize the flow pattern. For example, one probe may be disposed adjacent to the wall of a pipe 19 and another probe may be disposed at a central position within the pipe to characterize the velocity and vapor/mass (e.g. steam wetness) at the two locations. One will appreciate that any number of sensing devices 16 may be disposed at number of locations within the flow.

The invention also contemplates a probe having a plurality or array of interconnected sensing devices 16 at 25 that extends across the flow 12 in a single plane or disposed in different planes of the flow. In other words, the sensing devices 16 of the probes 10 may be disposed at different locations along the flow 12. For example as shown in FIG. 6, probes may be disposed at different stages of a gas steam turbine at different locations at each stage. The probe may be used to measure the steam wetness at each stage at different location or depth from the walls of the turbine within each stage to measure the efficiency of the turbine or aid with the design of the turbine. The probes may also be used to troubleshoot or design jet engines in a similar fashion.

A plurality of probes may also be mounted in an unconfined area to provide parameters of the flow pattern across the area, such as open fields, mountain tops, rivers and oceans. The probes could function to provide certain meteorological data.

Referring to FIGS. 2, 3 and 7, in one embodiment of the present invention, the sensing device 16 of the probe 10 includes an inner tube 14 disposed within a tubular, outer housing 50 to provide an input port 53 and output port 55 for the flow 12 to pass through. The inner tube is generally cylindrical in shape having an axial bore 57 with a circular cross-section. The invention, however, contemplates that the inner tube may be of any shape or cross-sectional shape, such as squares, oval rectangular or any other polygonal shape. The cross-sectional shape may even be different along the length of the inner tube. The outer diameter of the inner tube is approximately one inch, but the diameter may be of any length. However, one must appreciate that the larger the diameter of the tube 16 the longer the array of sensors 18-21 must be to measure the SOS of the mixture.

A pair of end caps 52,54 is disposed at the respective ends of the inner tube 14 and outer housing 50 to maintain and support the tube coaxially within the housing. The housing protects the array of sensors 18-21 disposed along the tube from the flow 12, and also acts as an insulator or isolator to prevent external acoustic and/or unsteady pressure disturbances from affecting the sensors 18-21. The end caps have a central bore 56 with a inner diameter substantially the same as the inner diameter of the tube 14. The outer surface 58 of the end caps are tapered and the outer ends 60 are rounded to provide an aerodynamic profile to reduce the drag of the flow (e.g., steam) over the probe 10 to reduce the wind resistance and stresses thereon. The aerodynamic profile also reduces the disturbance of the flow of the fluid or mixture. The aerodynamic characteristics are particularly important for high speed steam flow (e.g., 0.7 Mach), such as steam exiting a gas turbine exhaust.

While the sensing device 16 has a pair of end caps 52,54 as shown best in FIG. 7, the invention completes a sensing device 16 having no discrete end caps and that the inner tube 14 extends the length of sensing device of the probe 10.

While the inner tube 14 of the sensing device 16 of the probe 10 is shown to have a substantially axial bore 57 therethrough, the invention contemplates that the bore may be non-axial, such as having a bend in the tube. Of course, such a non-axial bore would increase the drag of the sensing device 16 within the flow 12. While in most instances it is not necessary, the invention also contemplates providing ridges 59 at the input end of the tube 14 to create vortical disturbances to be measured. These ridges can be formed by grinding circumferential grooves in the inner wall of the tube or providing circumferential ridges extending from the wall.

The invention also contemplates providing one or more acoustic sources 61 to enable the measurement of the speed of sound propagating through the flow for instances of acoustically quiet flow. The acoustic sources may be disposed at the input end of output end of the probe, or at both ends as shown. One should appreciate that in most instances the acoustics sources are not necessary and the probe passively detects the acoustic ridge provided in the flow 12.

The embodiment of the sensing device 16 shows a single input and output port 53,55, however, the invention contemplates that the sensing device may have a plurality of input ports and/or output ports that feed into and out of the central portion of the tube 14 where the sensors array 18-21 are disposed. While contemplated, one will appreciate that additional drag may be place upon the sensing device 16 and additional disturbance to the flow 12.

The sensing device 16 of the probe 10 further includes a fin-shaped support structure 62 extending from the center of the housing 50 for mounting the sensing device to a wall or other support, as shown in FIGS. 3-6. The support structure 62 includes a bore 64, disposed therethrough to communicate with the space 66 disposed between the tube 14 and the housing 50. The bore 64 provides a means to run the conductors of the pressure sensors 18-21 to the processing unit 24, as best shown in FIG. 2. The support structure 62 is oriented to reduce wind resistance to minimize disturbance of the steam flow.

Similar to that described in U.S. patent application Ser. No. PCT/US00/17419, which is incorporated herein by reference, the space 66 between the tube 14 and the housing 50 may be evacuated to provide "vacuum backed" sensors 18-21. Evacuating the space 66 provides additional insulation/isolation to prevent external acoustic and/or unsteady pressure disturbances from affecting the sensors 18-21.

In one embodiment of the present invention as shown in FIG. 2, each of the pressure sensors 18-21 may include a piezoelectric sensor or piezoelectric film sensor 30 as shown in FIGS. 8-10 to measure the unsteady pressures of the mixture 12 using either technique described hereinbefore. FIG. 8 shows a more detail embodiment of the piezoelectric film sensors 30 wrapped around the outer wall of the tube 14 of the sensing device 16. In this embodiment the array of sensors includes seven sensors 30 spaced approximately 7/8 inches apart, where the first sensor is disposed approximately 1 3/8 inches for the input end. The length of the inner tube is approximately 8 inches and has an inner diameter of approximately one inch.

As best shown in FIGS. 9 and 10, the piezoelectric sensors 30 include a piezoelectric material or film 32 to generate an electrical signal proportional to the degree that the material is mechanically deformed or stressed. The piezoelectric sensing element is typically conformed to allow complete or nearly complete circumferential measurement of induced strain. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the inner tube 14 due to unsteady pressure variations (e.g., vortical and/or acoustical) within the process mixture 12. Strain within the tube is transduced to an output voltage or current by the attached piezoelectric sensor. The piezoelectrical material or film may be formed of a polymer, such as polarized fluoropolymer, polyvinylidene fluoride (PVDF).

Figure 1:
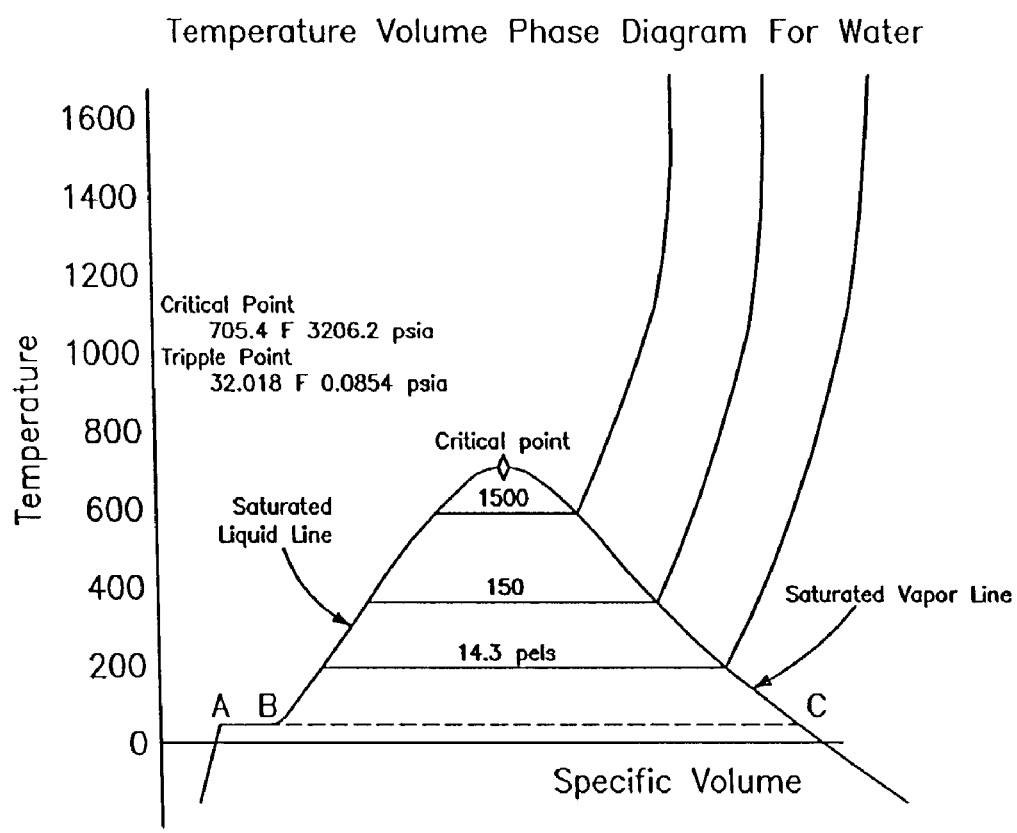
FIG. 1 is a representative phase diagram for water.

FIGS. 9 and 10 illustrate a piezoelectric film sensor (similar to the sensor 18 of FIG. 1), wherein the piezoelectric film 32 is disposed between and pair of conductive coatings 34,35, such as silver ink. The piezoelectric film 32 and conductive coatings 34,35 are coated onto a protective sheet 36 (e.g., mylar) with a protective coating 38 disposed on the opposing side of the upper conductive coating. A pair of conductors 40,42 is attached to a respective conductive coating 34,35.

The thickness of the piezoelectric film 32 may be in the range of 20 um to approximately 100 um. The thickness is the dependent on the degree of sensitivity desired or needed to measure the unsteady pressures within the inner tube 14 of the probe 10. The sensitivity of the sensor 30 increases as the thickness of the piezoelectric film increases.

The advantages of this technique wrapping or clamping the PVDF sensor 30 onto the outer surface of the tube 14 are the following:

1. Non-intrusive flow rate measurements
2. Low cost
3. Measurement technique requires no excitation source. Ambient flow noise is used as a source.
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vortical noise detection, d) tailored sensor geometries to minimize sensitivity to tube modes, e) differencing of sensors to eliminate acoustic noise from vortical signals.
5. Higher Temperatures (140C.) (co-polymers)

Figure 11:
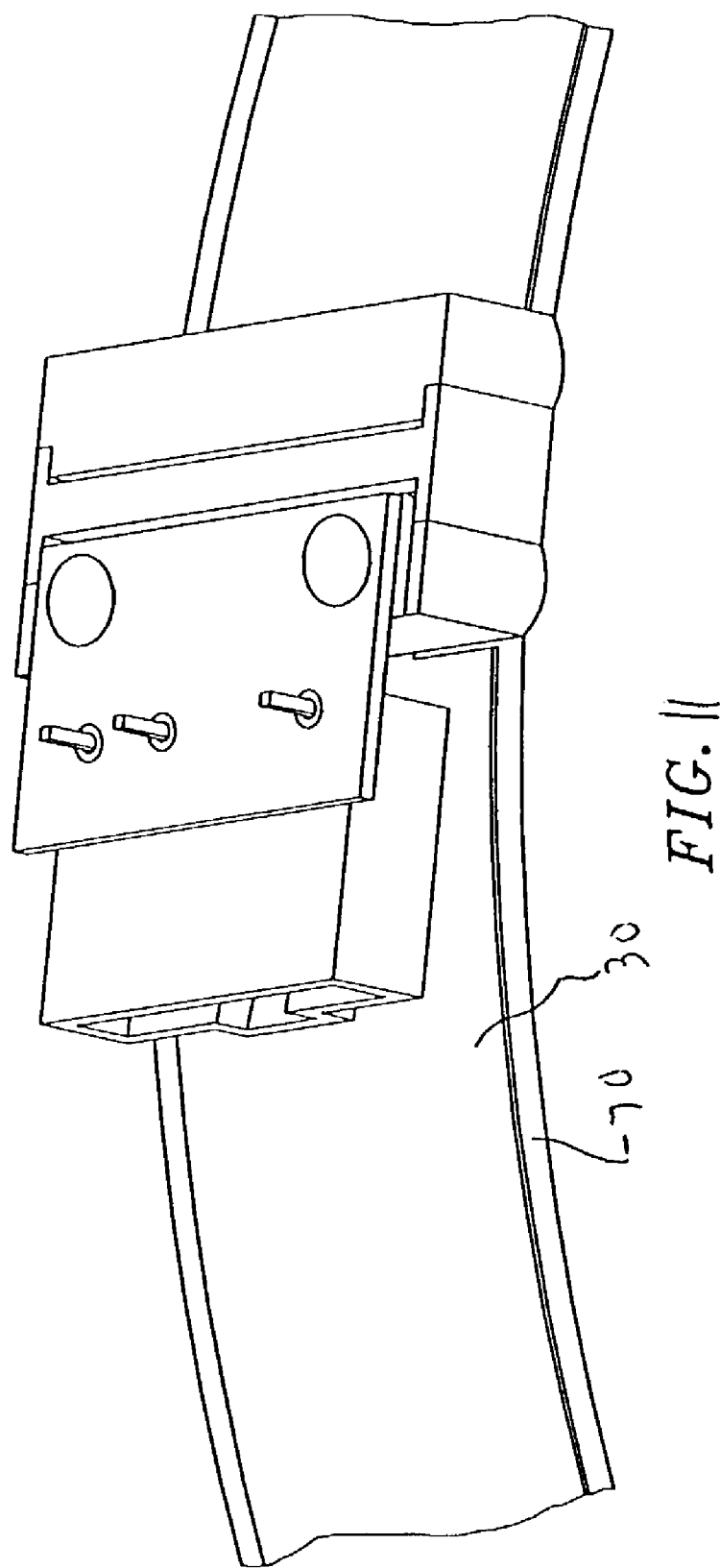
FIG. 11 is a side elevational view of a plurality of pressure sensors, having PVDF, clamped to the outer surface of the pipe, in accordance with the present invention.

The piezoelectric film sensors may be mounted directly onto the outer diameter of the tube 14 by epoxy, glue or other adhesive. Alternatively, the piezoelectric film sensors 30 may be adhered to a strap 70 which is then clamped onto the outer surface of the tube 14, as shown in FIG. 11, similar to that described in U.S. Provisional Application No. 60/426, 724.

FIGS. 12-19 show another embodiment of sensing device 16 of the steam probe 10 described hereinbefore, wherein the pressure sensors 18-21 are of the type described hereinafter, such as part number PCB 106M74 ICB microphone, manufactured by PCB Piezotronics, Inc. As shown, the body 80 of the sensing device 16 (see FIGS. 13-16) includes the support structure 82 and the tube portion 94. The body of the probe is a unitary part. The tube portion 84 has a square bore 96 extending axially therethrough for receiving the fluid or mixture 12. The ends of the tube portion include respective counterbores 90 for receiving the ends caps 92 (see FIGS. 17-19). The end caps 92 have an axial bore 91 having a circular cross-section at one end and transitions to a square cross-section at the other end to match the bore 86 of the tube portion 84. A plurality of mounting bores 94 extends radially from the through-bore 86 through the support structure for mounting the pressure sensors 98 (see FIG. 12) therein. The mounting bores 94 extend through to the square through-bore 86 so that the ends of the pressure sensors come into direct contact with fluid or mixture 12 passing through the tube portion 84. The ends of the pressure sensors set flush with the surface of the walls of the through-bore 86 to prevent disturbance of the flow of the mixture. As described hereinbefore, the tube portion 84 may have any cross-sectional shape.

Steam driven turbines are a major source of electrical power world wide. At present, there are no real time, operationally effective methods to monitor the quality of the steam as it drives the generators. Ideally, the industry would like to extract the maximum amount of energy from the steam as it passes through the turbine system thus reducing it to water; however, as water droplets form from the steam, they induce erosion and wear in the turbine blades requiring expensive maintenance. Thus a balance between the energy extracted from and the amount of water entrained in the steam must be met.

Standard temperature and pressure cannot uniquely determine the wetness, i.e. the amount of water in the steam, when both phases coexist. The present invention uses speed of sound measurements to determine wetness of saturated steam using dispersion calculations. In non-nuclear power generation plants, the steam is super heated, and thus comprises only one phase, for each process step except the Low Pressure (LP) Turbine Exhaust. At this exhaust, the wet steam is traveling at speeds in the range 0.5 to 0.7 Mach (Ma).

The probe 10 embodying the present invention is capable of measuring the dispersion of the speed of sound of the steam at the exhaust of the Low Pressure Turbine to determine the wetness and water droplet size can be determined. The speed of sound at low frequencies, i.e. less than approximately 1 kHz will indicate the wetness of the steam; the curvature of the dispersion of the speed of sound from approximately 1 kHz to 20 kHz is dictated by the size of the water particles for this application. The probe was tested in a wind tunnel at Mach numbers of 0.3 to 0.64 Ma and angles of attack of 0 to 10 degrees to evaluate the ability of the probe to derive the speed of sound and bulk velocity.

Figure 12:
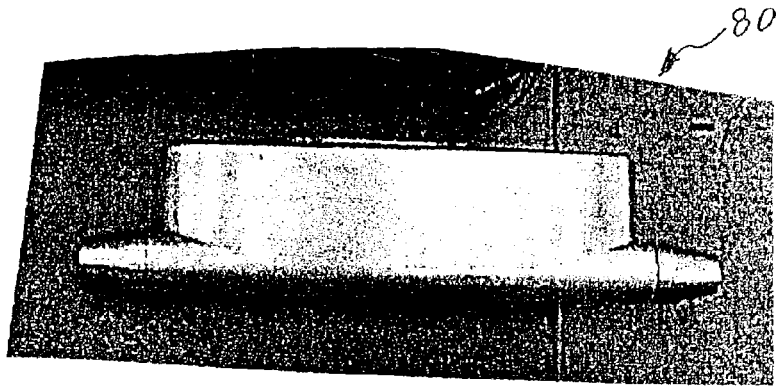
FIG. 12 is a side view of another embodiment of a probe, having ported pressure sensors, in accordance with the present invention.

The probe tested in the wind tunnel was 19 inch long, 2 inch outer diameter hollow cylinder with a 1.75 inch wide sail attached to one side (See FIG. 12). The two inch diameter cylinder was coned at each end and had circular foot print for the inner diameter at both entrance and exit. The circular inner diameter transitioned to a square profile over a three inch length (for both ends) maintaining a constant cross sectional area though out the length. Ten pressure sensors were housed in the sail at 1.25 inch spacing. The location of the sensors was along the 13 inch long central square profile section. A mounting plate was attached to the sail with through holes for the electrical cables allowing the probe to be installed in the wind tunnel.

Two eight channel signal conditioners converted the pressure sensor outputs to voltages that were passed to Krohnhite low pass filters. The filtered signals were sampled by an ADC and a standard MatLab processing engine used to store and process the data. Additionally, the temperatures and pressures were recorded along the wind tunnel at multiple locations.

The inner diameter of the end caps was 1.111 inch diameter at each end and the square bore had a 1 inch square cross section with 0.188 inch radius corners. The inner diameter transitioned from round to square to round with constant area. The sail was 1.75 inch wide by 3.5 inch edge to tube center line. The sensing device 16 was formed of aluminum alloy 6061 T6. The pressure sensors were PCB 106M74 ICP Microphones.

Figure 20:
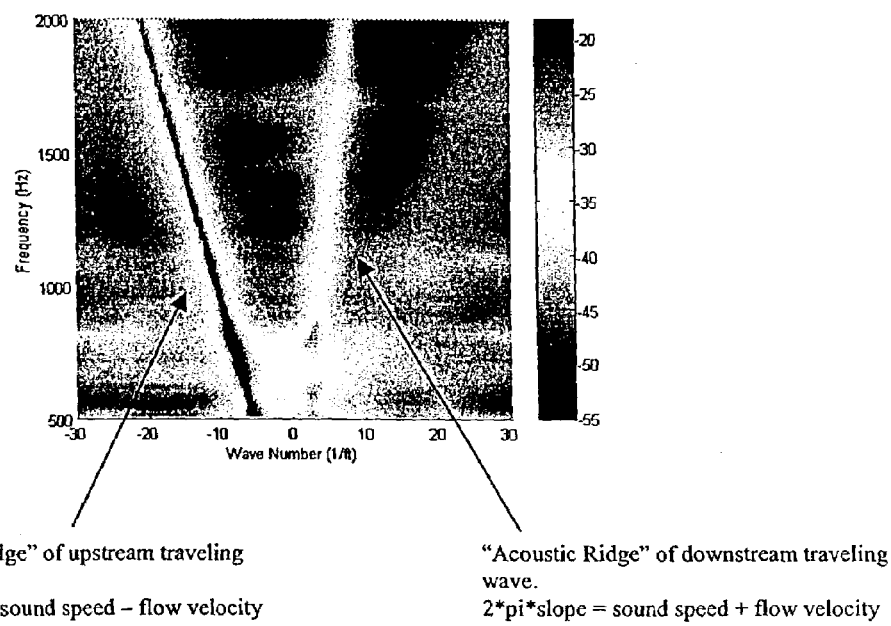

The acoustic reflection coefficients of the inlet and outlet of the probe were reduced for high Mach numbers. FIG. 20 shows the k-ω plot for 0.5 Ma at 0 degrees angle of attack. Note that both the right and left acoustic ridges are readily visible. In FIG. 21, the bulk velocity has been increased to 0.6 Ma and the right acoustic ridge has nearly disappeared. FIG. 22 is the k-ω plot for 0.5 Ma with an angle of attack of 10 degrees. Note the misalignment of the probe to the air flow has generated enough vortical disturbances to bring the velocity ridge to a level comparable to that of the acoustic ridges.

Several points merit discussion from this test. First, the k-ω plots for high degree angle of attack conditions demonstrate the high level of turbulent flow in the probe. Even under these conditions, the processing was able to extract the speed of sound and bulk velocity from the unsteady pressure measurements. This seems to be analogous to what would be expected for a meter placed near to and down stream of an elbow in conduit flow.

In ten of the eleven conditions tested, the agreement between the calculated speed of sound values and the probes measurement matched to better than 1%, eight of them better than 0.5%. On the eleventh condition, 0.64 Mach and 10 degree angle of attack, the measured value is 12% lower than the calculated value. The aerodynamics of the wind tunnel did not allow for an accurate reference measurement of the bulk velocity of the air flow (the size of the probe was too large for this test facility and caused blockage) and discrepancies of 40% found.

The wind tunnel test demonstrated that fundamental technology of the present invention is capable of determining both the speed of sound and bulk velocity of air traveling at speeds up to 0.64 Mach.

Figure 23:
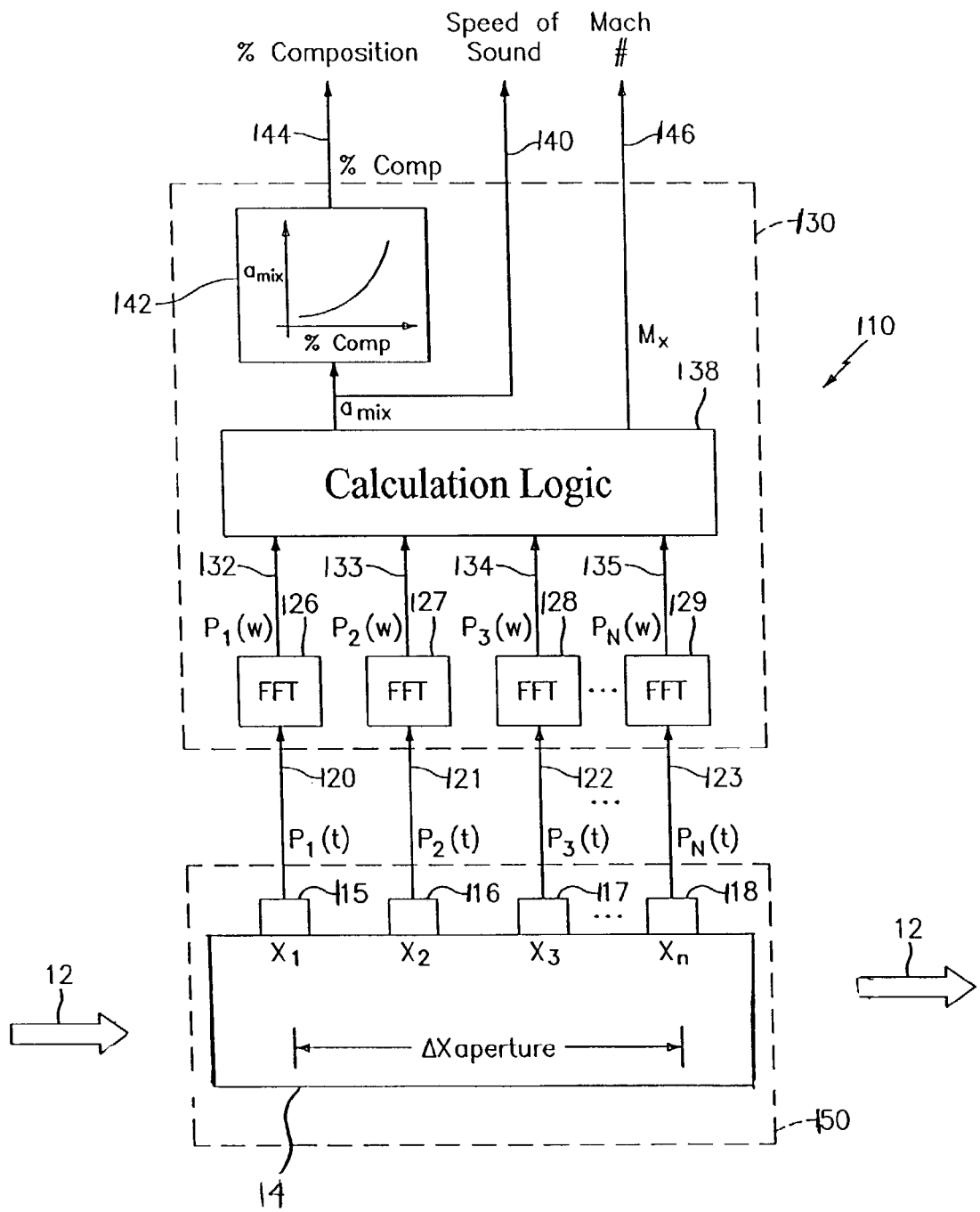
FIG. 23 is a block diagram of a probe for measuring the speed of sound propagating through a saturated vapor/liquid mixture flowing within a pipe, in accordance with the present invention.

Referring to FIGS. 23 and 34, a probe 10,170 embodying the present invention is provided that measures at least one parameter/characteristic of a single phase flow and/or multiphase mixture 12 such as a saturated vapor/liquid mixture 12 of liquid droplets suspended within a continuous vapor/gas, for example, flowing within a pipe 19, duct 21 or flowing unconfined (see FIGS. 3-6). The probe may be configured and programmed to measure the speed of sound propagating through the flow 12 or measure the vortical disturbances propagating through the flow 12. In some instances, the probe 10 may be configured to measure both the speed of sound and the vortical disturbances. Depending on the configuration or embodiment, the probe can measure at least one of the following parameters of the flow 12: the wetness or steam quality (volumetric phase fraction), the volumetric flow rate, the size of the liquid particles, the mass flow, the enthalpy and the velocity of the mixture. To determine any one of these parameters, the probe 110,170 measures the unsteady pressures created by the speed of sound (SOS) and/or the vortical disturbances propagating through the single phase fluid or multiphase mixture flowing in the inner tube 14 of the probe 110,170, which will be described in greater detail hereinafter.

The liquid droplets (or solids) of the mixture 12 may be of any size, shape and liquid. For example, the size of the droplets may be as small as <0.3 microns in length (or diameter) to greater than 50 microns. However, the length of the sensing device 16 is dependent on particle size. The larger the particle size is the longer the sensing device of the probe.

The type of unsteady pressure measurement being made determines the spacing of the sensors. Measurement of unsteady vortical pressures require sensors spacing less than the coherence length of the vortical disturbances which is typically on the order of a tube diameter. Correlation of unsteady vortical pressure measurements between sensors is used to determine the bulk flow rate of the process mixture, which will be described in greater detail hereinafter.

Mass flow rates and other parameters are determined by measuring the speed of sound propagating within the process mixture 12. These parameters are determined by correlating unsteady pressure variations created by acoustic disturbances within the process mixture. In this case, the wavelength of the measured acoustic signal determines the sensor spacing. The desired wavelength of the measured acoustic signal is dependent upon the dispersion of particles in the mixture flow, which is dependent on the particle size, which will be described in greater detail hereinafter The probe 110,170 can be used in any application that carries liquid droplets suspended in a vapor/gas through a pipe, such as in paper/pulp, petroleum and power generation applications. For example, the present invention is well suited to measure the parameters (e.g. vapor/liquid ratio, particle size) for power generation systems.

As one example, the present invention will be discussed in the context of a steam delivery system for power generation, but one will appreciate that the probe 10 can be applied to any number of other applications, as discussed hereinbefore.

As described hereinbefore, the probe 10,170 of the present invention may be configured and programmed to measure and process the detected unsteady pressures $P_1(t)$-$P_N(t)$ created by acoustic waves and/or vortical disturbances, respectively, propagating through the mixture to determine parameters of the mixture flow 12. One such probe 10 is shown in FIG. 3 that measures the speed of sound (SOS) of one-dimensional sound waves propagating through the vapor/liquid mixture to determine the composition the mixture, namely the "wetness" or steam quality of the mixture. The probe is also capable of determining the average size of the droplets, velocity of the mixture, enthalpy, mass flow, steam quality or wetness, density, and the volumetric flow rate of the mixture. It is known that sound propagates through various mediums at various speeds in such fields as SONAR and RADAR fields. The speed of sound of a mixture within the inner tube 14 may be determined using a number of known techniques, such as those set forth in U.S. patent application Ser. No. 09/344,094, entitled "Fluid Parameter Measurement in Pipes Using Acoustic Pressures", filed Jun. 25, 1999, and U.S. patent application Ser. No. 10/007,749, entitled "Fluid Parameter Measurement in Pipes Using Acoustic Pressures", filed Nov. 7, 2001, each of which are incorporated herein by reference. The present invention utilizes at least one probe 10 to determine various parameters of the saturated vapor/liquid mixture, wherein one of the parameters is the speed at which sound travels within in the flow, as will be more fully described herein below.

In accordance with the present invention, the speed of sound propagating through the vapor/liquid mixture 12 is measured by passively listening to the flow with an array of unsteady pressure sensors to determine the speed at which one-dimensional compression waves propagate through a vapor/liquid mixture contained within the tube 14.

As shown in FIG. 23, the probe 10 has an array of at least three acoustic pressure sensors 115,116,117, located at three locations $x_1,x_2,x_3$ axially along the inner tube 14 or cavity of the probe 110. One will appreciate that the sensor array may include more than three pressure sensors as depicted by pressure sensor 118 at location $x_N$. The pressure generated by the acoustic waves may be measured through holes in the tube 114 ported to external pressure sensors 115-118 or by other techniques discussed herein. The pressure sensors 15-18 provide pressure time-varying signals $P_1(t),P_2(t),P_3(t),P_N(t)$ on lines 120,121,122,123 to a signal processing unit 130 to known Fast Fourier Transform (FFT) logics 126,127, 128,129, respectively. The FFT logics 126-129 calculate the Fourier transform of the time-based input signals $P_1(t)$-$P_N(t)$ and provide complex frequency domain (or frequency based) signals $P_1(\omega),P_2(\omega),P_3(\omega),P_N(\omega)$ on lines 132,133, 134,135 indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter.

The frequency signals $P_1(\omega)$-$P_N(\omega)$ are fed to $a_{mix}$-Mx Calculation Logic 138 which provides a signal to line 40 indicative of the speed of sound of the vapor/liquid mixture $a_{mix}$ (discussed more hereinafter). The $a_{mix}$ signal is provided to map (or equation) logic 142, which converts $a_{mix}$ to a percent composition of the vapor/liquid mixture and provides a % Comp signal to line 44 indicative thereof (as discussed hereinafter). Also, if the Mach number Mx is not negligible and is desired, the calculation logic 40 may also provide a signal Mx to line 46 indicative of the Mach number Mx.

More specifically, for planar one-dimensional acoustic waves in a homogenous mixture, it is known that the acoustic pressure field P(x,t) at a location x along the inner tube 14, where the wavelength λ of the acoustic waves to be measured is long compared to the diameter d of the tube 14 (i.e., λ/d>>1), may be expressed as a superposition of a right traveling wave and a left traveling wave, as follows:

$$P(x,t)=(Ae^{-ik_r x}+Be^{+ik_l x})e^{i\omega t} \quad \text{Eq. 1}$$

where A,B are the frequency-based complex amplitudes of the right and left traveling waves, respectively, x is the pressure measurement location along a tube 14, ω is frequency (in rad/sec, where ω=2πf), and $k_r,k_l$ are wave numbers for the right and left traveling waves, respectively, which are defined as:

$$k_r \equiv \left(\frac{\omega}{a_{mix}}\right)\frac{1}{1+M_x} \quad \text{and} \quad k_l \equiv \left(\frac{\omega}{a_{mix}}\right)\frac{1}{1-M_x} \quad \text{Eq. 2}$$

where $a_{mix}$ is the speed of sound of the mixture in the tube, ω is frequency (in rad/sec), and $M_x$ is the axial Mach number of the flow of the mixture within the tube, where:

$$M_x \equiv \frac{V_{mix}}{a_{mix}} \quad \text{Eq. 3}$$

where Vmix is the axial velocity of the mixture. For non-homogenous mixtures, the axial Mach number represents the average velocity of the mixture and the low frequency acoustic field description remains substantially unaltered.

The data from the array of sensors may be processed in any domain, including the frequency/spatial domain, the temporal/spatial domain, the temporal/wave-number domain or the wave-number/frequency (k-ω) domain. As such, any known array processing technique in any of these or other related domains may be used if desired, similar to the techniques used in the fields of SONAR and RADAR.

Also, some or all of the functions within the signal processing unit 130 may be implemented in software (using a microprocessor or computer) and/or firmware, or may be implemented using analog and/or digital hardware, having sufficient memory, interfaces, and capacity to perform the functions described herein.

Acoustic pressure sensors 115-118 sense acoustic pressure signals that, as measured, are lower frequency (and longer wavelength) signals than those used for ultrasonic probes of the prior art, and thus the current invention is more tolerant to inhomogeneities in the flow, such as time and space domain inhomogeneities within the flow.

In addition, the present invention incorporates the compliance of the inner tube 14 to determine the effective speed of sound of the vapor/liquid mixture flowing through the tube. The acoustic pressure signals $P_1(t)$-$P_N(t)$ are generated within the vapor/liquid mixture of the tube 14 by a variety of non-discrete sources such as remote machinery, mills, pumps, valves, elbows, as well as the vapor/liquid mixture flow itself. It is this last source, the vapor/liquid mixture 12 flowing within the tube 14, which is a generic source of acoustic noise that assures a minimum level of acoustics for any vapor/liquid mixture piping systems for which the present invention takes unique advantage. The flow generated acoustics increase with mean flow velocity and the overall noise levels (acoustic pressure levels) are a function of the generating mechanism and the damping mechanism. As such, no external discrete noise source is required within the present invention and thus may operate using passive listening. While the probe 110 passively listens to the mixture flow 12, the present invention contemplates adding at least one an acoustic source to inject a desire acoustic wave into the flow to be measured, such as by compressing, vibrating and/or tapping the tube, to name a few examples, as shown in FIG. 7.

For certain types of pressure sensors, e.g., pipe strain sensors, accelerometers, velocity sensors or displacement sensors, discussed hereinafter, it may be desirable for the tube 14 to exhibit a certain amount of tube compliance.

Alternatively, to minimize any error effects (and the need for the corresponding calibration) caused by tube compliance, the axial test section 150 of the tube 14 along where the sensors 115-118 are located may be made as rigid as possible. To achieve the desired rigidity, the thickness of the wall of the test section 150 may be made to have a predetermined thickness, or the test section 150 may be made of a very rigid material, e.g., steel, titanium, Kevlar®, ceramic, or other material with a high modulus.

It is within the scope of the present that the pressure sensor spacing may be known or arbitrary and that as few as two sensors are required if certain information is known about the acoustic properties of the vapor/liquid mixture. The pressure sensors are spaced sufficiently such that the entire length of the array (aperture) is at least a significant fraction of the measured wavelength of the acoustic waves being measured. As will be described in greater detail, the acoustic wavelength to be measured is a function of at least the size and mass of the droplets, and the viscosity of the vapor. The greater the size and mass of the droplets and/or the less viscous the vapor, the greater the spacing of the sensors is needed. Conversely, the smaller the size and mass of the droplets and/or the more viscous the vapor, the shorter the spacing of the sensors is needed.

For relatively well-mixed vapor/liquid mixtures in which the liquid phase exists as small droplets within a continuous gas phase, the flow can be termed mist flow. Assuming that the droplets of the vapor/liquid mixture are small enough and the acoustic frequencies and the frequencies of perturbations associated with the acoustics are low enough for the droplets of liquid to exhibit negligible slip (both steady and unsteady), the sound speed can be assumed to be substantially non-dispersive (that is constant with frequency) and the volumetric phase fraction of the mixture could be determined through the Wood equation:

$$\rho_{mix} = \sum_{i=1}^{N} \phi_i \rho_i$$

$$\frac{1}{\rho_{mix} a_{mix}^2} = \sum_{i=1}^{N} \frac{\phi_i}{\rho_i a_i^2}$$

$$\sum_{i=1}^{N} \phi_i = 1$$

For one-dimensional waves propagating within a vacuum backed tube 14 (or a tube immersed in large volume of low impedance fluid such as air at atmospheric conditions), the compliance introduced by the tube (in this case a circular tube of modulus E, radius R and wall thickness t) reduces the measured sound speed from the infinite dimensional sound speed. The effect of the conduit is given by the following relationship:

$$\frac{1}{\rho_{mix} c_{measured}^2} = \frac{1}{\rho_{mix} c_{mix}^2} + \sigma \quad \text{where} \quad \sigma \equiv \frac{2R}{Et}$$

Utilizing the relations above, the speed at which sound travels within the representative vapor/liquid mixture is a function of vapor/liquid mass ratio. The effect of increasing liquid fraction, i.e. decreasing vapor/liquid ratio, is to decrease the sound speed. Physically, adding liquid droplets effectively mass loads the mixture, while not appreciably changing the compressibility of the air. Over the parameter range of interest, the relation between mixture sound speed and vapor/liquid ratio is well behaved and monatomic.

While the calibration curves based on predictions from first principles are encouraging, using empirical data mapping from sound speed to vapor/liquid ratio may result in improved accuracy of the present invention to measure the vapor/liquid fractions of the mixture.

The sound speed increases with increasing frequency and asymptotes toward a constant value. The sound speed asymptote at higher frequency is essentially the sound speed of air only with no influence of the suspended liquid droplets. Also, it is apparent that the sound speed of the vapor/liquid mixture has not reached the quasi-steady limit at the lowest frequency for which sound speed was measured. The sound speed is continuing to decrease at the lower frequency limit. An important discovery of the present invention is that the speed at which sound propagates through droplets suspended in a continuous vapor is said to be dispersive. As defined herein, the speed at which acoustic waves propagate through dispersive mixtures varies with frequency.

Figure 24:
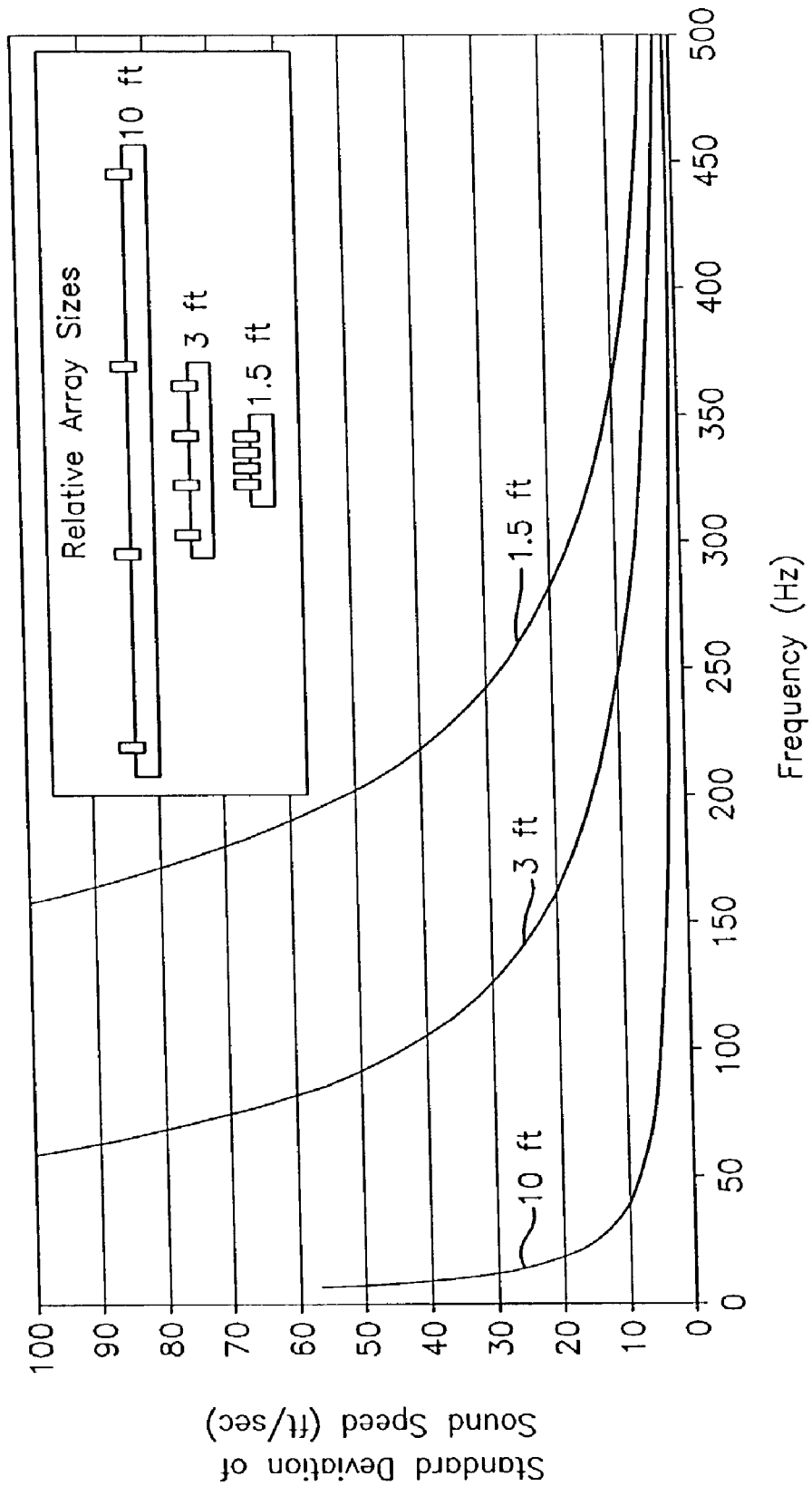
FIG. 24 is a plot showing the standard deviation of sound speed versus frequency for various arrays of saturate vapor/liquid mixture parameter measurement system, in accordance with the present invention.

Measuring the sound speed of a saturated vapor/liquid mixture 12 at progressively lower and lower frequencies becomes inherently less accurate as the total length of the array of pressure sensors 15-18 ($\Delta x_{aperture}$), which define the aperture of the array, becomes small compared to the wavelength of the acoustics. In general, the aperture should be at least a significant fraction of a wavelength of the sound speed of interest. Consequently, longer arrays are used to resolve sound speeds at lower frequencies, which will be described in greater detail hereinafter. As shown in FIG. 24, the standard deviation associated with determining the speed of sound in air is shown as a function of frequency for three arrays of varying aperture, namely 1.5 ft, 3 ft and 10 ft.

For accurately measuring sound speeds at ultra-low frequencies, the data suggests that utilizing a quasi-steady model to interpret the relationship between sound speed, measured at frequencies above those at which the quasi-steady model is applicable, and the liquid-to-vapor ratio would be problematic, and may, in fact, be impractical. Thus, the key to understanding and interpreting the composition of vapor/liquid mixtures through sound speed measurements lies in the dispersive characteristics of the vapor/liquid mixture.

In accordance with the present invention the dispersive nature of the system utilizes a first principles model of the interaction between the vapor and liquid droplets. This model is viewed as being representative of a class of models that seek to account for dispersive effects. Other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference. The model allows for slip between the local velocity of the continuous vapor phase and that of the droplets. The drag force on the droplets by the continuous vapor is modeled by a force proportional to the difference between the local vapor velocity and that of the liquid droplets and is balanced by inertial force:

$$F_{drag} = K(U_f - U_p) = \rho_p v_p \frac{\partial U_p}{\partial t}$$

where K=proportionality constant, $U_f$=fluid velocity, $U_p$=liquid droplet velocity, $\rho_p$=liquid droplet density and $v_p$=particle volume.

The effect of the force on the continuous vapor phase by the liquid droplets is modeled as a force term in the axial momentum equation. The axial momentum equation for a control volume of area A and length $\Delta x$ is given by:

$$P_x - P_{x+\Delta x} - K(U_f - U_p)\left\{\frac{\phi_p \Delta x}{v_p}\right\} = \frac{\partial}{\partial t}(\rho_f U_f \Delta x)$$

where P=pressure at locations x and $\Delta x$, $\phi_p$=volume fraction of the liquid droplets, $\rho_f$=vapor density.

The droplet drag force is given by:

$$F_{drag} = K(U_f - U_p) = C_d A_p \frac{1}{2}\rho_f(U_f - U_p)^2$$

where $C_d$=drag coefficient, $A_p$=frontal area of liquid droplet and $\rho_f$=vapor density.

Using Stokes law for drag on a sphere at low Reynold's number gives the drag coefficient as:

$$C_d = \frac{24}{Re} = \frac{24\mu}{\rho_f(U_f - U_p)D_p}$$

where $D_p$=droplet diameter and $\mu$=vapor viscosity.

Solving for K in this model yields:

$$K = 3\pi\mu D_p$$

Using the above relations and 1-dimensional acoustic modeling techniques, the following relation can be derived for the dispersive behavior of an idealized vapor/liquid mixture.

$$a_{mix}(\omega) = a_f \sqrt{\frac{1}{1 + \dfrac{\varphi_p \rho_p}{\rho_f\left(1 + \omega^2 \dfrac{\rho_p^2 v_p^2}{K^2}\right)}}}$$

In the above relation, the fluid SOS, density ($\rho$) and viscosity ($\emptyset$) are those of the pure phase fluid, $v_p$ is the volume of individual droplets and $\phi_p$ is the volumetric phase fraction of the droplets in the mixture.

Figure 25:
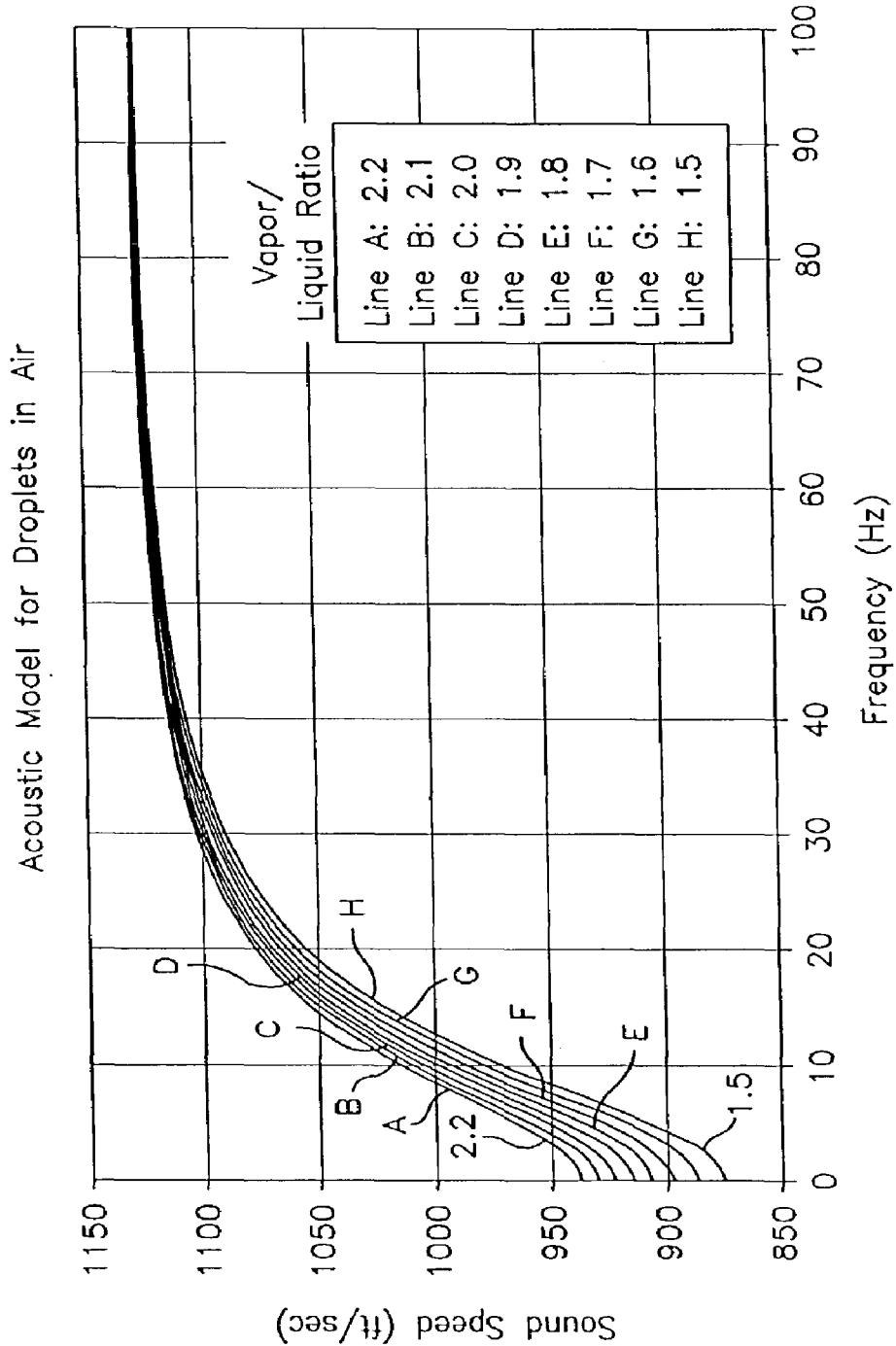
FIG. 25 is a plot of sound speed as a function of frequency for vapor/liquid mixtures with fixed droplet size (50 mm) and varying vapor-to-liquid mass ratio in accordance with the present invention.
Figure 26:
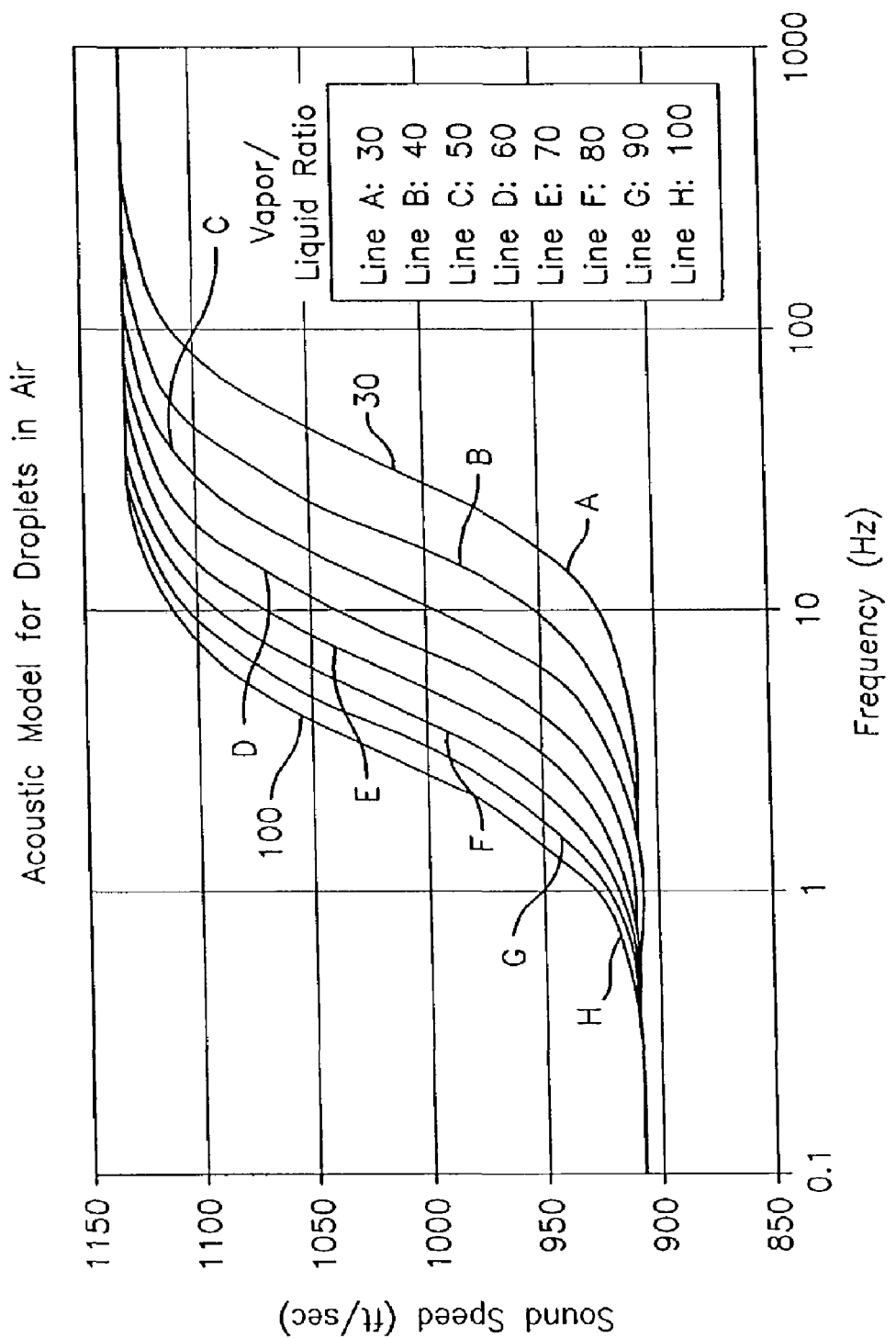
FIG. 26 is a plot of sound speed as a function of frequency for vapor/liquid mixtures with varying particle size where the vapor-to-liquid mass ratio is equal to 1.8 in accordance with the present invention.
Figure 27:
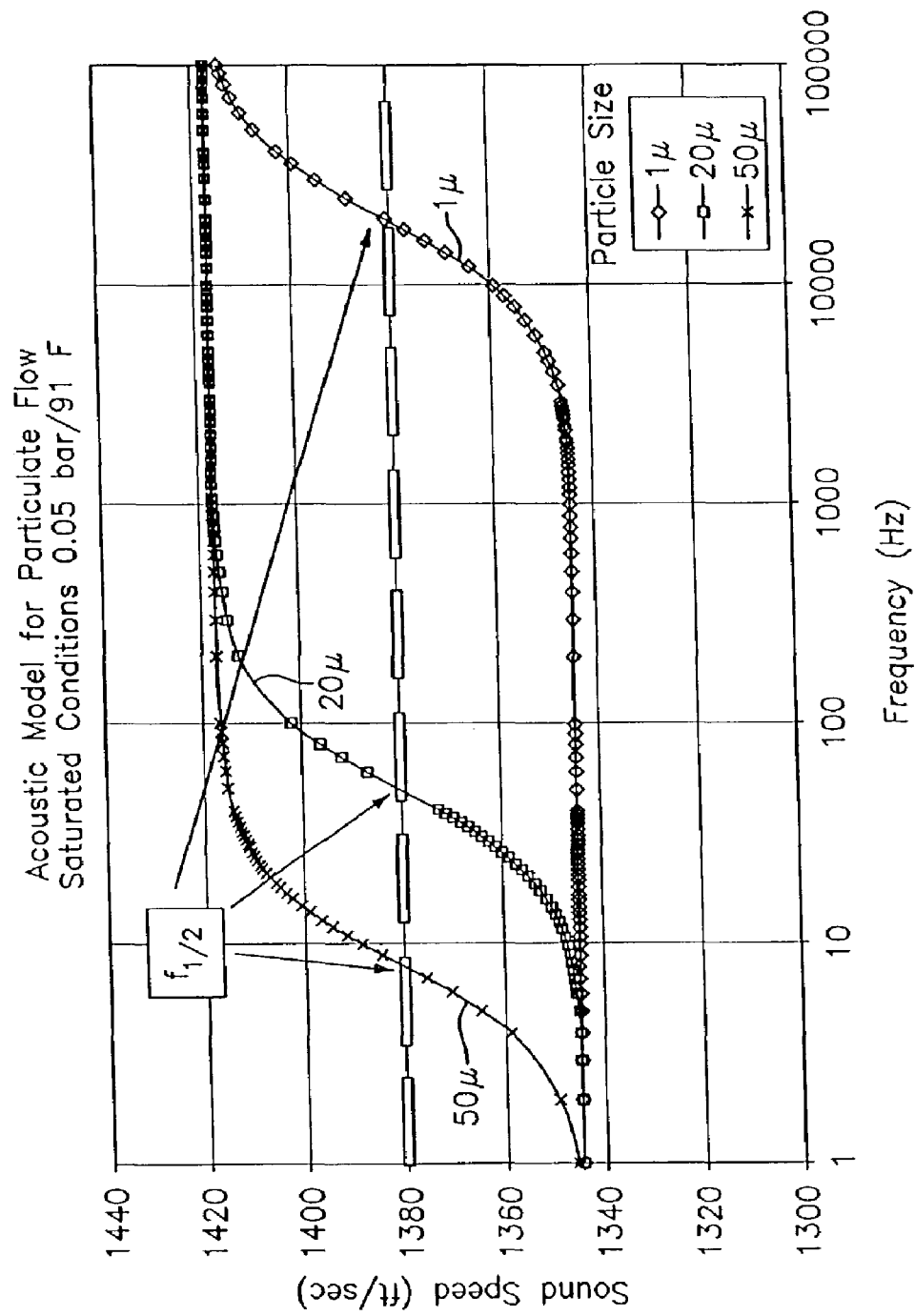
FIG. 27 is a plot of sound speed as a function of frequency for vapor/liquid mixtures with varying particle size, in accordance with the present invention.

Two parameters of primary interest in steam measurements are droplet size and liquid-to vapor mass ratio (i.e., steam quality or steam wetness). To this end, it is of interest to examine the dispersive characteristics of the mixture as a function of these two variables. FIGS. 25 and 26 show the dispersive behavior for vapor/liquid mixtures with parameters typical of those used in steam flow systems.

In particular FIG. 25 shows the predicted behavior for nominally 50 μm size liquid droplets in vapor for a range of liquid-to-vapor ratios. As shown, the effect of liquid-to-vapor ratio is well defined in the low frequency limit. However, the effect of the liquid-to-vapor ratio becomes indistinguishable at higher frequencies, approaching the sound speed of the pure air at high frequencies (above ~100 Hz).

Similarly, FIG. 26 shows the predicted behavior for a vapor/liquid mixture with a liquid-to-vapor ratio of 1.8 with varying liquid droplet size. This figure illustrates that liquid droplet size has no influence on either the low frequency limit (quasi-steady) sound speed, or on the high frequency limit of the sound speed. However, droplet size does have a pronounced effect in the transition region.

FIGS. 25 and 26 illustrate an important aspect of the present invention. Namely, that the dispersive properties of mixtures of droplets suspended in a continuous vapor can be broadly classified into three frequency regimes: low frequency range, high frequency range and a transitional frequency range. Although the effect of droplet size and liquid-to-vapor ratio are inter-related, the predominant effect of liquid-to-vapor ratio is to determine the low frequency limit of the sound speed to be measured and the predominate effect of droplet size is to determine the frequency range of the transitional regions. As droplet size increases, the frequency at which the dispersive properties appear decreases. For typical steam applications, this transitional region begins at fairly low frequencies, ~2 Hz for 50 μm size particles.

In the low frequency regime, the liquid droplets exhibit negligible slip with the vapor. The frequency range for which the no-slip, quasi-steady approximation is valid is a function of a variety of parameters including droplet size, continuous phase viscosity, droplet shape and droplet density.

The quasi-steady sound speed is given by the low frequency limit of the above relation, where VLR is vapor/liquid ratio:

$$a_{mix}(\omega \to 0) = a_f * \sqrt{\frac{1}{1 + \dfrac{\varphi_p \rho_p}{\rho_f}}} \cong a_f * \sqrt{\frac{1}{1 + \dfrac{1}{VLR}}}$$

Note that droplet size does not affect the low frequency limit of the sound speed.

Similar to FIG. 26, FIG. 270 shows the predicted behavior for a saturated vapor/liquid mixture with a liquid-to-vapor ratio with varying droplet size. Specifically, the particle sizes of three different mixtures include 50 um, 20 um and 1 um. The transitional frequency range of the mixture having 50 um droplets is approximately 3-13 Hz, a central frequency ($f_{1/2}$) of approximately 8 Hz. The transitional frequency range of the mixture having 20 um droplets is approximately 11-110 Hz, a central frequency ($f_{1/2}$) of approximately 60 Hz. The transitional frequency range of the mixture having 1 um is approximately 8-80 KHz, a central frequency ($f_{1/2}$) of approximately 40 degrees. As shown, the droplet size greatly influences the dispersion characteristics of the saturated vapor/liquid mixture. The transistion from the quasi-steady state to the high frequency regime scales inversely with the square of the droplet diameter. As discussed hereinbefore, the dispersion characteristics set the frequency requirements for measuring the speed of sound propagating through the mixture to measure parameters of the mixture, and therefore, dispersion defines the length of the sensor array and consequently the length of the sensing device 16 of the probe 170.

The frequency of the speed of sound that is detected for a particular mixture sets the wavelength of interest. The wavelength is the inverse of the frequency, and therefore, the higher the frequency, the shorter the wavelength and vice versa. The wavelength, therefore, defines the aperture ($\Delta x_{aperture}$) of the array 150 (See FIG. 23). As described hereinbefore, the aperture should be at least a significant fraction of the length of the wavelength of the speed of sound of interest. For example, a vapor/liquid mixture having droplets of approximately 30 um has a central frequency ($f_{1/2}$) of approximately 30 Hz, which corresponds to an aperture of approximately 20 ft. Similarly, a vapor/liquid mixture having droplets of approximately 3 um has a central frequency ($f_{1/2}$) of approximately 3 KHz, which corresponds to an aperture of approximately 1 ft. Consequently, the size of the liquid droplet defines the length of the aperture of the probe. In other words, the larger the size of the droplet, the longer the aperture needed to measure the speed of sound to determine specific parameters of the mixture. Similarly, the smaller the size of the droplet, the shorter the aperture needed to measure the speed of sound to determine specific parameters of the mixture, and therefore there is a practical limit for the length of the probe for a particular application.

In the high frequency limit, the dispersion relation predicts the sound speed with asymptote towards the sound speed of the pure vapor.

$$a_{mix}(\omega \Rightarrow \infty) = a_{fluid}$$

Interestingly, the high frequency limit is independent of both droplet size and liquid-to-vapor ratio.

Given the difficulties measuring sufficiently low frequencies to apply the quasi-steady model and recognizing that the high frequency sound speed contains no direct information on either droplet size or liquid-to-vapor ratio, it becomes apparent that the dispersive characteristics of the vapor/liquid mixture should be utilized to determine droplet size and liquid-to-vapor ratio based on speed of sound measurements.

As described hereinbefore, the probe 10 of the present invention includes the ability to accurately determine the average droplet size and the liquid/vapor ratio of the liquid in the vapor/liquid mixture. Provided there is no appreciable slip between the vapor and the liquid droplet, the propagation of one-dimensional sound wave through multiphase mixtures is influenced by the effective mass and the effective compressibility of the mixture. For an air transport system, the degree to which the no-slip assumption applies is a strong function of droplet size and frequency. In the limit of small droplets and low frequency, the no-slip assumption is valid. As the size of the droplet increases and the frequency of the sound waves increase, the non-slip assumption becomes increasing less valid. For a given average liquid droplet size, the increase in slip with frequency causes dispersion, or, in other words, the sound speed of the mixture to change with frequency. With appropriate calibration the dispersive characteristic of a mixture will provide a measurement of the average droplet size, as well as, the vapor to liquid ratio of the mixture.

Using the model described above, which yields the equation shown below, and experimentally determined sound speed as function of frequency, the present invention includes an optimization procedure to simultaneously determine droplet size and VLR in liquid/vapor mixtures:

$$a_{mix}(\omega) = a_f \sqrt{\cfrac{1}{1 + \cfrac{\varphi_p \rho_p}{\rho_f\left(1 + \omega^2 \cfrac{\rho_p^2 v_p^2}{K^2}\right)}}}$$

Figure 28:
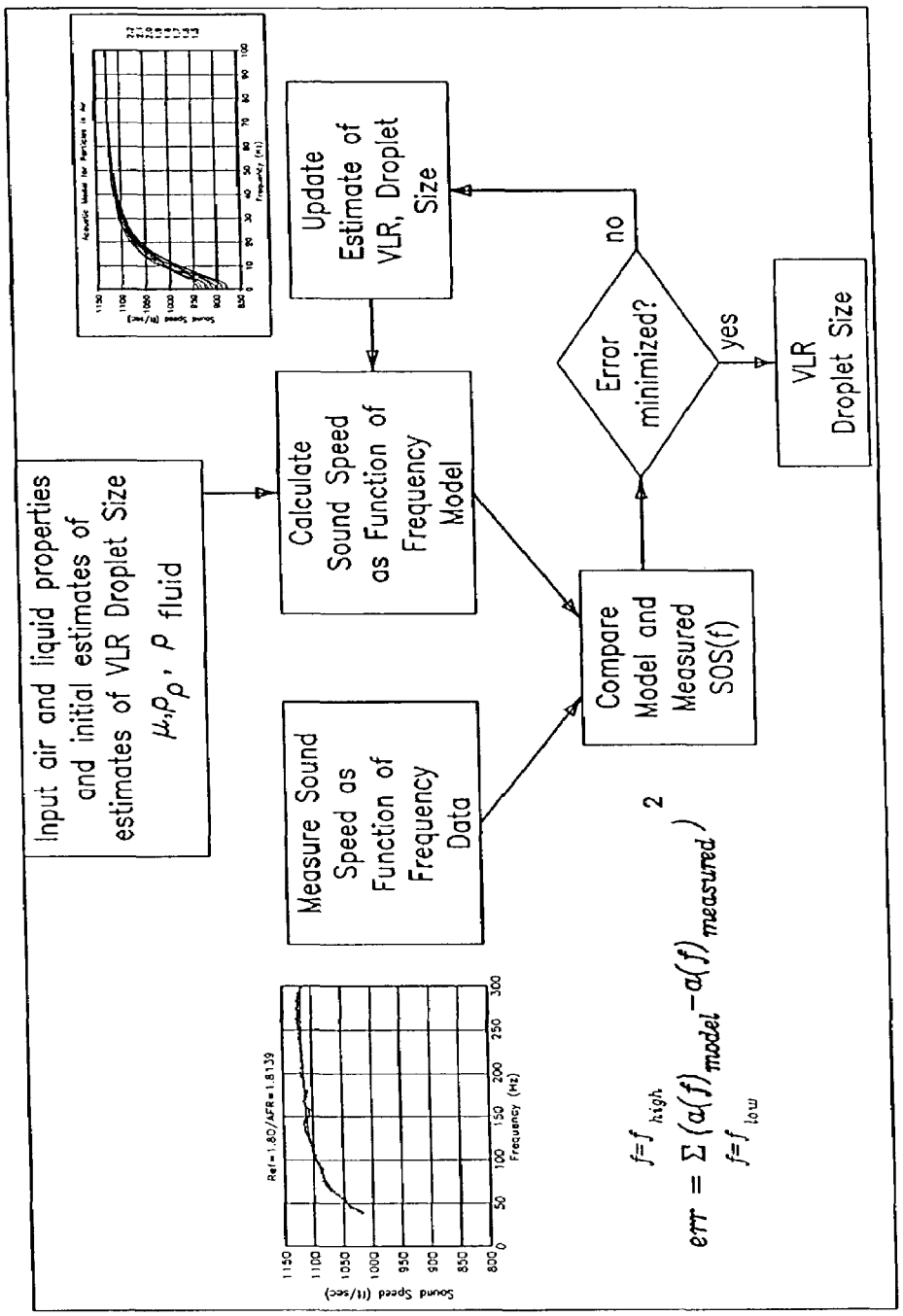
FIG. 28 is a flow diagram of an optimization procedure employed to determine vapor-to-liquid ratio and droplet size from analytical model and experimentally determined dispersive speed of sound data in accordance with the present invention.

Referring to FIG. 28 there is shown an optimization procedure in accordance with the present invention in which the free parameters of an analytical model are optimized to minimize an error function. For illustration purposes, the error function utilized is the sum of the differences of the sound speeds between an analytical model and the experimentally determined sound speed as a function of frequency:

$$err = \sum_{f=f_{low}}^{f=f_{high}} \left(a(f)_{model} - a(f)_{measured}\right)^2$$

Figure 29:
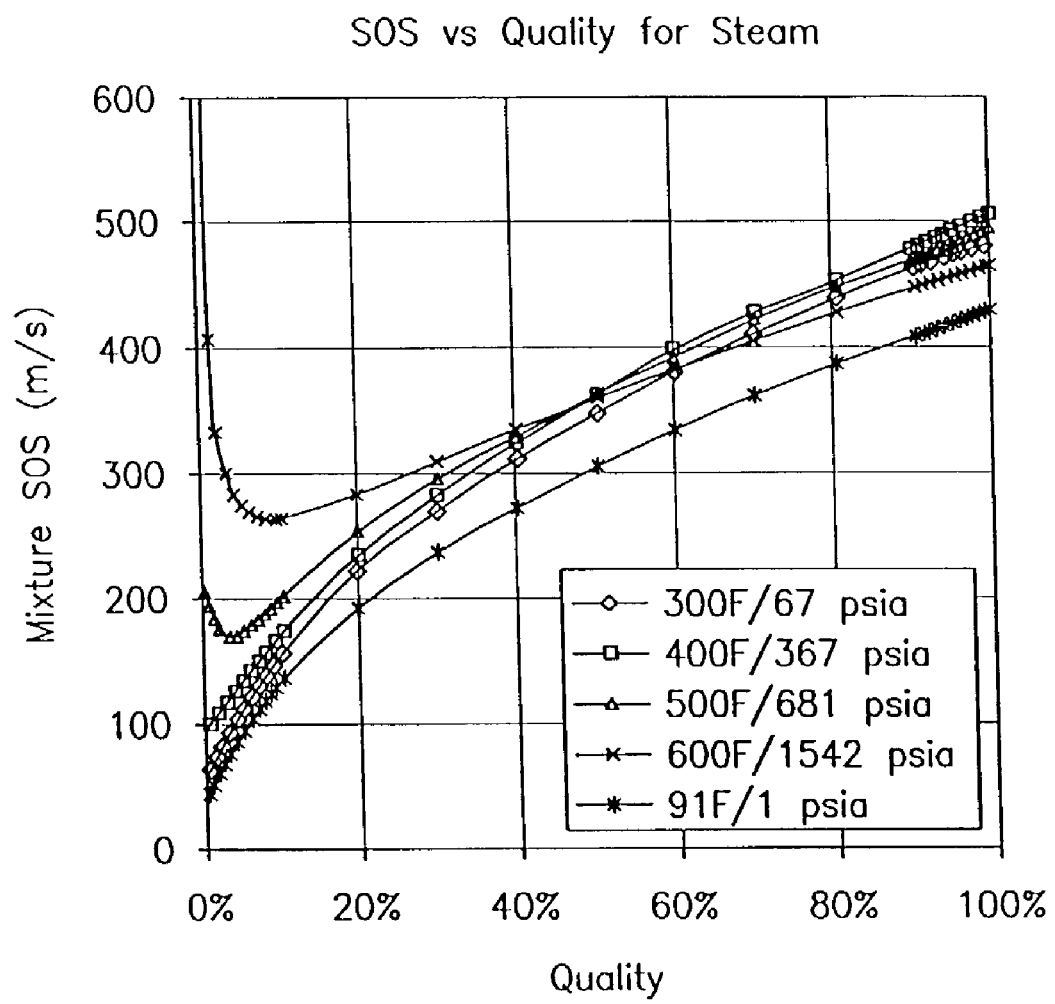
FIG. 29 is a plot of the speed of sound propagating through a saturated vapor/liquid mixture having varying temperature and pressures versus quality of the mixture, in accordance with the present invention.

Thus, the sound speed of a two-phase mixture varies with the ratio vapor and liquid phases present in the mixture. Through these relations, and using tabulated values for the sound speed and densities of the liquid and vapor phases of a process mixture, one can construct an explicit relationship between mixture sound speed and mixture quality. It should be noted that the Wood equation is an engineering approximation, the accuracy of which is dependent on the validity of a variety of assumptions. Experimental data may be required to define between quality and sound speed within required, but to be defined, accuracy limits. Various curves are produced in FIG. 29 showing the relationship of sound speed versus steam quality for well-mixed saturated steam mixtures over of range of temperatures and pressures.

Figure 30:
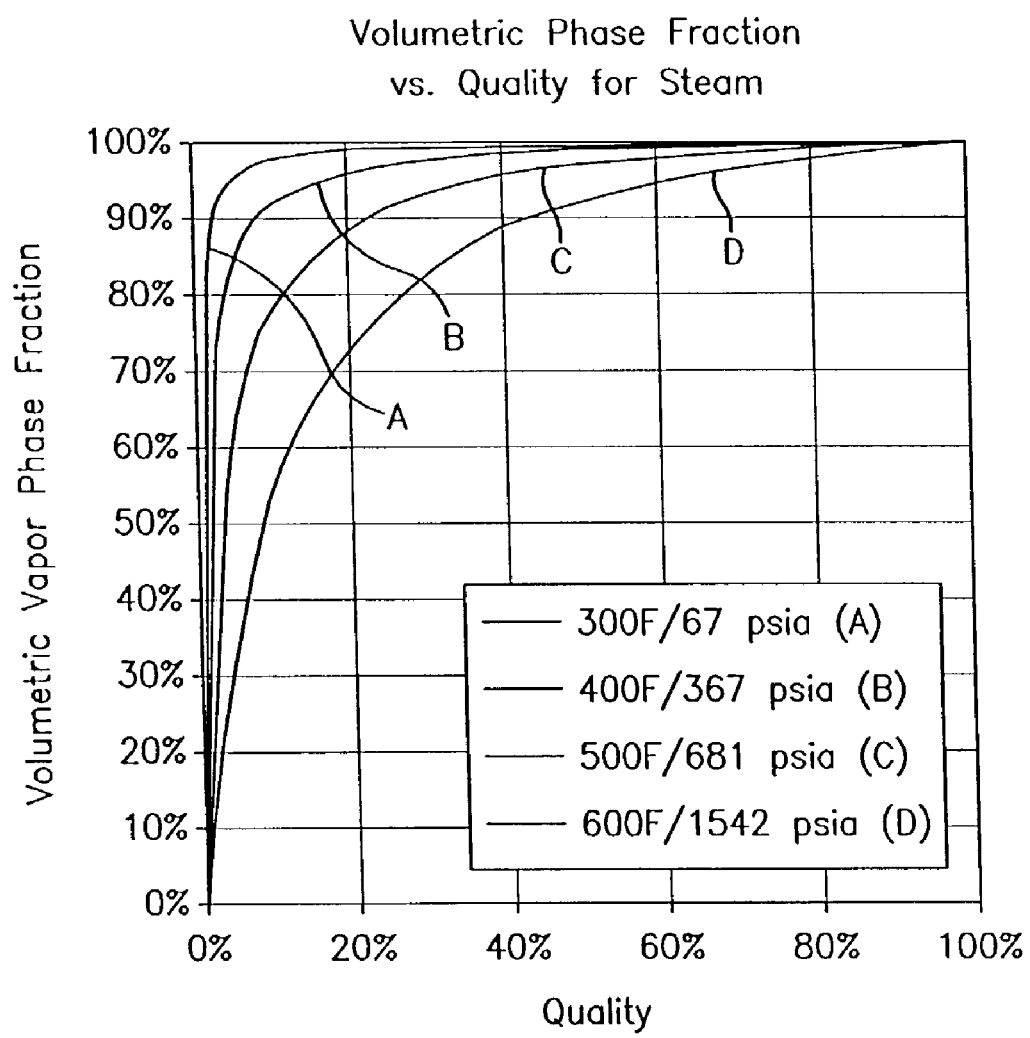
FIG. 30 is a plot of the volumetric vapor phase fraction for vapor/liquid mixtures having varying temperature and pressures versus quality of the mixture, in accordance with the present invention.

As is known in the art, the relationship between quality of a vapor/liquid mixture, a mass ratio, and the volumetric phase fraction of the vapor phase is dependent on the properties of the vapor and liquid phases. For steam the relationship is shown in FIGS. 29 and 30. According to an empirical flow model, the assumption of well mixed, mist-like flows are typically applicable for process mixtures having vapor volumetric phase fractions greater than 0.83 and with mixture velocities exceeding 3.5*sqrt(D*g), where D is the tube 14 diameter and g is the acceleration due to gravity. For example, an 18 inch diameter steam tube translates to mixture velocities greater than ~8 m/s (~26 ft/sec).

Figure 31:
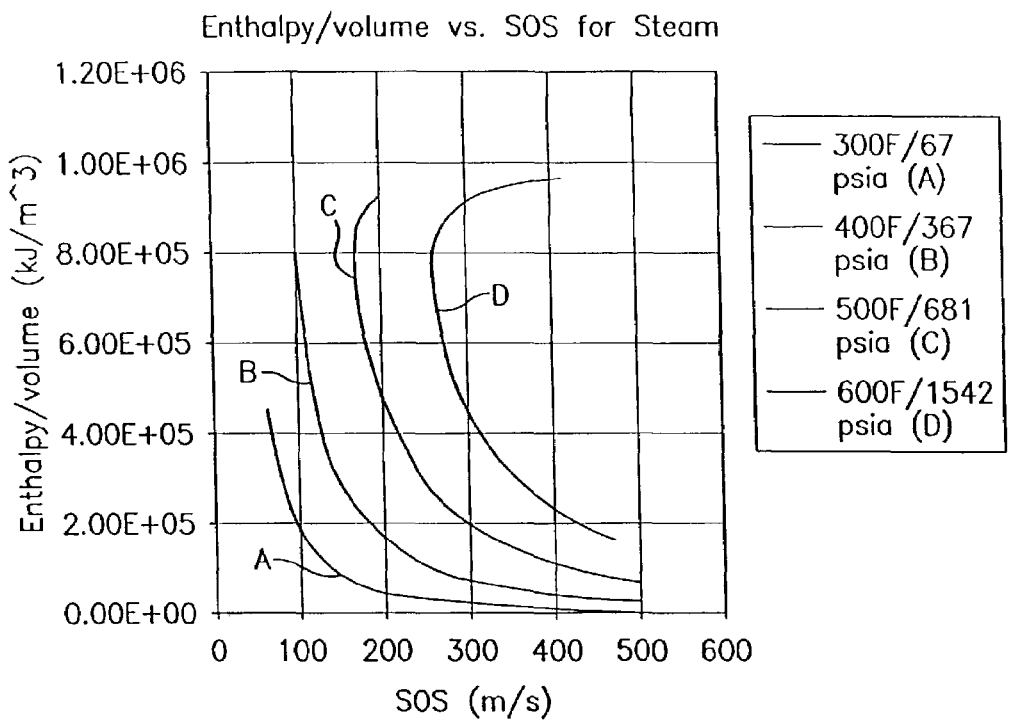
FIG. 31 is a plot of the enthalpy/volume for vapor/liquid mixtures having varying temperature and pressures versus the speed of sound propagating through the mixture, in accordance with the present invention.
Figure 32:
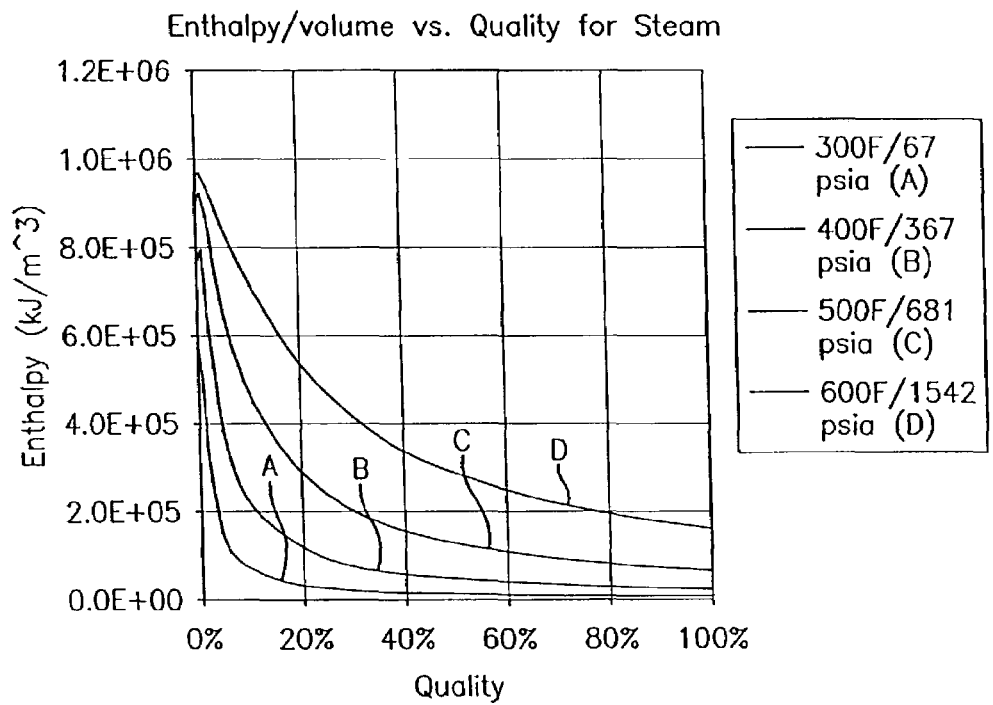
FIG. 32 is a plot of the enthalpy/volume for vapor/liquid mixtures having varying temperature and pressures versus quality of the mixture, in accordance with the present invention.

As developed above, determining the enthalpy flux of a steam mixture is an important measurement. In accordance with the present invention when the total volumetric flow of the mixture is known, the enthalpy per unit volume of the mixture is needed to determine the total flow rate. FIG. 31 shows the relationship between enthalpy per unit volume and mixture sound speed for steam at a variety of conditions. The present invention further utilizes the relationship between enthalpy per unit volume and mixture sound speed for steam at a variety of conditions and the relationship between enthalpy per unit volume and steam quality as shown in FIG. 32 to determine the quality of steam of a flow.

In addition to measuring the liquid to vapor ratio of the mixture 12 and droplet size of the liquid suspended in the mixture using the measured speed of sound, the probe 10 further includes the ability to measure of volumetric flow rate of the mixture by comparing the difference of the speed of one dimensional sound waves propagating with and against the mean flow.

This method of determining the volumetric flow rate of the vapor/liquid mixture 12 relies on the interaction of the mean flow with the acoustic pressure field. The interaction results in sound waves propagating with the mean flow traveling at the speed of sound (if the vapor/liquid mixture were not flowing) plus the convection velocity and, conversely, sound waves traveling against the mean flow propagating at the speed of sound minus the convection velocity. That is, $$a_R = a_{mix} + u$$

$$a_L = a_{mix} - u$$

where $a_R$=velocity of a right traveling acoustic wave relative to a stationary observer (i.e. the tube 14), $a_L$=velocity of a left traveling acoustic wave apparent to a stationary observer, $a_{mix}$=speed of sound traveling through the mixture (if the mixture was not flowing) and u=the mean flow velocity (assumed to be flowing from left to right in this instance). Combining these two equations yields an equation for the mean velocity, $$u = \frac{a_R - a_L}{2}$$

Therefore, by measuring the propagation velocity of acoustic waves in both directions relative to the stationary tube 14 as described hereinbefore, the mean flow velocity can be calculated by multiplying the mean flow velocity by the cross-sectional area of the tube 14.

The practicality of using this method to determine the mean flow is predicated on the ability to resolve the sound speed in both directions with sufficient accuracy to determine the volumetric flow. For typical vapor liquid measurements, flow velocities are typically at ~10 ft/sec and sound speeds of ~4000 ft/sec. Thus axial mach numbers are on the order of 10/4000 of 0.0025. For a +/−10% accuracy in flow rate (+/−1 ft/sec), the sound speed of the upstream and downstream propagating waves would need to be resolved to +/−0.5/4000 or 1 part in 8,000.

However, for saturated vapor/liquid mixture flows, axial flow velocities are nominally around 70 ft/sec with no flow sound speeds of ~700 ft/sec. This results in mach numbers of ~0.1, approximately 2 orders of magnitude greater than typical vapor flows. For saturated vapor/liquid flows, to resolve the flow rate to 10% accuracy (or +/−7 ft/sec), one would have to resolve the sound speed to +/−3.5 ft/sec, or 3.5/700 or 1 part in 200.

For the sound speed measurement, the probe 10 utilizes similar processing algorithms as those employed herein before, and described in greater detail hereinafter. The temporal and spatial frequency content of sound propagating within the tube 14 is related through a dispersion relationship.

$$\omega = \frac{k}{a_{mix}}$$

The wave number is k, which is defined as k=2π/λ, ω is the temporal frequency in rad/sec, and $a_{mix}$ is the speed at which sound propagates within the process piping. For this cases where sound propagates in both directions, the acoustic power is located along two acoustic ridges, one for the sound traveling with the flow at a speed of $a_{mix}+V_{mix}$ and one for the sound traveling against the flow at a speed of $a_{mix}-V_{mix}$.

Figure 33:
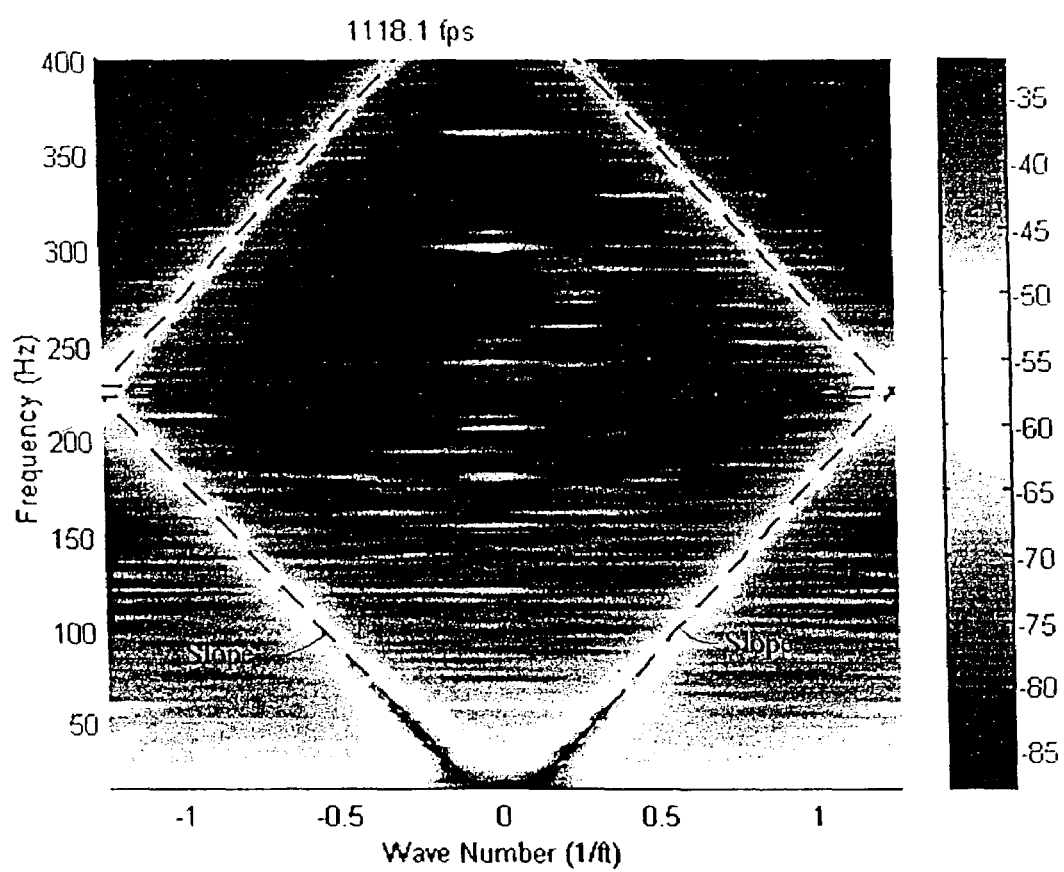
FIG. 33 is a kω plot of data processed from an array of pressure sensors use to measure the speed of sound propagating through a saturated vapor/liquid mixture flowing in a pipe, in accordance with the present invention.

FIG. 33 shows a k-ω plot generated for acoustic sound field of a vapor/liquid mixture flowing through a tube. Two acoustic ridges are clearly evident. Each of the slopes of the two depicted acoustic ridges respectively defines the speed of sound traveling with and against the mean flow.

Further, FIG. 33 illustrates the ability of the present invention to determine the velocity of a fluid moving in a pipe. The figures are plots of data from an actual test run of a probe 10 in accordance with the invention as described herein above. FIG. 33 shows a wavenumber-frequency plot (k-w plot) of unsteady pressure data collected with a probe 10 of the present invention comprising a 4-sensor axial array in an atmospheric pressure loop flowing air at a velocity of approximately 40 ft/sec. The color contours represent the relative signal power at all combinations of frequency and wavenumber. The highest power "ridges" represent the acoustic wave with slope of the ridges equal to the propagation speed. Note that the acoustic ridges "wrap" to the opposite side of the plot at the spatial Nyquist wavenumber equal to ±3.14 in this case (i.e. the acoustic ridge that slopes up and to the right starting at the bottom of the plot, the right-side ridge, wraps to the left side of the plot at approximately 550 Hz and continues sloping up and to the right). The dashed lines show the best-fit two-variable maximization of the power with the two variables being sound speed and flow velocity. The right-side ridge represents the acoustic wave traveling in the same direction as the bulk flow and therefore its slope is steeper than the left-side ridge that represents the acoustic wave traveling in the opposite direction of the bulk flow. This indicates that the acoustic wave traveling in the same direction of the flow is traveling faster than the acoustic wave traveling in the opposite direction of the bulk flow relative to the stationary sensors located on the probe.

The probe 110 of FIG. 23 is configured and programmed to measure and utilize the speed of sound propagating through a flowing vapor/liquid mixture 12 to determine volumetric flow rate. Referring to FIG. 17, a probe 170 embodying the present invention includes the ability to measure volumetric flow rate of the mixture by measuring the unsteady pressures generated by vortical disturbance 188 propagating in the mixture. The probe 170 uses one or both of the following techniques to determine the convection velocity of the vortical disturbances within the vapor/liquid mixture 12 by:

1) Cross-correlating unsteady pressure variations using an array of unsteady pressure sensors.

2) Characterizing the convective ridge of the vortical disturbances using an array of unsteady pressure sensors.

The overwhelming majority of industrial process flows involve turbulent flow. Turbulent fluctuations within the process flow govern many of the flow properties of practical interest including the pressure drop, heat transfer, and mixing. For engineering applications, considering only the time-averaged properties of turbulent flows is often sufficient for design purposes. For sonar flow metering technology, understanding the time-averaged velocity profile in turbulent flow provides a means to interpret the relationship between speed at which coherent structures convect and the volumetrically averaged flow rate.

From the saturated vapor/liquid mixture mechanics perspective, this method relies on the ability of the probe 170 to isolate the convective pressure field (which convects at or near the mean velocity of the saturated vapor/liquid mixture) from the acoustic pressure field (which propagates at the at the speed of sound). In this sense, the velocity measurement is independent of the sound speed measurement.

Figure 35:
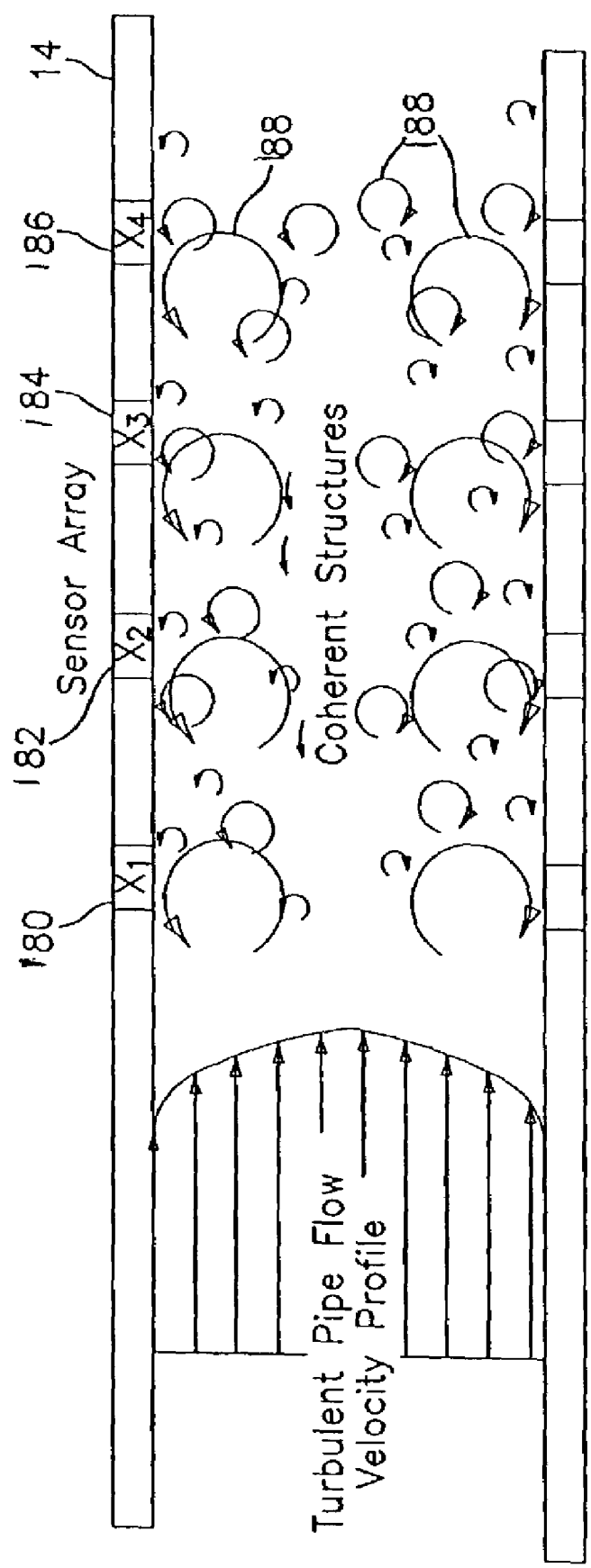
FIG. 35 is a cross-sectional view of a pipe showing a turbulent pipe flow velocity profile.

For turbulent flows, the time-averaged axial velocity varies with radial position, from zero at the wall to a maximum at the centerline of the tube. The flow near the wall is characterized by steep velocity gradients and transitions to relatively uniform core flow near the center of the tube 14. FIG. 35 shows a representative schematic of a velocity profile and coherent vortical flow structures 188 present in fully developed turbulent tube flow 12. The vortical structures 188 are superimposed over time averaged velocity profile within the tube 14 and contain temporally and spatially random fluctuations with magnitudes typically less than 10% percent of the mean flow velocity.

From a volumetric flow measurement perspective, the volumetrically averaged flow velocity is of interest. The volumetrically averaged flow velocity, defined as $V=Q/A$, is a useful, but arbitrarily defined property of the flow. Here, A is the cross sectional area of the tube and Q is the volumetric flow rate. In fact, given the velocity profile within the tube, little flow is actually moving at this speed.

Turbulent tube flows are highly complex flows. Predicting the details of any turbulent flow is problematic, however, much is known regarding the statistical properties of the flow. For instance, turbulent flows contain self-generating, coherent vortical structures often termed "turbulent eddies". The maximum length scale of these eddies is set by the diameter of the tube 14. These structures remain coherent for several tube diameters downstream, eventually breaking down into progressively smaller eddies until the energy is dissipated by viscous effects.

Experimental investigations have established that eddies generated within turbulent boundary layers convect at roughly 80% of maximum flow velocity. For tube flows, this implies that turbulent eddies will convect at approximately the volumetrically averaged flow velocity within the tube. The precise relationship between the convection speed of turbulent eddies and the flow rate for each class of meters can be calibrated empirically as described below.

The probe 170 of FIG. 34 determines the convection velocity of the vortical disturbances within the vapor/liquid mixture by cross correlating unsteady pressure variations using an array of unsteady pressure sensors, similar to that shown in U.S. patent application Ser. No. 10/007,736, filed Nov. 8, 2001, entitled "Flow Rate Measurement Using Unsteady Pressures", which is incorporated herein by reference.

Referring to FIG. 34, the probe 170 includes a sensing section 172 along a tube 14 and a signal processing unit 174. The tube 14 has two measurement regions 176,178 located a distance $\Delta X$ apart along the tube 14. At the first measurement region 176 are two unsteady (or dynamic or ac) pressure sensors 180,182, located a distance $X_1$ apart, capable of measuring the unsteady pressure in the tube 14, and at the second measurement region 178, are two other unsteady pressure sensors 84,86, located a distance $X_2$ apart, capable of measuring the unsteady pressure in the tube 14. Each pair of pressure sensors 180,182 and 184,186 act as spatial filters to remove certain acoustic signals from the unsteady pressure signals, and the distances $X_1, X_2$ are determined by the desired filtering characteristic for each spatial filter, as discussed hereinafter.

The probe 170 of the present invention measures velocities associated with unsteady flow fields and/or pressure disturbances represented by 188 associated therewith relating to turbulent eddies (or vortical flow fields), inhomogeneities in the flow, or any other properties of the flow, liquid, vapor, or pressure, having time varying or stochastic properties that are manifested at least in part in the form of unsteady pressures. The vortical flow fields are generated within the vapor of the tube 14 by a variety of non-discrete sources such as remote machinery, pumps, valves, elbows, as well as the fluid or mixture flow itself. It is this last source, the fluid flowing within the tube, that is a generic source of vortical flow fields primarily caused by the shear forces between the vapor and the wall of the tube that assures a minimum level of disturbances for which the present invention takes unique advantage. The flow generated vortical flow fields generally increase with mean flow velocity and do not occur at any predeterminable frequency. As such, no external discrete vortex-generating source is required within the present invention and thus may operate using passive detection. It is within the scope of the present that the pressure sensor spacing may be known or arbitrary and that as few as two sensors are required if certain information is known about the acoustic properties of the system as will be more fully described herein below.

The vortical flow fields 188 are, in general, comprised of pressure disturbances having a wide variation in length scales and which have a variety of coherence length scales such as that described in the reference "Sound and Sources of Sound", A. P. Dowling et al, Halsted Press, 1983, which is incorporated by reference to the extend of understanding the invention. Certain of these vortical flow fields 188 convect at or near, or related to the mean velocity of at least one of the elements within a mixture flowing through the inner tube 14 of the probe 170. The vortical pressure disturbances 188 that contain information regarding convection velocity have temporal and spatial length scales as well as coherence length scales that differ from other disturbances in the flow. The present invention utilizes these properties to preferentially select disturbances of a desired axial length scale and coherence length scale as will be more fully described hereinafter. For illustrative purposes, the terms vortical flow field and vortical pressure field will be used to describe the above-described group of unsteady pressure fields having temporal and spatial length and coherence scales described herein.

The pressures $P_1, P_2, P_3, P_4$ may be measured through holes in the tube 14 ported to external pressure sensors or by other techniques discussed hereinafter. The pressure sensors 180, 182,184,186 provide time-based pressure signals $P_1(t), P_2(t), P_3(t), P_4(t)$ on lines 190-193, respectively, to signal processing unit 174 which provides a convection velocity signal $U_c(t)$ on a line 196 which is related to an average flow rate $U_f(t)$ of the vapor flowing through the inner tube 14 of the probe 170.

Also, some or all of the functions within the signal processing unit 174 may be implemented in software (using a microprocessor or computer) and/or firmware, or may be implemented using analog and/or digital hardware, having sufficient memory, interfaces, and capacity to perform the functions described herein.

In particular, in the processing unit 174, the pressure signal $P_1(t)$ on the line 190 is provided to a positive input of a summer 200 and the pressure signal $P_2(t)$ on the line 191 is provided to a negative input of the summer 200. The output of the summer 200 is provided to line 204 indicative of the difference between the two pressure signals $P_1, P_2$ (e.g., $P_1-P_2=P_{as1}$).

The pressure sensors 180,182 together with the summer 200 create a spatial filter 176. The line 204 is fed to bandpass filter 208, which passes a predetermined passband of frequencies and attenuates frequencies outside the passband. In accordance with the present invention, the passband of the filter 208 is set to filter out (or attenuate) the dc portion and the high frequency portion of the input signals and to pass the frequencies therebetween. Other passbands may be used in other embodiments, if desired. Passband filter 208 provides a filtered signal $P_{asf}1$ on a line 212 to Cross-Correlation Logic 216, described hereinafter.

The pressure signal $P_3(t)$ on the line 192 is provided to a positive input of a summer 202 and the pressure signal $P_4(t)$ on the line 193 is provided to a negative input of the summer 202. The pressure sensors 83,84 together with the summer 202 create a spatial filter 178. The output of the summer 202 is provided on a line 206 indicative of the difference between the two pressure signals $P_3, P_4$ (e.g., $P_3-P_4=P_{as2}$). The line 206 is fed to a bandpass filter 210, similar to the bandpass filter 108 discussed hereinbefore, which passes frequencies within the passband and attenuates frequencies outside the passband. The filter 210 provides a filtered signal $P_{asf}2$ on a line 214 to the Cross-Correlation Logic 216. The signs on the summers 200,202 may be swapped if desired, provided the signs of both summers are swapped together. In addition, the pressure signals $P_1, P_2, P_3, P_4$ may be scaled prior to presentation to the summers 200,202.

The Cross-Correlation Logic 216 calculates a known time domain cross-correlation between the signals $P_{asf1}$ and $P_{asf2}$ on the lines 212,214, respectively, and provides an output signal on a line 218 indicative of the time delay $\tau$ it takes for an vortical flow field 188 (or vortex, stochastic, or vortical structure, field, disturbance or perturbation within the flow) to propagate from one sensing region 176 to the other sensing region 178. Such vortical flow disturbances, as is known, are coherent dynamic conditions that can occur in the flow which substantially decay (by a predetermined amount) over a predetermined distance (or coherence length) and convect (or flow) at or near the average velocity of the fluid flow. As described above, the vortical flow field 188 also has a stochastic or vortical pressure disturbance associated with it. In general, the vortical flow disturbances 188 are distributed throughout the flow, particularly in high shear regions, such as boundary layers (e.g., along the inner wall of the tube 14) and are shown herein as discrete vortical flow fields 188. Because the vortical flow fields (and the associated pressure disturbance) convect at or near the mean flow velocity, the propagation time delay $\tau$ is related to the velocity of the flow by the distance $\Delta X$ between the measurement regions 176,178, as discussed hereinafter.

Although pressure disturbances associated with vortical flow fields 88 occur naturally in most flow conditions, an optional circumferential groove (not shown) may be used in the inner diameter of the tube 14 to help generate unsteady flow fields in the form of vortices into the flow. However, the groove is not required for the present invention to operate, due to vortex generation, which naturally occurs along the inner wall of the tube 14, as discussed hereinbefore. Instead of a single circumferential groove a plurality of axially spaced circumferential grooves may be used. The dimensions and geometry of the groove(s) may be set based on the expected flow conditions and other factors. Other techniques may be used as vortex generators if desired including those that may protrude within the inner diameter of tube 14.

Referring to FIG. 34, a spacing signal $\Delta X$ on a line 220 indicative of the distance $\Delta X$ between the sensing regions 176,178 is divided by the time delay signal $\tau$ on the line 218 by a divider 222 which provides an output signal on the line 196 indicative of the convection velocity $U_c(t)$ of the saturated vapor/liquid mixture flowing in the tube 14, which is related to (or proportional to or approximately equal to) the average (or mean) flow velocity $U_f(t)$ of the mixture, as defined below:

$$U_c(t)=\Delta X/\tau \propto U_f(t) \qquad \text{Eq. 1}$$

The convection velocity $U_c(t)$ may then be calibrated to more precisely determine the mean velocity $U_f(t)$ if desired. The result of such calibration may require multiplying the value of the convection velocity $U_c(t)$ by a calibration constant (gain) and/or adding a calibration offset to obtain the mean flow velocity $U_f(t)$ with the desired accuracy. Other calibration may be used if desired. For some applications, such calibration may not be required to meet the desired accuracy. The velocities $U_f(t), U_c(t)$ may be converted to volumetric flow rate by multiplying the velocity by the cross-sectional area of the tube 14.

Figure 36:
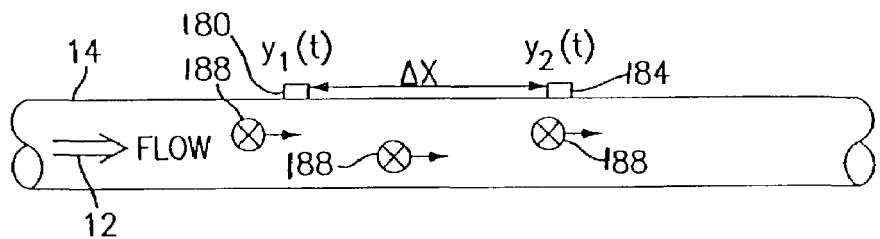
FIG. 36 is a side elevational view of another embodiment of a probe for measuring the vortical disturbances in a pipe, in accordance with the present invention.
Figure 37:
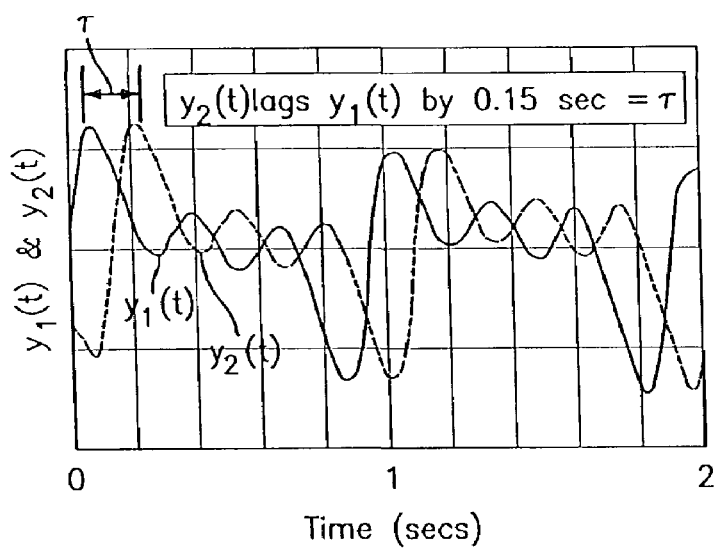
FIG. 37 is a plot of the pressure signals measured by a pair of pressure sensors of the probe of FIG. 36.

Referring to FIGS. 26-38, as is known, cross-correlation may be used to determine the time delay $\tau$ between two signals $y_1(t), y_2(t)$ separated by a known distance $\Delta X$, that are indicative of quantities 180 that convect with the flow (e.g., density perturbations, concentration perturbations, temperature perturbations, vortical pressure disturbances, and other quantities). In FIG. 36, the signal $y_2(t)$ lags behind the signal $y_1(t)$ by 0.15 seconds. If a time domain cross-correlation is taken between the two signals $y_1(t), y_2(t)$, the result is shown in FIG. 37 as a curve 224. The highest peak 226 of the curve 224 shows the best fit for the time lag $\tau$ between the two signals $y_1(t), y_2(t)$ is at 0.15 seconds, which matches the reference time delay, shown in FIG. 38.

Figure 38:
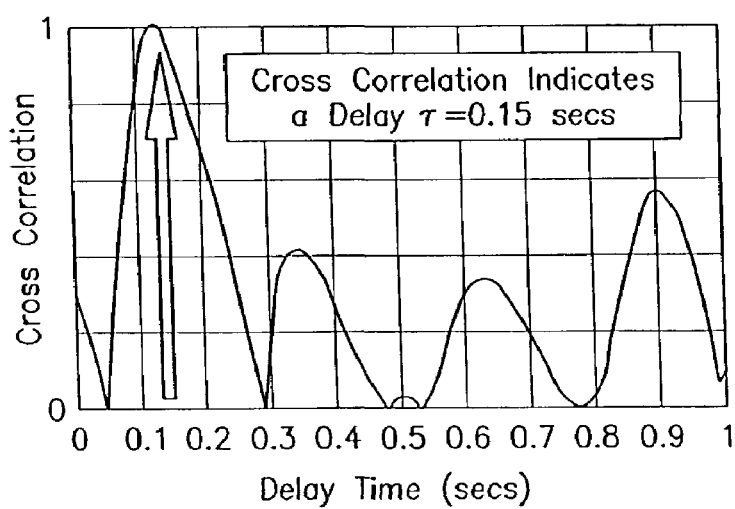
FIG. 38 is a plot of the cross-correlation of the pressure signals plotted in FIG. 37.

Referring to FIG. 38, as discussed hereinbefore, since pressure disturbances associated within the vortical flow field 188 convect (or flow) at or near the average velocity of the mixture flowing in the tube 14, the vortical pressure disturbances observed at the downstream location are substantially a time lagged version of the vortical pressure disturbances observed at the upstream location. However, the total vortical pressure perturbations or disturbances in a tube may be expressed as being comprised of vortical pressure disturbances ($P_{vortical}$), acoustic pressure disturbances ($P_{acoustic}$) and other types of pressure disturbances ($P_{other}$) as shown below expressed in terms of axial position along the tube at any point in time:

$$P(x,t)=P_{vortical}(x,t)+P_{acoustic}(x,t)+P_{other}(x,t) \qquad \text{Eq. 2}$$

As a result, the unsteady pressure disturbances $P_{vortical}$ can be masked by the acoustic pressure disturbances $P_{acoustic}$ and the other types of pressure disturbances $P_{other}$. In particular, the presence of the acoustic pressure disturbances that propagate both upstream and downstream at the speed of sound in the saturated vapor/liquid mixture (sonic velocity), can prohibit the direct measurement of velocity from cross-correlation of direct vortical pressure measurements.

The present invention uses temporal and spatial filtering to precondition the pressure signals to effectively filter out the acoustic pressure disturbances $P_{acoustic}$ and other long wavelength (compared to the sensor spacing) pressure disturbances in the tube 14 at the two sensing regions 176,178 and retain a substantial portion of the vortical pressure disturbances $P_{vortical}$ associated with the vortical flow field 188 and any other short wavelength (compared to the sensor spacing) low frequency pressure disturbances $P_{other}$. In accordance with the present invention, if the low frequency pressure disturbances $P_{other}$ are small, they will not substantially impair the measurement accuracy of $P_{vortical}$.

The $P_{vortical}$ dominated signals from the two regions 176,178 are then cross-correlated to determine the time delay τ between the two sensing locations 176,178. More specifically, at the sensing region 172, the difference between the two pressure sensors 180,182 creates a spatial filter 176 that effectively filters out (or attenuates) acoustic disturbances for which the wavelength λ of the acoustic waves propagating along the flow is long (e.g., ten-to-one) compared to the spacing $X_1$ between the sensors. Other wavelength to sensor spacing ratios may be used to characterize the filtering, provided the wavelength to sensor spacing ratio is sufficient to satisfy the two-to-one spatial aliasing Nyquist criteria.

Thus, if the pressure sensors $P_1,P_2$ have an axial spacing $X_1$, and assuming that the spatial filter 176 will attenuate acoustic wavelengths longer than about 10 times the sensor spacing $X_1$, the smallest acoustic wavelength λmin that is attenuated would be:

$$\lambda_{min}=10(X_1) \quad \text{Eq. 3}$$

One-dimensional acoustic disturbances are also governed by the following known inverse wavelength-frequency relation:

$$\lambda=a/f \text{ or } f=a/\lambda \quad \text{Eq. 4}$$

where a is the speed of sound traveling in the mixture, f is the frequency of the acoustic disturbance, and λ is the wavelength of the acoustic disturbance.

Using Eq. 4, such a spatial filter would filter out frequencies below about:

$$f_{max}=a/\lambda_{min} \quad \text{Eq. 5}$$

The above discussion on the spatial filter 176 also applies to the second spatial filter 178 comprising the other pair of pressure signals $P_3,P_4$, axially spaced a distance $X_2$ apart, which provides the differenced vortical pressure signal $P_{as2}$.

The second technique of determining the convection velocity of the vortical disturbances within the saturated vapor/liquid mixture is by characterizing the convective ridge of the vortical disturbances using an array of unsteady pressure sensors, similar to that shown in U.S. patent application Ser. No. 09/729,994, filed Dec. 4, 2000, entitled "Method and Apparatus for Determining the Flow Velocity Within a Pipe", which is incorporated herein by reference.

The sonar flow metering methodology uses the convection velocity of coherent structure with turbulent tube flows to determine the volumetric flow rate. The convection velocity of these eddies 188 is determined by applying sonar arraying processing techniques to determine the speed at which the eddies convect past an axial array of unsteady pressure measurements distributed along the tube 14.

The sonar-based algorithms determine the speed of the eddies by characterizing both the temporal and spatially frequency characteristics of the flow field. For a train of coherent eddies convecting past a fixed array of sensors, the temporal and spatial frequency content of pressure fluctuations are related through the following relationship:

$$\omega = \frac{k}{U_{convect}}$$

Here k is the wave number, defined as $k=2\pi/\lambda$ and has units of 1/length, ω is the temporal frequency in rad/sec, and $U_{convect}$ is the convection velocity. Thus, the shorter the wavelength (larger k) is, the higher the temporal frequency.

In sonar array processing, the spatial/temporal frequency content of time stationary sound fields are often displayed using "k-ω plots". K-ω plots are essentially three-dimensional power spectra in which the power of a sound field is decomposed into bins corresponding to specific spatial wave numbers and temporal frequencies. On a k-ω plot, the power associated with a pressure field convecting with the flow is distributed in regions, which satisfies the dispersion relationship developed above. This region is termed "the convective ridge" (Beranek, 1992) and the slope of this ridge on a k-w plot indicates the convective velocity of the pressure field. This suggests that the convective velocity of turbulent eddies, and hence flow rate within a tube, can be determined by constructing a k-ω plot from the output of a phased array of sensor and identifying the slope of the convective ridge.

Figure 39:
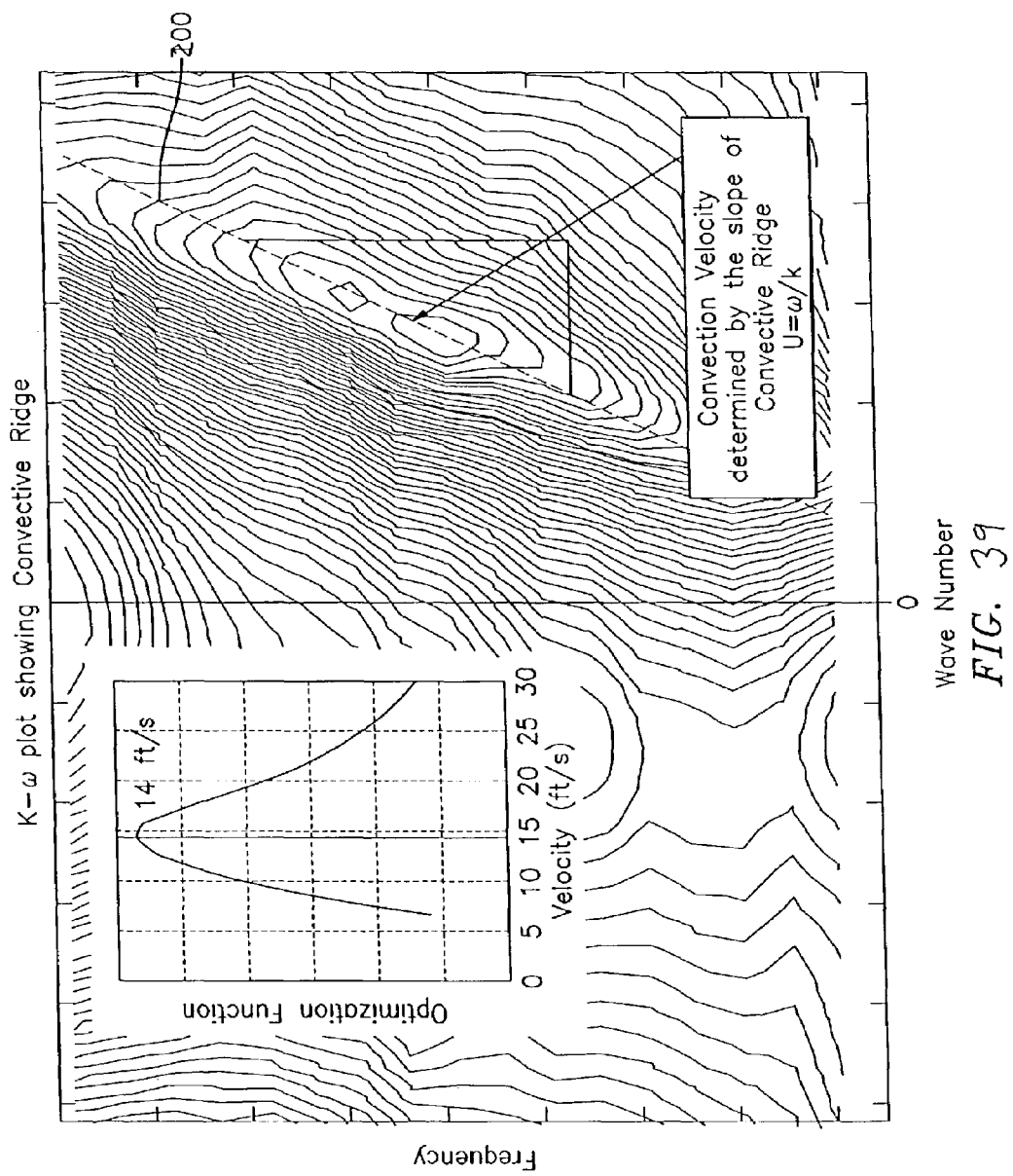
FIG. 39 is a kω plot of data processed from a probe embodying the present invention that illustrates slope of the convective ridge, and a plot of the optimization function of the convective ridge, in accordance with the present invention.

FIG. 39 shows an example of a k-ω plot generated from a phased array of pressure sensors. The power contours show a well-defined convective ridge. A parametric optimization method was used to determine the "best" line representing the slope of the convective ridge 200. For this case, a slope of 14.2 ft/sec was determined. The intermediate result of the optimization procedure is displayed in the insert, showing that optimized value is a unique and well-defined optima.

The k-w plot shown in FIG. 39 illustrates the fundamental principle behind sonar based flow measure, namely that axial arrays of pressure sensors can be used in conjunction with sonar processing techniques to determine the speed at which naturally occurring turbulent eddies convect within a tube.

Figure 40:
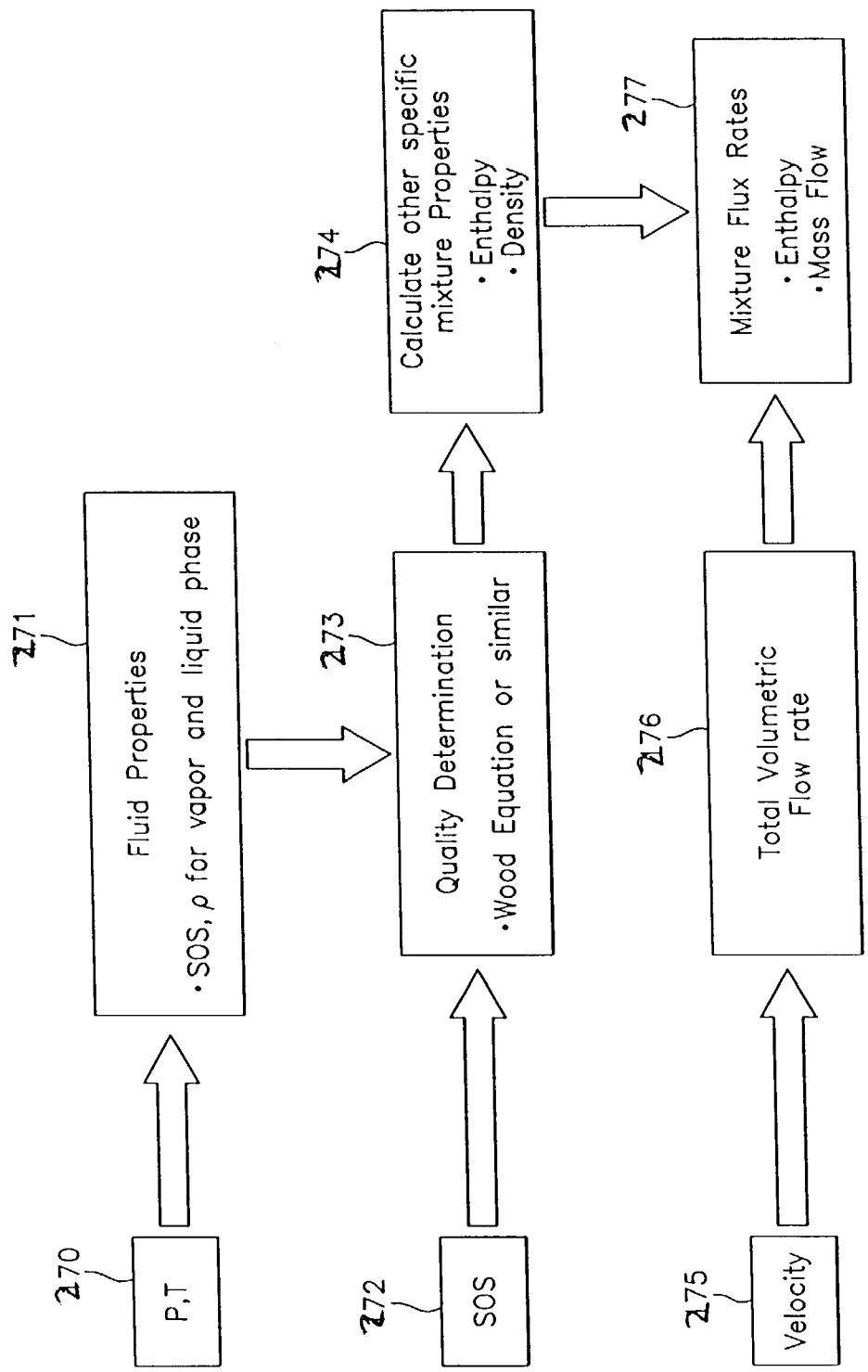
FIG. 40 is a schematic diagram of another embodiment of a probe embodying the present invention.

The present invention will now be described with reference to FIG. 40 wherein the discussions based on the calculation of various parameters and properties are detailed herein above with reference to the various figures. In accordance with the present invention utilizing a probe 110,170 to determine the speed of sound of the mixture provides various specific properties of a saturated vapor/liquid mixture and the velocity of the mixture and further utilizing logic comprising information about the mixture based on the measured parameters. The steady state pressure and temperature of the saturated vapor/liquid mixture may be measured by any known or contemplated method as represented by 270 from which various fluid properties may be determined from tables or graphs of the known relationships for speed of sound and density for the vapor and liquid phases of the mixture as represented by 271. The speed of sound of the saturated vapor/liquid mixture is determined by the probe of the present invention as set forth herein above and represented by 272. The quality of the saturated vapor/liquid mixture is determined from the fluid properties of 271 combined with the saturated vapor/liquid mixture speed of sound 272 using the Wood equation (or similar) as set forth herein above and represented by 273. The present invention also enables the determination of other properties of the saturated vapor/liquid mixture such as enthalpy and density as set forth by 274 by combining the fluid properties of 271 with the quality of the saturated vapor/liquid mixture from 273. The present invention further enables the determination of the velocity of the saturated vapor/liquid mixture by the methods described herein above as represented by 275. The total volumetric flow rate of the saturated vapor/liquid mixture is thereby determined as represented by 276 and when combined with the parameters of other properties of the saturated vapor/liquid mixture such as enthalpy and density as set forth by 274 various flux rates of the mixture such as enthalpy and mass flow rates are enabled as represented by 277.

As described hereinbefore, the length of the array of sensors of the probe 10 of FIG. 23 is dependent on the size of the droplets (or solid particles), while the length of the array of the probe 170 of FIG. 34 is dependent on the length of the coherence of the vortical eddies. Consequently, one will appreciate that while the probes 110,170 of FIGS. 23 and 34, respectively, are shown as separate., distinct probes, one will appreciate that the processing units 30,74, respectively, may receive unsteady pressure signals from a common array of sensors 50,72, respectively, provided the size of the liquid droplets are sufficiently small and/or the coherence of the vortical eddies are sufficiently long in duration. Further the processing units 30,74 may comprise the same hardware (or single unit), wherein the unsteady pressure signals are simply processed separately to provide their respective output signals.

The pressure sensors 18-21 of FIG. 2 described herein may be any type of pressure sensor, capable of measuring the unsteady (or ac or dynamic ) pressures within a tube 14, such as piezoelectric, optical, capacitive, resistive (e.g., Wheatstone bridge), accelerometers (or geophones), velocity measuring devices, displacement measuring devices, etc. If optical pressure sensors are used, the sensors 18-21 may be Bragg grating based pressure sensors, such as that described in U.S. patent application, Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application, Ser. No. 10/224,821, entitled "Non-Intrusive Fiber Optic Pressure Sensor for Measuring Unsteady Pressures within a Pipe", which are incorporated herein by reference. Alternatively, the sensors 14 may be electrical or optical strain gages attached to or embedded in the outer or inner wall of the tube which measure tube wall strain, including microphones, hydrophones, or any other sensor capable of measuring the unsteady pressures within the tube 14. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

For any of the embodiments described herein, the pressure sensors, including electrical strain gages, optical fibers and/or gratings among others as described herein, may be attached to the tube by adhesive, glue, epoxy, tape or other suitable attachment means to ensure suitable contact between the sensor and the tube 14. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite tube. If desired, for certain applications, the gratings may be detached from (or strain or acoustically isolated from) the tube 14 if desired.

It is also within the scope of the present invention that any other strain sensing technique may be used to measure the variations in strain in the tube, such as highly sensitive piezoelectric, electronic or electric, strain gages attached to or embedded in the tube 14.

In certain embodiments of the present invention, a piezoelectronic pressure transducer may be used as one or more of the pressure sensors 15-18 and it may measure the unsteady (or dynamic or ac) pressure variations inside the tube 14 by measuring the pressure levels inside of the tube. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Furthermore the present invention contemplates that each of the pressure sensors 18-21 of the probes 110,170 may include a piezoelectric sensor 30 that provides a piezoelectric material 30 to measure the unsteady pressures of the fluid/particle mixture 12 as shown in FIGS. 9 and 10. The piezoelectric material, such as the polymer, polarized fluoropolymer, polyvinylidene fluoride (PVDF), measures the strain induced within the process tube 14 due to unsteady pressure variations within the process mixture 12. Strain within the tube is transduced to an output voltage or current by the attached piezoelectric sensors 18-21.

While the present invention is capable of measuring liquid droplets suspended in a vapor, one will appreciate that other multi-phase mixtures or flows may be measured using an array of sensors, such as solid particles suspended in a fluid. It is further recognize the effects of dispersion on large droplets of liquid would be similar to large solid particles dispersed in a fluid (e.g., gas or air), and thus similar considerations when measuring the air-to-particle ratio and particle size should be addressed.

Figure 43:
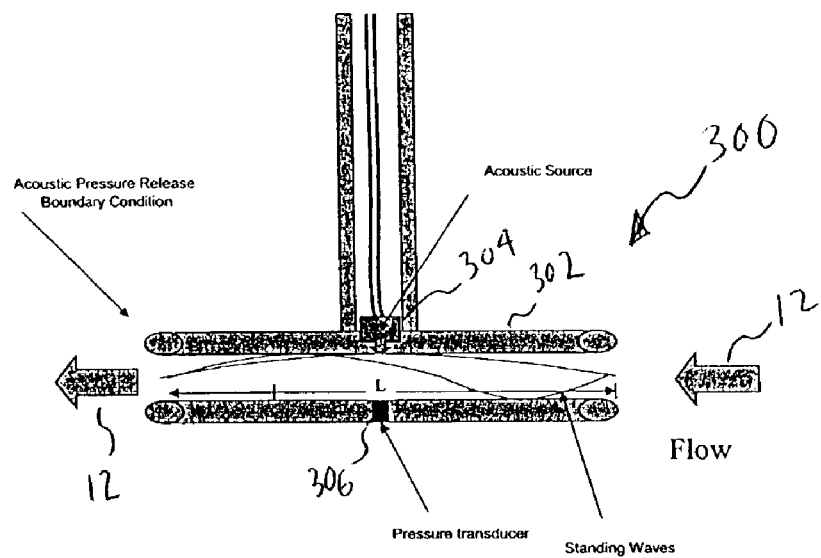
FIG. 43 is a side view in partial cross section of a resonant cavity speed of sound probe in accordance with the present invention.

This disclosure describes a method and apparatus for measuring shown in FIG. 43 the sound speed of a fluid within a duct using a probe 300 immersed within the flow 12, as the probe 300 consists of a tube 302 through which a portion of the flow within the duct is routed. Although the probe is applicable for single-phase flows at low Mach numbers, it primarily intended to accommodate multiphase flows with high subsonic axial Mach numbers. Thus, since the thermophysical properties and characteristics such as homogeneity of multiphase flows can be altered by disturbing either the speed or direction of the high mach number, multiphase flows, the probe is designed to route the fluid of interest through the probe with minimal disturbance to the mean flow conditions.

It is reasonable to model the 1-Dimensional acoustic field of a flowing fluid within a duct with the following partial differential equation (Acoustic of Ducts and Mufflers, M. L. Munjal, John Wiley and Sons, page 18):

$$\frac{1}{a_{mix}^2}\frac{\partial^2 P}{\partial t^2} - \frac{2M_x}{a}\frac{\partial^2 P}{\partial x \partial t} + (M_x^2 - 1)\frac{\partial^2 P}{\partial x^2} = 0$$

The governing equations has propagating wave solutions given as follows:

$$p(x,t) = Ae^{i\omega t - ik_r x_1} + Be^{i\omega t + ik_l x_1}$$

Where $$k_r = \frac{\omega}{a_{mix}(1+M_x)} \qquad k_l = \frac{\omega}{a_{mix}(1-M_x)};$$

and $M_x$ is the axial Mach number and $a_{mix}$ is the mixture sound speed.

Acoustics in ducts have a so-called cut-on frequency, below which only one-dimensional acoustic waves propagate. Since this probe is based on extracting information for the resonant behavior of the one-dimensional acoustics, it is prudent to design the probe to operate at frequencies below the cut-on frequency. For circular ducts, the cut-on frequency is given by (Munjal, p12):

$$f_{cut-on} = \frac{1.84}{D\pi}a_{mix}$$

For a 1 inch diameter circular tube in a fluid with speed of sound of 1000 ft/sec, the cut-on frequency is ~7000 Hz.

Consider an open-open tube 302 suspended in a significantly large duct, $A_{tube} \ll A_{duct}$. For pressure waves propagating within the tube, provided the pressure waves are not correlated to pressure variations within the larger duct, the open ends of the tube appear as pressure release boundaries. Note that more sophisticated models for the radiation impedance of the open ends could be employed without altering the basic ideas behind this disclosure. For example, see (Munjal, page 48). Such conditions hold for pressure waves generated internally to the pipe. Applying the idealized boundary conditions at x=0 and x=L results in the following relations which determine the natural modes of the acoustic within the tube.

$$p(x=0,t) \Longrightarrow A+B=0$$

$$p(x=L,t) \Longrightarrow Ae^{-ik_r L}+Be^{ik_l L}=0$$

Combining the above equations and solving for the conditions for which the system admits non-trivial solutions results in the following transcendental solution for the eigenvalues of the system:

$$e^{-i\frac{\omega}{a_{mix}(1+M_x)}L} - e^{i\frac{\omega}{a_{mix}(1-M_x)}L} = 0$$

Thus, for a tube 302 of known length, the sound speed of the fluid, the axial mach number of the fluid, and the natural frequency of the system are linked through the solution of the above equation. Provided an accurate method and apparatus are available for determining the natural frequency of the tube suspended in a duct, the natural frequency measurement can be used to determine the speed of sound of the flow 12 in duct. For ducts with vanishingly small axial Mach numbers, $M_x \ll 1$, there is a direct relationship between resonant frequency and sound speed.

$$f = n\frac{a_{mix}}{2L}$$

For illustration purposes, consider a 1-foot tube (L=1 ft), immersed in a low Mach number flow with a sound speed of 1000 feet per second (amix=1000 f/sec). In this example, the tube would have resonant acoustic frequencies of 500 Hz (n=1), 1000 Hz (n=2), etc. As the frequency increases, the model becomes less appropriate due to many factors including the increasing inaccuracy of the pressure release boundary condition and the plane wave assumption.

Figure 41:
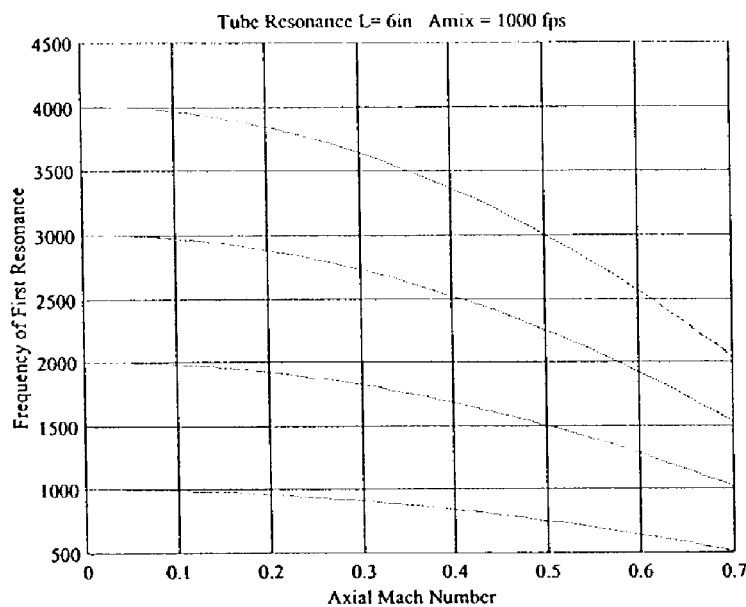
FIG. 41 is a graph of resonant frequency versus axial Mach number for a resonant cavity having a 6-inch diameter in accordance with the present invention.
Figure 42:
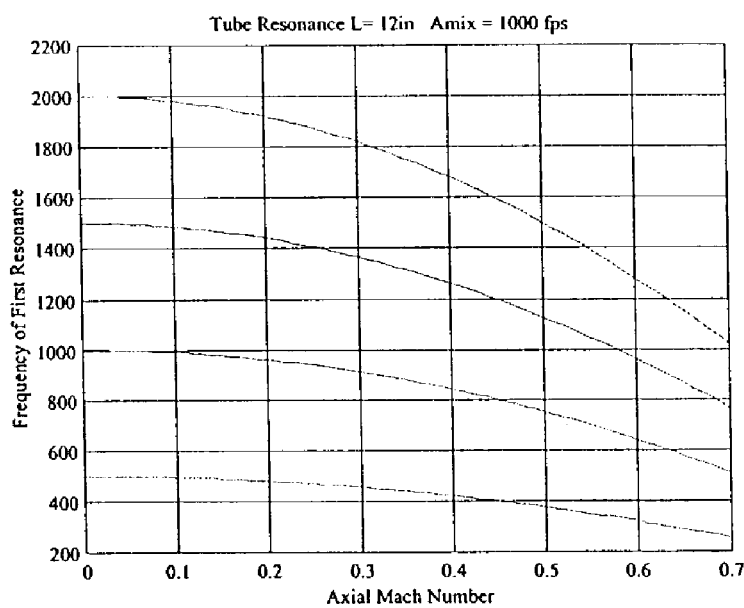
FIG. 42 is a graph of resonant frequency versus axial Mach number for a resonant cavity having a 12-inch diameter in accordance with the present invention.

For applications with non-trivial axial mach numbers of the flow contained within the tube 302, the eigenvalue problem can be solved numerically. The effect of axial Mach number on the resonance frequencies (n=1, 2, 3, 4) of 6 inch and 12 inch tubes containing fluid with a sound speed of 1000 ft/sec are shown in FIGS. 41 and 42, respectively. As shown, the effect is to reduce the frequencies of the acoustic resonances.

As developed above, the resonant frequency of the probe 300 is linked to the speed of sound propagating through the flow 12. The probe incorporates a means 304 for generating sound internal to the tube and a means 306 to sense sound within the tube as shown in FIG. 43. With these features, system identification techniques can be used to accurately and robustly determine the resonant frequency of the acoustic system. The acoustic source 304 may be any known or contemplated device capable of generating a resonant condition within the tube 302, i.e. a speaker, piezo-electric crystal, shaker, etc. The sensor 306 may similarly be any known or contemplated device capable of detecting the resonant condition such as a pressure transducer, a microphone, a fiber optic transducer, other fiber optic based sensor, or the like.

The transfer function between the input to the acoustic source 304 to the output of the microphone and be expressed parametrically as follows:

$$H(s) = \frac{Num}{Den} = \frac{\sum_{n=1}^{N_{zeros}} s - a_n}{\sum_{n=1}^{N_{poles}} s - b_n}$$

The natural frequency of the acoustic tube 302 will appear as poles of the transfer function. For $2^{nd}$ order, non-critically damped systems, the poles are related to the damping and natural frequency through the following relations:

$$b_n = -\zeta\omega_{nat} \pm i(\sqrt{1-\zeta^2})\omega_{nat}$$

Thus, the procedure for determining the natural frequency of the probe 300 involves determining the transfer function from speaker to microphone, fitting the transfer function with poles and zeros, and determining the natural frequency from the location of the poles. Note, best practices in system identification techniques (known by those skilled in the art) should be employed to assure accurate determination of the poles of the transfer function.

The natural frequency can then be used with knowledge of the mean flow velocity, probe geometry, and any other calibration related data to determine the sound of sound of the flow within the probe 300. Note, the speed of sound propagating through the flow 12 will be associated with the frequency of the resonance. This is important to note for dispersive fluids, i.e. fluids in which the speed of sound changes with frequencies. For example, as will be developed later, multiphase fluids typically exhibit dispersive sound speed characteristics.

Note also, a wide variety of methods are potentially available to either measure or estimate the axial velocity of the flow 12 through the probe 300 (required to determine $M_x$ or equivalently U). One proposed method is the method of 122 in which the convection velocity of the vortical flow field, coherent over several pipe diameters, is used to measure the axial velocity of the flow 12 within the probe 300.

One of the primary intended applications for this probe 300 is determining the quality of vapor/liquid mixtures 12. For particle/liquid mixtures, the slip between the fluid and the particles is the primary mechanism responsible for the change in sound speed with frequency.

The following relation represents a model for the dispersive behavior of an idealized fluid particle mixture 12.

$$a_{mix}(\omega) = a_{fluid} * \sqrt{\frac{1}{1 + \frac{\varphi_p \rho_p}{\rho_{fluid}\left(1 + \omega^2 \frac{\rho_p^2 v_p^2}{12\pi\mu D}\right)}}}$$

Figure 44:
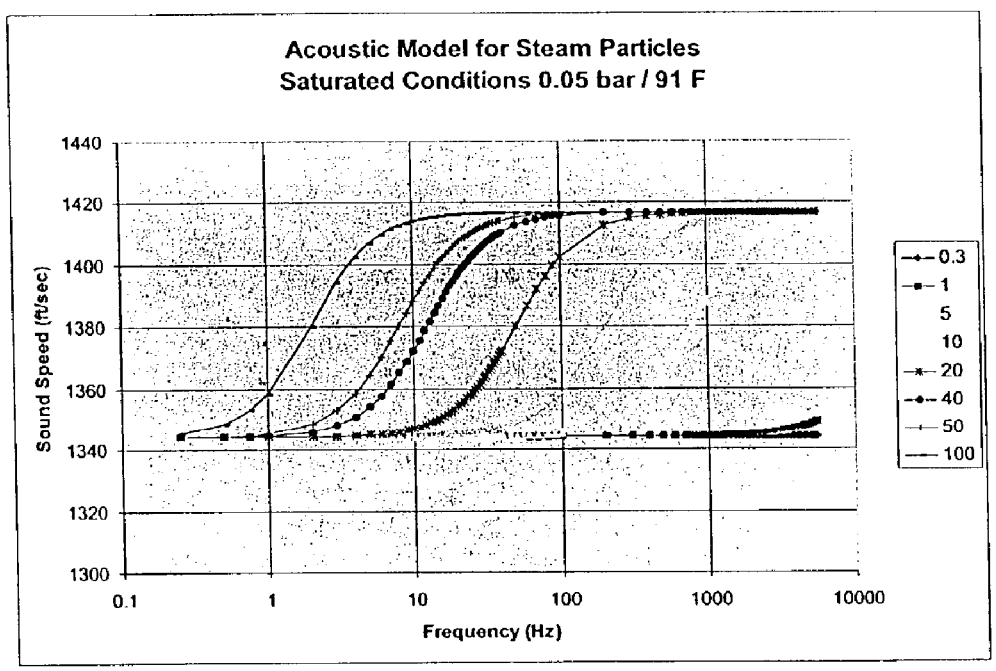
FIG. 44 is a graphical representation of an acoustic model for steam particles in accordance with the present invention.

In the above relation, the fluid SOS, density and viscosity are those of the pure phase fluid, $v_p$ is the volume of individual particles and $\varphi_p$ is the volumetric phase fraction of the particles in the mixture. FIG. 44 shows this relation applied to vapor/liquid mixtures of steam at condition representative of the exit of a Low pressure turbine in power generation applications (T=91 degrees F, P=0.05 Bar)

FIG. 44 illustrates importance of particle size in determining the dispersive characteristics of steam. As shown, both the low frequency and high frequency limits of the sound speed are independent of particle size. The high frequency limit determines the sound speed of vapor phase, and the low frequency limit determines the quality of the steam.

$$a_{mix}(\omega => 0) = a_{fluid} * \sqrt{\frac{1}{1 + \frac{\varphi_p \rho_p}{\rho_{fluid}}}}$$

$$a_{mix}(\omega => \infty) = a_{fluid}$$

For steam mixtures, the quality of the steam is given by the squared ratio of the quasi-steady sound speed and the pure phase vapor sound speed.

$$\text{Quality} = \frac{m_{vapor}}{m_{vapor} + m_{liquid}} = \frac{1}{1 + \frac{\varphi_p \rho_p}{\rho_{fluid}}}$$

$$a_{mix}(\omega => 0) = a_{vapor} * \sqrt{\text{Quality}}$$

$$\text{Quality} = \left(\frac{a_{mix}(\omega => 0)}{a_{vapor}}\right)^2$$

For dispersive mixtures, the multiple resonances of the acoustic cavity probe 300 provides a means to determine measure the sound speeds at several frequencies with a single device. For steam applications, measuring the sound speed at several frequencies provides a means to determine quality as well as particle size. The dispersion model shows that the frequency ranges over which the dispersive behavior is most pronounced is strongly dependent on particle size. If particle size was an important parameter, the probe could be designed such that the range of resonant frequencies span the frequency range in which the dispersive effects are most pronounced. For example, a 12-inch probe in steam would be well suited to determine particle size for 5 micron particles, but not well suited to determine particle size for 50 microns (probe resonances would only correspond to sound speeds in the high frequency limit) nor 0.3 micron particles (probe resonances would only correspond to sound speeds in the low frequency limit).

Figure 45:
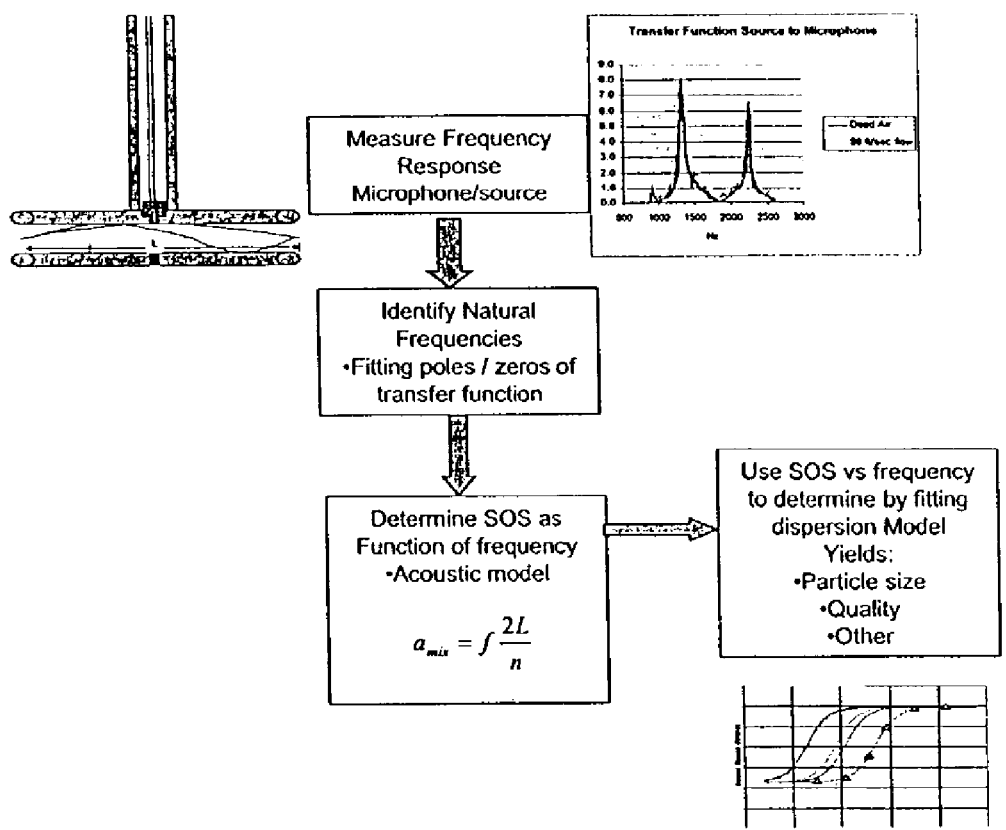
FIG. 45 is a schematic representation of a resonant cavity speed of sound system incorporating a probe in accordance with the present invention.

FIG. 45 outlines a flow chart describing the method for using a resonant cavity sound speed probe to characterize dispersive mixtures. The steps of the method includes measuring the frequency response acoustical source to the microphone. The natural frequencies are identified and the poles and zeroes are fit to the transfer function of the acoustical source to the pressure transducer (e.g., microphone). The speed of sound propagating through the probe is determined as a function of frequency. The SOS vs frequency function is used to determine by fitting the dispersion Model yields to determine a parameter of the fluid or mixture, such as the particle size and steam quality.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. A probe for measuring at least one parameter of a fluid flow, said probe comprising:
   a probe portion adapted to be disposed in the fluid flow, said probe portion including:
   a tube having an open input end and an open output end for receiving a portion of the fluid flow; and
   an array of at least two sensors, each sensor being disposed at different axial locations along the tube, and each sensor measuring an unsteady pressure at a corresponding axial location along the tube, each of said sensors providing a measured signal indicative of the unsteady pressure within the tube at said corresponding axial location of each sensor, wherein the unsteady pressure propagates with the fluid flow; and a signal processor, responsive to said measured signals, which determines the slope of a convective ridge in k-ω plane to provide an output indicative of the velocity of the portion of the fluid flow passing through the tube.

2. The probe of claim 1, the array comprises at least 4, 5, 6, 7, 8, 9, 10, 11, 12, 13, 14, 15, or 16 of said sensors.

3. The probe of claim 1, wherein the signal processor comprises logic, which calculates a volumetric flow rate of the fluid flow.

4. The probe of claim 1, wherein at least one of said sensors include a pressure sensor, a displacement sensor, or a strain-based sensor.

5. The probe of claim 1, wherein at least one sensor provides a first filter which measures a vortical pressure field at a first axial location along the tube and provides a first pressure signal indicative of said vortical pressure field; and
at least a second sensor provides a second filter which measures said vortical pressure field at a second axial location along the tube and provides a second pressure signal indicative of said vortical pressure field.

6. The probe of claim 5, wherein the signal processor, responsive to said first and second pressure signals, provides a velocity signal indicative of a velocity of the said vortical pressure field moving in the tube.

7. The probe of claim 5, wherein said first and said second filters filter out wavelengths associated with an acoustic pressure field and passes wavelengths associated with said vortical pressure field.

8. The probe of claim 7, wherein said first filter comprises a first spatial filter that includes at least a first and a second unsteady pressure sensors disposed a predetermined first distance apart from each other; and
said second filter comprises a second spatial filter that includes at least a third and a fourth unsteady pressure sensors disposed a predetermined second distance apart from each other.

9. The probe of claim 1, wherein the sensors of the array measure a vortical field at each respective axial location along the tube and provides a signal indicative of said vortical pressure field.

10. The probe of claim 9, wherein the processor, responsive to said measured signals indicative of the vortical pressure fields, provides a signal indicative of a velocity of the vortical pressure field, a velocity of the fluid flow, and/or a volumetric flow rate of the fluid flow moving in the tube.

11. The probe of claim 1, wherein the signal processor uses cross-correlation logic, in response to the measured signals, to determine the velocity of the fluid flow.

12. The probe of claim 1, wherein the array comprises three sensors.

13. A method to measure at least one parameter of a fluid flow in a confined or unconfined space, said method comprising:
providing a probe adapted to be disposed in the fluid flow, wherein said probe comprises a tube having an open input end and an open output end for receiving a portion of the fluid flow and an array of at least two sensors, disposed at different axial locations along the tube, each of the sensors being adapted to measure an unsteady pressure propagating with the fluid flow within the tube at a corresponding axial location, each of said sensors providing a measured signal indicative of the unsteady pressure within the tube at said axial location of a corresponding one of said sensors, wherein the unsteady pressure propagates with the fluid flow;

measuring said unsteady pressure using said sensors; and determining, in response to the measures signals, the slope of a convective ridge in k-ω plane;

outputting, in response to the slope of the convective ridge, a velocity of the portion of the fluid flow passing through tube.

14. The method of claim 13, wherein the array comprises at least 4, 5, 6, 7, 8, 9, 10, 11, 12, 13, 14, 15, or 16 of said sensors.

15. The method of claim 13, providing said signal processor to comprise logic which calculates a volumetric flow rate of the fluid flow.

16. The method of claim 13, wherein at least one of said sensors include a pressure sensor, a displacement sensor, or a strain-based sensor.

17. The method of claim 13, wherein the sensors of the array measure a vortical field at each respective axial location along the tube and provides a signal indicative of said vortical pressure field.

18. The method of claim 17, wherein the processor, responsive to said measured signals indicative of the vortical pressure fields, provides a signal indicative of a velocity of the vortical pressure field, a velocity of the fluid flow; and/or a volumetric flow rate of the fluid flow moving in the tube.

19. The method of claim 13, wherein the signal processor uses cross-correlation logic, in response to the measured signals, to determine the velocity of the fluid flow.

20. The method of claim 13, wherein the spatial array comprises three sensors.

21. A probe for measuring at least one parameter of a fluid flow, said probe comprising:
a probe portion adapted to be disposed in the fluid flow, said probe portion including:
a tube having an open input end and an open output end for receiving a portion of the fluid flow; and
an array of at least two sensor, disposed at different axial locations along the tube, and each measuring an acoustic pressure at a corresponding axial location, each of said sensor providing a measured signal indicative of the acoustic pressure propagating through the fluid flow within the tube at said axial location of corresponding one of said sensors, wherein the acoustic pressure propagates past the array of sensors; and
a signal processor, responsive to said measured signals, which provides a signal indicative of the speed of sound propagating through the portion of the fluid flow passing through the tube, wherein the signal processor comprises logic, which calculates a phase fraction of fluid and/or gas portion of the fluid flow.

22. A probe for measuring at least one parameter of a fluid flow, said probe comprising:
probe portion adapted to be disposed in the fluid flow, said probe portion including:
a tube having an open input end and an open output end for receiving a portion of the fluid flow; and
an array of at least two sensors, disposed at different axial locations alone the tube, and each measuring an acoustic pressure at a corresponding axial location, each of said sensors providing a measured signal indicative of the acoustic pressure propagating through the fluid flow within the rube at said axial location of a corresponding one of said sensors, wherein the acoustic pressure propagates past the array of sensors; and a signal processor, responsive to said measured signals, which provides a signal indicative of the speed of sound propagating through the portion of the fluid flow passing through the tube, wherein the signal processor, responsive to the speed of sound, determines a phase fraction utilizing a dispersion model.

23. A probe for measuring at least one parameter of a fluid flow, said probe comprising:

a probe portion adapted to be disposed in the fluid flow, said probe portion including:

a tube having an oven input end and an open output end for receiving a portion of the fluid flow; and an array of at least two sensors, disposed at different axial locations along the tube, and each measuring an acoustic pressure at a corresponding axial location, each of said sensors providing a measured signal indicative of the acoustic pressure propagating through the fluid flow within the tube at said axial location of a corresponding one of said sensors, wherein the acoustic pressure propagates past the array of sensors; and a signal processor, responsive to said measured signals, which provides a signal indicative of the speed of sound propagating through the portion of the fluid flow passing through the tube, wherein the signal processor determines the slope of an acoustic ridge in k-ω plane to determine the speed of sound propagating through the fluid flow.

24. A probe for measuring at least one parameter of a fluid flow, said probe comprising:

a probe portion adapted to be disposed in the fluid flow, said probe portion including:

a tube having an open input end and an open output end for receiving a portion of the fluid flow; and an array of at least two sensors, disposed at different axial locations along the tube, and each measuring an acoustic pressure at a corresponding axial location, each of said sensors providing a measured signal indicative of the acoustic pressure propagating through the fluid flow within the tube at said axial location of a corresponding one of said sensors, wherein the acoustic pressure propagates past the array of sensors; and a signal processor, responsive to said measured signals, which provides a signal indicative of the speed of sound propagating through the portion of the fluid flow passing through the tube, wherein the signal processor uses cross-correlation logic, in response to the measured signals, to determine the speed of sound propagating through the fluid flow.

25. A probe for measuring at least one parameter of a fluid flow, said probe comprising:

a probe portion adapted to be disposed in the fluid flow, said probe portion including:

a tube having an open input end and an open output end for receiving a portion of the fluid flow; and an array of at least two sensors, disposed at different axial locations along the tube, and each measuring an acoustic pressure at a corresponding axial location each of said sensors providing a measured signal indicative of the acoustic pressure propagating through the fluid flow within the tube at said axial location of a corresponding one of said sensors, wherein the acoustic pressure propagates past the array of sensors; and a signal processor, responsive to said measured signals, which provides a signal indicative of the speed of sound propagating through the portion of the fluid flow passing through the tube, wherein the signal processor, responsive to the speed of sound, determines particle/droplet size of the fluid flow utilizing a dispersion model.

* * * * *